United States Patent
Lo et al.

(10) Patent No.: US 12,234,515 B2
(45) Date of Patent: *Feb. 25, 2025

(54) ENHANCEMENT OF CANCER SCREENING USING CELL-FREE VIRAL NUCLEIC ACIDS

(71) Applicant: The Chinese University of Hong Kong, Shatin (HK)

(72) Inventors: Yuk-Ming Dennis Lo, Homantin (CN); Rossa Wai Kwun Chiu, Shatin (CN); Kwan Chee Chan, Jordan (CN); Peiyong Jiang, Shatin (CN); Wai Kei Lam, Kowloon (CN)

(73) Assignee: The Chinese University of Hong Kong, New Territories (HK)

( * ) Notice: Subject to any disclaimer, the term of this patent is extended or adjusted under 35 U.S.C. 154(b) by 730 days.

This patent is subject to a terminal disclaimer.

(21) Appl. No.: 16/912,410

(22) Filed: Jun. 25, 2020

(65) Prior Publication Data

US 2020/0325546 A1    Oct. 15, 2020

Related U.S. Application Data

(63) Continuation of application No. 16/046,795, filed on Jul. 26, 2018, now Pat. No. 10,731,224.

(60) Provisional application No. 62/537,328, filed on Jul. 26, 2017.

(51) Int. Cl.
  *C12Q 1/6886*   (2018.01)
  *C12Q 1/70*    (2006.01)

(52) U.S. Cl.
  CPC ............. *C12Q 1/6886* (2013.01); *C12Q 1/70* (2013.01); *C12Q 1/705* (2013.01); *C12Q 1/706* (2013.01); *C12Q 2600/154* (2013.01)

(58) Field of Classification Search
  None
  See application file for complete search history.

(56) References Cited

U.S. PATENT DOCUMENTS

| | | |
|---|---|---|
| 7,704,687 B2 | 4/2010 | Wang et al. |
| 8,620,593 B2 | 12/2013 | Lo et al. |
| 8,722,334 B2 | 5/2014 | Lo et al. |
| 8,741,811 B2 | 6/2014 | Lo et al. |
| 9,121,069 B2 | 9/2015 | Lo et al. |
| 9,732,390 B2 | 8/2017 | Lo et al. |
| 9,892,230 B2 | 2/2018 | Lo et al. |
| 10,095,831 B2 | 10/2018 | Duenwald et al. |
| 10,633,713 B2 | 4/2020 | Lo et al. |
| 10,731,224 B2 * | 8/2020 | Lo .............. C12Q 1/6886 |
| 11,459,616 B2 | 10/2022 | Namsaraev et al. |
| 11,479,825 B2 | 10/2022 | Lo et al. |
| 2003/0219765 A1 | 11/2003 | Costa |
| 2005/0164241 A1 | 7/2005 | Hahn et al. |
| 2005/0221314 A1 | 10/2005 | Berlin et al. |
| 2005/0282196 A1 | 12/2005 | Costa |
| 2007/0122823 A1 | 5/2007 | Bianchi et al. |
| 2007/0202525 A1 | 8/2007 | Quake et al. |
| 2008/0206749 A1 | 8/2008 | Lo et al. |
| 2009/0029377 A1 | 1/2009 | Lo et al. |
| 2009/0087847 A1 | 4/2009 | Lo et al. |
| 2010/0041048 A1 | 2/2010 | Diehl et al. |
| 2010/0136560 A1 | 6/2010 | Vogelstein et al. |
| 2011/0171741 A1 | 7/2011 | Wang et al. |
| 2011/0276277 A1 | 11/2011 | Lo et al. |
| 2013/0017958 A1 | 1/2013 | Benz et al. |
| 2013/0040824 A1 | 2/2013 | Lo et al. |
| 2013/0237431 A1 | 9/2013 | Lo et al. |
| 2014/0080715 A1 | 3/2014 | Lo et al. |
| 2014/0100121 A1 | 4/2014 | Lo et al. |
| 2014/0178348 A1 | 6/2014 | Kelsey et al. |
| 2014/0227699 A1 | 8/2014 | Lo et al. |

(Continued)

FOREIGN PATENT DOCUMENTS

| | | |
|---|---|---|
| CN | 1790021 | 6/2006 |
| CN | 101622362 | 1/2010 |

(Continued)

OTHER PUBLICATIONS

Wong TS, Kwong DL, Sham JS, Wei WI, Kwong YL, Yuen AP. Quantitative plasma hypermethylated DNA markers of undifferentiated nasopharyngeal carcinoma. Clin Cancer Res. Apr. 1, 2004;10(7):2401-6. (Year: 2004).*

Nawaz et al. Detection of nasopharyngeal carcinoma in Morocco (North Africa) using a multiplex methylation-specific PCR biomarker assay. Clin Epigenetics. Aug. 22, 2015;7(1):89. doi: 10.1186/s13148-015-0119-8. PMID: (Year: 2015).*

U.S. Appl. No. 15/793,830, Non-Final Office Action mailed on May 28, 2021, 14 pages.

(Continued)

*Primary Examiner* — Michelle S Horning
(74) *Attorney, Agent, or Firm* — Kilpatrick Townsend & Stockton LLP

(57) ABSTRACT

Cell-free DNA molecules in a mixture of a biological sample can be analyzed to detect viral DNA. Methylation of viral DNA molecules at one or more sites in the viral genome can be determined. Mixture methylation level(s) can be measured based on one or more amounts of the plurality of cell-free DNA molecules methylated at a set of site(s) of the particular viral genome. The mixture methylation level(s) can be determined in various ways, e.g., as a density of cell-free DNA molecules that are methylated at a site or across multiple sites or regions. The mixture methylation level(s) can be compared to reference methylation level(s), e.g., determined from at least two cohorts of other subjects. The cohorts can have different classifications (including the first condition) associated with the particular viral genome. A first classification of whether the subject has the first condition can be determined based on the comparing.

28 Claims, 35 Drawing Sheets
(13 of 35 Drawing Sheet(s) Filed in Color)

(56) References Cited

U.S. PATENT DOCUMENTS

| | | |
|---|---|---|
| 2014/0274740 A1 | 9/2014 | Srinivasan et al. |
| 2015/0011403 A1 | 1/2015 | Lo et al. |
| 2015/0087529 A1 | 3/2015 | Lo et al. |
| 2015/0119260 A1 | 4/2015 | Chen et al. |
| 2015/0361505 A1 | 12/2015 | Song et al. |
| 2015/0368708 A1 | 12/2015 | Talasaz |
| 2016/0002717 A1 | 1/2016 | Lee et al. |
| 2016/0017419 A1 | 1/2016 | Chiu et al. |
| 2016/0186239 A1 | 6/2016 | Sinha |
| 2016/0201142 A1 | 7/2016 | Lo et al. |
| 2016/0203260 A1 | 7/2016 | Lo et al. |
| 2016/0217251 A1 | 7/2016 | Lo et al. |
| 2016/0292356 A1 | 10/2016 | Kim et al. |
| 2016/0333416 A1 | 11/2016 | Babiarz et al. |
| 2017/0024513 A1 | 1/2017 | Lo et al. |
| 2017/0073774 A1 | 3/2017 | Lo et al. |
| 2017/0132363 A1 | 5/2017 | Lo et al. |
| 2017/0175205 A1 | 6/2017 | Toung et al. |
| 2017/0211143 A1 | 7/2017 | Shendure et al. |
| 2017/0235877 A1 | 8/2017 | Lo et al. |
| 2017/0260590 A1 | 9/2017 | Eltoukhy et al. |
| 2017/0321284 A1 | 11/2017 | McCarroll et al. |
| 2017/0356053 A1 | 12/2017 | Otto et al. |
| 2018/0119230 A1 | 5/2018 | Velculescu et al. |

FOREIGN PATENT DOCUMENTS

| | | | |
|---|---|---|---|
| CN | 102369299 | | 3/2012 |
| CN | 104662168 | | 5/2015 |
| CN | 104781421 | | 7/2015 |
| CN | 104781422 | | 7/2015 |
| CN | 105296606 | A | 2/2016 |
| CN | 105874068 | | 8/2016 |
| CN | 106795562 | | 5/2017 |
| CN | 108026572 | A | 5/2018 |
| CN | 110100013 | A | 8/2019 |
| EA | 005140 | | 12/2004 |
| EA | 010571 | | 10/2008 |
| EA | 011608 | | 4/2009 |
| EA | 018444 | | 8/2013 |
| EP | 2426217 | | 3/2012 |
| EP | 2864501 | | 4/2015 |
| GB | 2485635 | | 5/2012 |
| JP | 2005514956 | | 5/2005 |
| JP | 2010534068 | | 11/2010 |
| JP | 2010534069 | | 11/2010 |
| JP | 2014534507 | | 12/2014 |
| JP | 2015536639 | A | 12/2015 |
| KR | 20150082228 | A | 7/2015 |
| WO | 0061612 | | 10/2000 |
| WO | 03062441 | | 7/2003 |
| WO | 2004078999 | | 9/2004 |
| WO | 2004111272 | | 12/2004 |
| WO | 2007028155 | | 3/2007 |
| WO | 2007100911 | | 9/2007 |
| WO | 2008024009 | | 2/2008 |
| WO | 2008104122 | | 9/2008 |
| WO | 2008146309 | | 12/2008 |
| WO | 2009013492 | | 1/2009 |
| WO | 2009013496 | | 1/2009 |
| WO | 2009019455 | | 2/2009 |
| WO | 2010112316 | | 10/2010 |
| WO | 2011038507 | | 4/2011 |
| WO | 2011053790 | | 5/2011 |
| WO | 2011054936 | | 5/2011 |
| WO | 2011057094 | | 5/2011 |
| WO | 2011073665 | | 6/2011 |
| WO | 2011090557 | | 7/2011 |
| WO | 2011091046 | | 7/2011 |
| WO | 2011103236 | | 8/2011 |
| WO | 2011130751 | | 10/2011 |
| WO | 2012071621 | | 6/2012 |
| WO | 2012103031 | | 8/2012 |
| WO | 2013045432 | | 4/2013 |
| WO | 2013052913 | | 4/2013 |
| WO | 2013060762 | | 5/2013 |
| WO | 2013066641 | | 5/2013 |
| WO | 2013086352 | | 6/2013 |
| WO | 2013132305 | | 9/2013 |
| WO | 2013138510 | | 9/2013 |
| WO | 2013190441 | | 12/2013 |
| WO | 2014004726 | | 1/2014 |
| WO | 2014039556 | | 3/2014 |
| WO | 2014043763 | | 3/2014 |
| WO | WO-2014043763 A1 * | 3/2014 | ........... C12Q 1/6806 |
| WO | 2014130890 | | 8/2014 |
| WO | 2015169947 | | 11/2015 |
| WO | 2015159292 | | 12/2015 |
| WO | 2016008451 | | 1/2016 |
| WO | 2016015058 | | 1/2016 |
| WO | 2016054255 | | 4/2016 |
| WO | 2016094853 | | 6/2016 |
| WO | 2016112850 | | 7/2016 |
| WO | 2016116033 | | 7/2016 |
| WO | 2016127944 | | 8/2016 |
| WO | 2017012544 | | 1/2017 |
| WO | 2017012592 | | 1/2017 |
| WO | 2017019751 | | 2/2017 |
| WO | 2017105353 | | 6/2017 |
| WO | 2017206888 | | 12/2017 |
| WO | 2018081130 | | 5/2018 |
| WO | 2018137685 | | 8/2018 |

OTHER PUBLICATIONS

U.S. Appl. No. 15/793,830, Non-Final Office Action mailed on Feb. 17, 2021, 20 pages.

Accomando et al., Quantitative Reconstruction of Leukocyte Subsets Using DNA Methylation, Genome Biology, vol. 15, No. R50, 2014, 12 pages.

Alexandrov et al., Signatures of Mutational Processes in Human Cancer, Nature, vol. 500, No. 7463, Aug. 22, 2013, 24 pages.

Batzer et al., Enhanced Evolutionary PCR Using Oligonucleotides with Inosine at the 3'-Terminus, Nucleic Acids Research, vol. 19, No. 18, Sep. 25, 1991, p. 5081.

Benjamini et al., Controlling the False Discovery Rate—A Practical and Powerful Approach to Multiple Testing, Journal of the Royal Statistical Society Series B-Statistical Methodology, vol. 57, No. 1, Nov. 1995, pp. 289-300.

Bettegowda et al., Detection of Circulating Tumor DNA in Early- and Late-Stage Human Malignancies, Science Translational Medicine, vol. 6, No. 224, Feb. 19, 2014, 25 pages.

Boyle et al., High-Resolution Mapping and Characterization of Open Chromatin Across the Genome, Cell, vol. 132, No. 2, Jan. 25, 2008, pp. 311-322.

Buenrostro et al., Transposition of Native Chromatin for Fast and Sensitive Epigenomic Profiling of Open Chromatin, DNA-Binding Proteins and Nucleosome Position, Nature Methods, vol. 10, No. 12, Dec. 2013, pp. 1213-1218.

Chan et al., Plasma DNA Aberrations in Systemic Lupus Erythematosus Revealed by Genomic and Methylomic Sequencing, Proceedings of the National Academy of Sciences, vol. 111, No. 49, Nov. 26, 2014, pp. E5302-E5311.

Chan et al., Second Generation Noninvasive Fetal Genome Analysis Reveals De Novo Mutations, Single-Base Parental Inheritance, and Preferred DNA Ends, Proceedings of the National Academy of Sciences of the United States of America, vol. 113, No. 50, Dec. 13, 2016, pp. E8159-E8168.

Chim et al., Detection of the Placental Epigenetic Signature of the Maspin Gene in Material Plasma, XP-002355638, Proceedings of the National Academy of Sciences of the United States of America, vol. 102, No. 41, Oct. 11, 2005, pp. 14753-14758.

De Mattos-Arruda et al., Cerebrospinal Fluid-Derived Circulating Tumour DNA Better Represents the Genomic Alterations of Brain Tumours than Plasma, Nature Communications, vol. 6, Nov. 10, 2015, 6 pages.

De Vlaminck et al., Noninvasive Monitoring of Infection and Rejection After Lung Transplantation, Proceedings of the National Academy of Sciences, vol. 112, No. 43, Oct. 27, 2015, pp. 13336-133341.

(56) References Cited

OTHER PUBLICATIONS

Dear, One by One: Single Molecule Tools for Genomics, Briefings in Functional Genomics and Proteomics, vol. 1, No. 4, Jan. 2003, pp. 397-416.
Dressman et al., Transforming Single DNA Molecules into Fluorescent Magnetic Particles for Detection and Enumeration of Genetic Variations, Proceedings of the National Academy of Sciences of the United States of America, vol. 100, No. 15, Jul. 22, 2003, pp. 8817-8822.
European Application No. 18838558.7, Office Action mailed on Mar. 7, 2022, 7 pages.
Fernandez et al., A DNA Methylation Fingerprint of 1628 Human Samples, Genome Research, vol. 22, No. 2, Feb. 2012, pp. 407-419.
Giresi et al., FAIRE (Formaldehyde-Assisted Isolation of Regulatory Elements) Isolates Active Regulatory Elements from Human Chromatin, Genome Research, vol. 17, No. 6, Jun. 2007, pp. 877-885.
Harris et al., Single-Molecule DNA Sequencing of a Viral Genome, Science, vol. 320, No. 5872, Apr. 4, 2008, pp. 106-109.
Houseman et al., Cell-Composition Effects in the Analysis of DNA Methylation Array Data: A Mathematical Perspective, BMC Bioinformatics, vol. 16, No. 95, 2015, 16 pages.
Houseman et al., DNA Methylation Arrays as Surrogate Measures of Cell Mixture Distribution, BMC Bioinformatics, vol. 13, No. 86, May 8, 2012, pp. 1-16.
Houseman et al., Reference-Free Cell Mixture Adjustments in Analysis of DNA Methylation Data, Bioinformatics, Genetics and Population Analysis, vol. 30, No. 10, May 15, 2014, pp. 1431-1439.
Korbel et al., Paired-End Mapping Reveals Extensive Structural Variation in the Human Genome, Science, vol. 318, No. 5849, Oct. 19, 2007, pp. 420-426.
Li et al., A Survey of Sequence Alignment Algorithms for Next-generation Sequencing, Briefings in Bioinformatics, vol. 11, No. 5, May 11, 2010, pp. 473-483.
Li et al., SOAP2: An Improved Ultrafast Tool for Short Read Alignment, Bioinformatics, vol. 25, No. 15, Aug. 1, 2009, pp. 1966-1967.
Lian et al., Loss of 5-Hydroxymethylcytosine as an Epigenetic Hallmark of Melanoma, Cell, vol. 150, Issue 6, Sep. 14, 2012, pp. 1135-1146.
Liu et al., Decoding Circulating Nucleic Acids in Human Serum Using Microfluidic Single Molecule Spectroscopy, Journal of the American Chemical Society, vol. 132, No. 16, Apr. 5, 2010, pp. 5793-5798.
Margulies et al., Genome Sequencing in Microfabricated High-Density Picolitre Reactors, Nature, vol. 437, No. 7057, Sep. 15, 2005, pp. 376-380.
Mazurek et al., Assessment of the Total cfDNA and HPV16/18 Detection in Plasma Samples of Head and Neck Squamous Cell Carcinoma Patients, Oral Oncology, vol. 54, Jan. 11, 2016, pp. 36-41.
Norton et al., Cell-Free DNA Analysis for Noninvasive Examination of Trisomy, The New England Journal of Medicine, vol. 372, No. 17, Apr. 23, 2015, pp. 1589-1597.
Nygren et al., Quantification of Fetal DNA by Use of Methylation-Based DNA Discrimination, Clinical Chemistry, vol. 56, No. 10, Available Online at: http://www.clinchem.org/content/suppl/2010/07/28/clinchem.2010.146290.DC1/clinchem.2010.146290-1.pdf, Aug. 20, 2010, pp. 1627-1635.
Ohtsuka et al., An Alternative Approach to Deoxyoligonucleotides as Hybridization Probes by Insertion of Deoxyinosine at Ambiguous Codon Positions, Journal of Biological Chemistry, vol. 260, No. 5, Mar. 10, 1985, pp. 2605-2608.
Rossolini et al., Use of Deoxyinosine-Containing Primers Vs Degenerate Primers for Polymerase Chain Reaction Based on Ambiguous Sequence Information, Molecular and Cellular Probes, vol. 8, No. 2, Apr. 1994, pp. 91-98.
Singapore Application No. 11201903509Q, Written Opinion mailed on Dec. 21, 2021, 7 pages.

Shendure et al., Next-Generation DNA Sequencing, Nature Biotechnology, vol. 26, No. 10, Oct. 1, 2008, pp. 1135-1145.
Snyder et al., Cell-Free DNA Comprises an In Vivo Nucleosome Footprint That Informs Its Tissues-Of-Origin, Cell, vol. 167, Jan. 2016, pp. 57-68.
Soni et al., Progress Toward Ultrafast DNA Sequencing Using Solid-State Nanopores, Clinical Chemistry, vol. 53, No. 11, Nov. 1, 2007, pp. 1996-2001.
Taiwan Application No. 106136597, Office Action mailed on Nov. 25, 2021, 6 pages (5 pages of Original Document and 1 pages of English Translation).
U.S. Appl. No. 13/789,553, Final Office Action mailed on May 5, 2017, 16 pages.
U.S. Appl. No. 13/789,553, Non-Final Office Action mailed on Feb. 12, 2016, 18 pages.
U.S. Appl. No. 13/789,553, Non-Final Office Action mailed on Oct. 13, 2016, 20 pages.
U.S. Appl. No. 13/789,553, Notice of Allowance mailed on Oct. 5, 2017, 8 pages.
U.S. Appl. No. 14/089,720, Non-Final Office Action mailed on Aug. 23, 2016, 15 pages.
U.S. Appl. No. 15/880,403, Diagnostic Applications Using Nucleic Acid Fragments filed Jan. 25, 2018, 201 pages.
U.S. Appl. No. 60/951,438, Determining a Nucleic Acid Sequence Imbalance filed Jul. 23, 2007, 90 pages.
U.S. Appl. No. 62/580,906, Using Nucleic Acid Size Range for Noninvasive Prenatal Testing and Cancer Detection filed Nov. 2, 2017, 89 pages.
Allday et al., CpG Methylation of Viral DNA in EBV-Associated Tumours, International Journal of Cancer, vol. 45, 1990, pp. 1125-1130.
Australian Application No. 2013229186, First Examination Report mailed on Dec. 1, 2015, 5 pages.
Camargo et al., Validation and Calibration of Next-Generation Sequencing to Identify Epstein-Barr Virus-Positive Gastric Cancer in the Cancer Genome Atlas, Gastric Cancer, vol. 19, No. 2, Apr. 2016, pp. 676-681.
Chan et al., Effects of Preanalytical Factors on the Molecular Size of Cell-free DNA in Blood, Clinical Chemistry, vol. 51, No. 4, Apr. 2005, pp. 781-784.
Chan et al., Persistent Aberrations in Circulating DNA Integrity after Radiotherapy are Associated with Poor Prognosis in Nasopharyngeal Carcinoma Patients, Imaging, Diagnosis, Prognosis, Clinical Cancer Research, vol. 14, Issue No. 13, Jul. 1, 2008, pp. 4141-4145.
Chen et al., Quantification of 5-Methylcytosine and 5-Hydroxymethylcytosine in Genomic DNA from Hepatocellular Carcinoma Tissues by Capillary Hydrophilic-Interaction Liquid Chromatography/Quadrupole TOF Mass Spectometry, Clinical Chemistry, vol. 59, Issue 5, May 2013, pp. 824-832.
Cook et al., Use and Misuse of the Receiver Operating Characteristic Curve in Risk Prediction, Circulation, vol. 11, No. 5, Feb. 20, 2007, pp. 928-935.
Devonshire et al., Towards Standardisation of Cell-Free DNA Measurement in Plasma: Controls for Extraction Efficiency, Fragment Size Bias and Quantification, Analytical and Bioanalytical Chemistry, vol. 406, No. 26, Oct. 2014, pp. 6499-6512.
European Application No. 13757943.9, Extended European Search Report mailed on Sep. 7, 2015, 7 pages.
European Application No. 14193706.0, Extended European Search Report mailed on Mar. 18, 2015, 7 pages.
European Application No. 14193706.0, Office Action mailed on Nov. 3, 2015, 4 pages.
Fernandez et al., The Dynamic DNA Methylomes of Double-Stranded DNA Viruses Associated with Human Cancer, Genome Research, Cold Spring Harbor Laboratory Press, vol. 19, No. 3, Mar. 1, 2009, pp. 438-451.
Hsiao et al., Detection of Cell Free Epstein-Barr Virus DNA in Sera from Patients with Nasopharyngeal Carcinoma, Cancer, vol. 94, No. 3, Feb. 1, 2002, pp. 723-729.
Jiang et al., Lengthening and Shortening of Plasma DNA in Hepatocellular Carcinoma Patients, Proceedings of the National Academy of Sciences, vol. 112, No. 11, Feb. 2, 2015, pp. E1317-E1325.

(56) References Cited

OTHER PUBLICATIONS

Jo et al., A Single-Molecule Barcoding System using Nanoslits for DNA Analysis, PNAS, vol. 104, No. 8, Feb. 20, 2007, pp. 2673-2678.
Japanese Application No. 2014-560451, Office Action mailed on Feb. 23, 2016, 10 pages (3 pages of Original Document and 7 pages of English Translation).
Japanese Application No. 2017-000134, Office Action mailed on Dec. 12, 2017, 6 pages (2 pages of Original Document and 4 pages of English Translation).
Kanakry et al., Characterizing the CpG Methylation of Epstein-Barr Virus DNA in the Plasma of Patients with Hodgkin Lymphoma and HIV-Associated Burkitt Lymphoma, Blood, vol. 122, No. 21, Nov. 15, 2013, pp. 1-3.
Koh et al., Noninvasive in Vivo Monitoring of Tissue-Specific Global Gene Expression in Humans, Proceedings of the National Academy of Sciences of the United States of America, vol. 111, No. 20, May 20, 2014, pp. 7361-7366.
Kwok et al., Genomic Sequencing and Comparative Analysis of Epstein-Barr Virus Genome Isolated from Primary Nasopharyngeal Carcinoma Biopsy, PLoS One, vol. 7, No. 5, May 2012, pp. 1-10.
Lam et al., Sequencing-based Counting and Size Profiling of Plasma Epstein-Barr Virus DNA Enhance Population Screening of Nasopharyngeal Carcinoma, Proceedings of the National Academy of Sciences of the United States of America, vol. 115, No. 22, May 29, 2018, pp. E5115-E5124.
Lawrence et al., Mutational Heterogeneity in Cancer and the Search for New Cancer Genes, Nature, vol. 499, No. 7457, Jul. 11, 2013, pp. 214-218.
Liu et al., The Diagnostic Accuracy of Pleural Effusion and Plasma Samples Versus Tumour Tissue for Detection of EGFR Mutation in Patients with Advanced Non-small Cell Lung Cancer: Comparison of Methodologies, Journal of Clinical Pathology, vol. 66, No. 12, Dec. 2013, pp. 1065-1069.
Lo et al., Molecular Prognostication of Nasopharyngeal Carcinoma by Quantitative Analysis of Circulating Epstein-Barr Virus DNA, Cancer Research, vol. 60, No. 24, Dec. 15, 2000, pp. 6878-6881.
Lo et al., Quantitative and Temporal Correlation between Circulating Cell-Free Epstein-Barr Virus DNA and Tumor Recurrence in Nasopharyngeal Carcinoma, Cancer Research, vol. 59, Nov. 1, 1999, pp. 5452-5455.
Manokhina et al., Quantification of Cell-free DNA in Normal and Complicated Pregnancies: Overcoming Biological and Technical Issues, PLoS One, vol. 9, No. 7, Jul. 2, 2014, pp. 1-7.
O'Marcaigh et al., Estimating the Predictive Value of a Diagnostic Test, Clinical Pediatrics, vol. 32, No. 8, Aug. 1993, pp. 485-491.
International Application No. PCT/CN2016/070785, International Search Report and Written Opinion mailed on Apr. 22, 2016, 7 pages.
International Application No. PCT/CN2018/097072, International Search Report and Written Opinion mailed on Nov. 5, 2018, 10 pages.
International Application No. PCT/US2017/046582, International Search Report and Written Opinion mailed on Nov. 20, 2017, 12 pages.
Pepe et al., Limitations of the Odds Ratio in Gauging the Performance of a Diagnostic, Prognostic, or Screening Marker, American Journal of Epidemiology, vol. 159, No. 9, May 1, 2004, pp. 882-890.
Robin et al., Comparison of DNA Quantification Methods for Next Generation Sequencing, Scientific Reports, vol. 6, No. 1, Article No. 24067, Apr. 2016, pp. 1-10.
Santpere et al., Genome-Wide Analysis of Wild-Type Epstein-Barr Virus Genomes Derived from Healthy Individuals of the 1000 Genomes Project, Genome Biology, vol. 6, No. 4, Apr. 2014, pp. 846-860.
Stebbing et al., Cell-Free DNA as a Biomarker in the Context of Cancer, Viruses, and Methylation, The Journal of Infectious Diseases, vol. 25, No. 7, Apr. 1, 2012, pp. 1032-1034.
Tanic et al., Epigenome-Wide Association Studies for Cancer Biomarker Discovery in Circulating Cell-Free DNA: Technical Advances and Challenges, Current Opinion in Genetics & Development, vol. 42, Feb. 16, 2017, pp. 48-55.
Tierney et al., Epstein-Barr Virus BamHI W Repeat Number Limits EBNA2/EBNA-LP Coexpression in newly Infected B Cells and the Efficiency of B-Cell Transformation: a Rationale for the Multiple W Repeats in Wild-Type Virus Strains, Journal of Virology, vol. 85, No. 23, Dec. 2011, pp. 12362-12375.
Togneri et al., Genomic Complexity of Urothelial Bladder Cancer Revealed in Urinary cfDNA, European Journal of Human Genetics, vol. 24, No. 8, Aug. 2016, pp. 1167-1174.
Tsuchiya, Diagnosis of Epstein-Barr Virus Associated Diseases, Critical Reviews in Oncology/Hematology, vol. 44, No. 3, Dec. 2002, pp. 227-238.
Umetani et al., Increased Integrity of Free Circulating DNA in Sera Patients with Colorectal or Periampullary Cancer: Direct Quantitative PCR for ALU Repeats, Clinical Chemistry, vol. 52, Issue 6, 2006, pp. 1062-1069.
Wei et al., Current Management Strategy of Nasopharyngeal Carcinoma, Clinical and Experimental Otorhinolaryngology, vol. 3, No. 1, Mar. 2010, pp. 1-12.
Xia et al., Accurate Genome Relative Abundance Estimation Based on Shotgun Metagenomic Reads, PLOS ONE, vol. 6, No. 12, Dec. 6, 2011, pp. 1-12.
Zhao et al., Genome-Wide Methylation Profiling of the Different Stages of Hepatitis B Virus-Related Hepatocellular Carcinoma Development in Plasma Cell-Free DNA Reveals Potential Biomarkers for Early Detection and High-Risk Monitoring of Hepatocellular Carcinoma, Clinical Epigenetics, vol. 6, No. 1, Dec. 2, 2014, pp. 1-18.
TruSeq DNA PCR-Free Sample Preparation Kit, Illumina, Data Sheet: Sequencing, Available online at: http://www.illumina.com/contenUdam/illuminamarketing/documents/products/datasheets/datasheet_truseq_dna_pcr_free_sample_prep.pdf>, 2013, 4 pages.
U.S. Appl. No. 13/801,748, Non-Final Office Action, mailed on Aug. 11, 2017, 18 pages.
U.S. Appl. No. 15/362,631, Non-Final Office Action, mailed on Jan. 11, 2018, 7 pages.
Aird et al., Analyzing and Minimizing PCR Amplification Bias in Illumina Sequencing Libraries, Genome Biology, vol. 12, No. R18, Available online at: http://genomebiology.com/2011/12/2/R18, Feb. 2011, pp. 1-14.
Australia Application No. 2013278994, First Examination Report, mailed on Aug. 17, 2016, 3 pages.
Australia Application No. 2013278994, Notice of Acceptance, mailed on Mar. 23, 2017, 3 pages.
Balakrishnan et al., Epigenetic Regulation of Viral Biological Processes, Viruses, vol. 9, No. 11, 2017, pp. 1-14.
Beck et al., Next Generation Sequencing of Serum Circulating Nucleic Acids from Patients with Invasive Ductal Breast Cancer Reveals Differences to Healthy and Nonmalignant Controls, Molecular Cancer Research, vol. 8, No. 3, Mar. 9, 2010, pp. 335-342.
Beck et al., Profile of the Circulating DNA in Apparently Healthy Individuals, Clinical Chemistry, vol. 55, No. 4, Apr. 2009, pp. 730-738.
Bianchi et al., Large Amounts of Cell-Free Fetal DNA are Present in Amniotic Fluid, Clinical Chemistry, vol. 47, No. 10, Oct. 2001, pp. 1867-1869.
Canada Application No. 2,876,327, Office Action, mailed on Jul. 7, 2017, 4 pages.
Chan et al., Analysis of Plasma Epstein-Barr Virus DNA to Screen for Nasopharyngeal Cancer, The New England Journal of Medicine, vol. 377, No. 6, Aug. 10, 2017, 16 pages.
Chan et al., Cancer Genome Scanning in Plasma: Detection of Tumor-Associated Copy Number Aberrations, Single-Nucleotide Variants, and Tumoral Heterogeneity by Massively Parallel Sequencina, Clinical Chemistry, vol. 59, No. 1, Jan. 2013, pp. 211-224.
Chan et al., Early Detection of Nasopharyngeal Carcinoma by Plasma Epstein-Barr Virus DNA Analysis in a Surveillance Program, Cancer, vol. 119, No. 10, May 15, 2013, pp. 1838-1844.

(56) References Cited

OTHER PUBLICATIONS

Chan et al., Molecular Characterization of Circulating EBV DNA in the Plasma of Nasopharyngeal Carcinoma and Lymphoma Patients, Cancer Research, vol. 63, No. 9, May 1, 2003, pp. 2028-2032.

Chan et al., Noninvasive Detection of Cancer-Associated Genome-Wide Hypomethylation and Copy Number Aberrations by Plasma DNA Bisulfite Sequencing, Proceedings of the National Academy of Sciences, vol. 110, No. 47, Nov. 19, 2013, pp. 18761-18768.

Chan et al., Plasma Epstein-Barr Virus DNA as a Biomarker for Nasopharyngeal Carcinoma, Chinese Journal of Cancer, vol. 33, No. 12, Dec. 2014, pp. 598-603.

Chan et al., Size Distributions of Maternal and Fetal DNA in Maternal Plasma, Clinical Chemistry, vol. 50, No. 1, Jan. 2004, pp. 88-92.

Chandrananda et al., High-Resolution Characterization of Sequence Signatures due to Non-Random Cleavage of Cell-Free DNA, BMC Medical Genomics, vol. 8, No. 29, Jun. 17, 2015, pp. 1-19.

Chang et al., Assessment of Plasma DNA Levels, Allelic Imbalance, and CA 125 as Diagnostic Tests for Cancer, Journal of the National Cancer Institute, vol. 94, No. 22, Nov. 20, 2002, pp. 1697-1703.

Chiu et al., Non-Invasive Prenatal Diagnosis by Single Molecule Counting Technologies, Trends in Genetics, vol. 25, No. 7, Jun. 18, 2009, pp. 324-331.

Chiu et al., Noninvasive Prenatal Diagnosis of Fetal Chromosomal Aneuploidy by Massively Parallel Genomic Sequencing of DNA in Maternal Plasma, Proceedings of the National Academy of Sciences, vol. 105, No. 51, Dec. 23, 2008, pp. 20458-20463.

Cibulskis et al., Sensitive Detection of Somatic Point Mutations in Impure and Heterogeneous Cancer Samples, Nature Biotechnology, vol. 31, No. 3, Mar. 2013, pp. 213-219.

Daniels et al., Whole Genome Sequencing for Lung Cancer, Journal of Thoracic Disease, vol. 4, No. 2, Apr. 1, 2012, pp. 155-163.

Diaz Jr. et al., The Molecular Evolution of Acquired Resistance to Targeted EGFR Blockade in Colorectal Cancers, Nature, vol. 486, No. 7404, Jun. 28, 2012, 10 pages.

Diaz Jr. et al., Supplementary Information: The Molecular Evolution of Acquired Resistance to Targeted EGFR Blockade in Colorectal Cancers, Nature, vol. 486, No. 7404, Jun. 28, 2012, 25 pages.

Diehl et al., Circulating Mutant DNA to Assess Tumor Dynamics, Nature Medicine, vol. 14, No. 9, Sep. 2008, pp. 985-990.

Diehl et al., Detection and Quantification of Mutations in the Plasma of Patients with Colorectal Tumors, Proceedings of the National Academy of Sciences, vol. 102, No. 45, Nov. 8, 2005, pp. 16368-16373.

Ding et al., MS Analysis of Single-Nucleotide Differences in Circulating Nucleic Acids: Application to Noninvasive Prenatal Diagnosis, Proceedings of the National Academy of Sciences of the United States (PNAS), National Academy of Science US, vol. 101, No. 29, Jul. 20, 2004, pp. 10762-10767.

Eurasian Application No. 201500027, Office Action, mailed on Mar. 10, 2017, 19 pages (11 pages of Original Document and 8 pages of English Translation).

Eurasian Application No. 201500027, Office Action, mailed on Dec. 19, 2017, 21 pages (16 pages of Original Document and 21 pages of English Translation).

Ellinger et al., Cell-Free Circulating DNA: Diagnostic Value in Patients with Testicular Germ Cell Cancer, The Journal of Urology, vol. 181, No. 1, Jan. 2009, pp. 363-371.

European Application No. 13807105.5, Extended European Search Report, mailed on Feb. 15, 2016, 9 pages.

European Application No. 13807105.5, Office Action, mailed on Feb. 27, 2017, 10 pages.

Fan et al., Analysis of the Size Distributions of Fetal and Maternal Cell-Free DNA by Paired-End Sequencing, Clinical Chemistry, vol. 56, No. 8, Aug. 2010, pp. 1279-1286.

Fan et al., Detection of Aneuploidy with Digital Polymerase Chain Reaction, Analytical Chemistry, American Chemical Society, vol. 79, No. 19, Oct. 1, 2007, pp. 7576-7579.

Fan et al., Noninvasive Diagnosis of Fetal Aneuploidy by Shotgun Sequencing DNA from Maternal Blood, Proceedings National Academy of Sciences, vol. 105, No. 42, Oct. 21, 2008, pp. 16266-16271.

Fan et al., Whole-Genome Molecular Haplotyping of Single Cells, Nature Biotechnology, vol. 29, No. 1, Jan. 2011, pp. 51-57.

Forshew et al., Noninvasive Identification and Monitoring of Cancer Mutations by Targeted Deep Sequencing of Plasma DNA, Science Translational Medicine, American Association for the Advancement of Science, vol. 4, No. 136, May 30, 2012, pp. 1-12.

Gerlinger et al., Intratumor Heterogeneity and Branched Evolution Revealed by Multiregion Sequencing, The New England Journal of Medicine, vol. 366, No. 10, Available online at: www.nejm.org, Mar. 8, 2012, pp. 883-892.

Goode et al., A Simple Consensus Approach Improves Somatic Mutation Prediction Accuracy, Genome Medicine, vol. 5, No. 90, 2013, pp. 1-14.

Hanlon et al., Evaluation of 13q14 Status in Multiple Myeloma by Digital Single Nucleotide Polymorphism Technology, Journal of Molecular Diagnostics, vol. 11, No. 5, Sep. 2009, pp. 450-457.

Heidary et al., The Dynamic Range of Circulating Tumor DNA in Metastatic Breast Cancer, Breast Cancer Research, vol. 16, No. 421, Aug. 9, 2014, pp. 1-10.

Hongkong Application No. 18101202.2, Search Report, mailed on Feb. 6, 2018, 3 pages.

Hohaus et al., The Viral Load of Epstein-Barr Virus (EBV) DNA in Peripheral Blood Predicts for Biological and Clinical Characteristics in Hodgkin Lymphoma, Clinical Cancer Research, vol. 17, No. 9, May 1, 2011, pp. 2885-2892.

Hou et al., Single-Cell Exome Sequencing and Monoclonal Evolution of a JAK2-Negative Myeloproliferative Neoplasm, Cell, vol. 148, No. 5, Mar. 2, 2012, pp. 873-885.

Israel Application No. 235967, Office Action, mailed on Aug. 14, 2017, 2 pages.

Ivanov et al., Non-Random Fragmentation Patterns in Circulating Cell-Free DNA Reflect Epigenetic Regulation, BMC Genomics, vol. 16, Dec. 16, 2015, 12 pages.

Jacobs et al., Detectable Clonal Mosaicism and its Relationship to Aging and Cancer, Nature Genetics, vol. 44, No. 6, May 6, 2012, 20 pages.

Jahr et al., DNA Fragments in the Blood Plasma of Cancer Patients: Quantitations and Evidence for their Origin from Apoptotic and Necrotic Cells, Cancer Research, vol. 61, No. 4, Feb. 15, 2001, pp. 1659-1665.

Jiang et al., Increased Plasma DNA Integrity Index in Head and Neck Cancer Patients, International Journal of Cancer, vol. 119, No. 11, Dec. 1, 2006, pp. 2673-2676.

Japan Application No. 2015-517896, Office Action, mailed on Jul. 26, 2016, 18 pages (7 pages of Original Document and 11 pages of English Translation).

Japan Application No. 2015-517896, Office Action, mailed on Feb. 6, 2018, 7 pages (3 pages of Original Document and 4 pages of English Translation).

Japan Application No. 2015-517896, Office Action, mailed on Jun. 6, 2017, 7 pages (3 pages of Original Document and 4 pages of English Translation).

Jung et al., Cell-Free DNA in the Blood as a Solid Tumor Biomarker—A Critical Appraisal of the Literature, Clinica Chimica Acta, vol. 411, No. 21-22, Nov. 11, 2010, pp. 1611-1624.

Karlsson et al., Amplification-Free Sequencing of Cell-Free DNA for Prenatal Non-Invasive Diagnosis of Chromosomal Aberrations, Genomics, vol. 105, No. 3, Mar. 2015, pp. 150-158.

Kinde et al., Detection and Quantification of Rare Mutations with Massively Parallel Sequencing, Proceedings of the National Academy of Sciences, vol. 108, No. 23, Jun. 7, 2011, pp. 9530-9535.

Kitzman et al., Noninvasive Whole-Genome Sequencing of a Human Fetus, Science Translation Medicine, vol. 4, Nos. 137-140, Jun. 2012, 11 pages.

Kozarewa et al., Amplification-Free Illumina Sequencing-Library Preparation Facilitates Improved Mapping and Assembly of (GC)-Biased Genomes, Nature Methods, vol. 6, No. 4, Apr. 2009, pp. 291-295.

(56) References Cited

OTHER PUBLICATIONS

Korea Application No. 10-2015-7001225, Office Action, mailed on Oct. 25, 2016, 16 pages (8 pages of Original Document and 8 pages of English Translation).

Laframboise et al., Allele-Specific Amplification in Cancer Revealed by SNP Array Analysis, PLoS Computational Biology, vol. 1, No. 6, Nov. 2005, pp. 0507-0517.

Lam et al., Sequencing-Based Counting and Size Profiling of Plasma Epstein-Barr Virus DNA Enhance Population Screening of Nasopharyngeal Carincinoma, Science Translational Medicine Submitted Manuscript; Template Updated, Feb. 2012, 49 pages.

Lapaire et al., Array-CGH Analysis of Cell-Free Fetal DNA in 10 mL of Amniotic Fluid Supernatant, Prenatal Diagnosis, vol. 27, No. 7, Jul. 2007, pp. 616-621.

Lapaire et al., Cell-Free Fetal DNA in Amniotic Fluid: Unique Fragmentation Signatures in Euploid and Aneuploid Fetuses, Clinical Chemistry, vol. 53, No. 3, Mar. 2007, pp. 405-411.

Lapaire et al., Larger Columns and Change of Lysis Buffer Increase the Yield of Cell-Free DNA Extracted from Amniotic Fluid, Clinical Chemistry, vol. 52, No. 1, Jan. 2006, pp. 156-157.

Larkin et al., A Phase II Trial of Nilotinib in the Treatment of Patients with KIT Mutated Advanced Acral and Mucosal Melanoma (NICAM), Online Conference Poster, Institute of Cancer Research, Available Online at: https://media4.asco.org/102/6682/59779/59779_poster_big_1.jpg, May 20, 2011, 3 pages.

Larrabee et al., Microarray Analysis of Cell-Free Fetal DNA in Amniotic Fluid: A Prenatal Molecular Karyotype, The American Society of Human Genetics, vol. 75, No. 3, Sep. 1, 2004, pp. 485-491.

Leary et al., Detection of Chromosomal Alterations in the Circulation of Cancer Patients with Whole-Genome Sequencing, Science Translational Medicine, vol. 4, No. 162, Nov. 28, 2012, pp. 1-21.

Leary et al., Development of Personalized Tumor Biomarkers Using Massively Parallel Sequencing, Science Translational Medicine, vol. 2, No. 20, Available Online at: www.ScienceTranslationaiMedicine.org, Feb. 24, 2010, 15 pages.

Lecoeur, Nuclear Apoptosis Detection by Flow Cytometry: Influence of Endogenous Endonucleases, Experimental Cell Research, vol. 277, No. 1, Jul. 1, 2002, pp. 1-14.

Li et al., New Hope for Tumor Diagnosis—Detection of Circulating Free DNA, Chinese Journal of Clinical Pathologist, vol. 7, No. 2, Jun. 30, 2015, 14 pages.

Li et al., Size Separation of Circulatory DNA in Maternal Plasma Permits Ready Detection of Fetal DNA Polymorphisms, Clinical Chemistry, Molecular Diagnostics and Genetics, vol. 50, No. 6, Jun. 2004, pp. 1002-1011.

Liao et al., Targeted Massively Parallel Sequencing of Maternal Plasma DNA Permits Efficient and Unbiased Detection of Fetal Alleles, Clinical Chemistry, vol. 57, No. 1, Jan. 2011, pp. 92-101.

Lo et al., Digital PCR for the Molecular Detection of Fetal Chromosomal Aneuploidy, Proceedings of the National Academy of Sciences, vol. 104, No. 32, Aug. 7, 2007, pp. 13116-13121.

Lo et al., Maternal Plasma DNA Sequencing Reveals the Genome-Wide Genetic and Mutational Profile of the Fetus, Science Translation Medicine, vol. 2, No. 61, Dec. 8, 2010, pp. 1-13.

Lo et al., Quantitative Analysis of Cell-free Epstein-Barr Virus DNA in Plasma of Patients with Nasopharyngeal Carcinoma, Cancer Research, vol. 59, Mar. 1999, pp. 1188-1191.

Longo, Tumor Heterogeneity and Personalized Medicine, The New England Journal of Medicine, vol. 366, No. 10, Available Online at: www.nejm.org, Mar. 8, 2012, pp. 956-957.

Lun et al., Noninvasive Prenatal Diagnosis of Monogenic Diseases by Digital Size Selection and Relative Mutation Dosage on DNA in Maternal Plasma, Proceedings of the National Academy of Sciences of the United States of America, vol. 105, No. 50, Dec. 16, 2008, pp. 19920-19925.

McDermott et al., Genomics and the Continuum of Cancer Care, The New England Journal of Medicine, vol. 364, No. 4, Jan. 27, 2011, pp. 340-350.

Meyerson et al., Advances in Understanding Cancer Genomes Through Second-Generation Sequencing, Nature Reviews Genetics, vol. 11, No. 10, Oct. 2010, pp. 685-696.

Miller et al., Genome-Wide Molecular Characterization of Central Nervous System Primitive Neuroectodermal Tumor and Pineoblastoma, Neuro-Oncology, vol. 13, No. 8, Aug. 2011, pp. 866-879.

Mitchell et al., High Sensitivity and Specificity of Chromosomal Pertubations in Human Invasive Breast Cancer (BrCa) Associated with Circulating Nucleic Acids (CNA) Using Concatemers of Short Sequence DNA Tags in Next Generation Sequencing (NGS), Experimental Biology Meeting 2011, The FASEB Journal, vol. 25, No. 1, Apr. 9-13, 2011, 1 page.

Mouliere et al., High Fragmentation Characterizes Tumour-Derived Circulating DNA, PLOS One, vol. 6, No. 9, e23418, Sep. 6, 2011, pp. 1-10.

Muller et al., Identification of Loss of Heterozygosity on Circulating Free DNA in Peripheral Blood of Prostate Cancer Patients: Potential and Technical Improvements, Clinical Chemistry, vol. 54, No. 4, Apr. 1, 2008, pp. 688-696.

Murtaza et al., Non-Invasive Analysis of Acquired Resistance to Cancer Therapy by Sequencing of Plasma DNA, Nature, vol. 497, No. 7447, May 2, 2013, pp. 108-112.

Nannya et al., A Robust Algorithm for Copy Number Detection Using High-Density Oligonucleotide Single Nucleotide Polymorphism Genotyping Arrays, Cancer Research, vol. 65, No. 14, Jul. 15, 2005, pp. 6071-6079.

Palomaki et al., DNA Sequencing of Maternal Plasma to Detect Down Syndrome: An International Clinical Validation Study, Genetics in Medicine, vol. 13, No. 11, Nov. 2011, pp. 913-920.

International Application No. PCT/AU2011/001562, International Search Report and Written Opinion, mailed on Feb. 17, 2012, 8 pages.

International Application No. PCT/CN2016/073753, International Search Report and Written Opinion, mailed on May 10, 2016, 7 pages.

International Application No. PCT/CN2016/091531, International Preliminary Report on Patentability, mailed on Feb. 1, 2018, 5 pages.

International Application No. PCT/CN2016/091531, International Search Report and Written Opinion, mailed on Sep. 28, 2016, 11 pages.

International Application No. PCT/CN2018/074138, International Preliminary Report on Patentability, mailed on Jul. 30, 2019, 5 pages.

International Application No. PCT/CN2018/074138, International Search Report and Written Opinion, mailed on Apr. 28, 2018, 10 pages.

International Application No. PCT/CN2018/097072, International Preliminary Report on Patentability, mailed on Jan. 28, 2020, 4 pages.

International Application No. PCT/EP2010/066935, International Search Report and Written Opinion, mailed on Feb. 23, 2011, 10 pages.

International Application No. PCT/IB2013/000312, International Search Report and Written Opinion, mailed on Jun. 18, 2013, 13 pages.

International Application No. PCT/IB2013/054898, International Preliminary Report on Patentability, mailed on Dec. 31, 2014, 7 pages.

International Application No. PCT/IB2013/054898, International Search Report and Written Opinion, mailed on Dec. 23, 2013, 16 pages.

International Application No. PCT/US2010/055655, International Search Report and Written Opinion, mailed on Apr. 20, 2011, 20 pages.

International Application No. PCT/US2015/042310, International Search Report and Written Opinion, mailed on Jan. 12, 2016, 17 pages.

International Application No. PCT/US2017/058099, International Search Report and Written Opinion, mailed on Mar. 6, 2018, 20 pages.

(56) References Cited

OTHER PUBLICATIONS

Pennisi, Single-Cell Sequencing Tackles Basic and Biomedical Questions, Science, vol. 336, No. 6084, May 25, 2012, pp. 976-977.
Peter et al., Cell-Free DNA Fragmentation Patterns in Amniotic Fluid Identify Genetic Abnormalities and Changes Due to Storage, Diagnostic Molecular Pathology, vol. 17, No. 3, Sep. 2008, pp. 185-190.
Prokunina-Olsson et al., Cancer Sequencing Gets a Little More Personal, Available Online at: www.ScienceTranslationalMedicine.org, vol. 2, No. 20, Feb. 24, 2010, pp. 1-3.
Psifidi et al., Novel Quantitative Real-time LCR for the Sensitive Detection of SNP Frequencies in Pooled DNA: Method Development, Evaluation and Application, PLoS ONE, vol. 6, No. 1, e14560, Jan. 19, 2011, pp. 1-11.
Qin et al., Studying Copy Number Variations Using a Nanofluidic Platform, Nucleic Acids Research, vol. 36, No. 18, Oct. 2008, pp. 1-8.
Razavi et al., Many Cell-free DNA (CfDNA) Mutations are Derived from Clonal Hematopoiesis: Implications for Interpretation of Liquid Biopsy Tests, GRAIL-MSK WBC Poster, ASCO, vol. 35, No. 15, Available online at: https://grail.com/publication/many-cell-free-dna-cfdna-mutations-are-derived-fromclonal-hematopoiesis-implications-for-interpretation-of-liquid-biopsy-tests/>, Jun. 3, 2017, 41 pages.
Razavi et al., Performance of a High-Intensity 508-Gene Circulating-Tumor DNA (ctDNA) Assay in Patients With Metastatic Breast, Lung, and Prostate Cancer, GRAIL-MSK concordance Poster, ASCOM, vol. 35, No. 18, Available online at: https://grail.com/wpcontenUuploads/2018/05/ASC0_2017 Razavi_Concordance_POS_Final.pdf, Jun. 2017, 41 pages.
Reed et al., Non-Invasive Determination of the Paternal HLA Haplotype of a Fetus Using Kinetic PCR to Detect Fetal Microchimerism in Maternal Plasma, Bone Marrow Transplantation, vol. 29, No. 6, Mar. 2002, pp. 527-529.
Salani et al., Measurement of Cyclin E Genomic Copy Number and Strand Length in Cell-Free DNA Distinguish Malignant Versus Benign Effusions, Cancer Research, vol. 13, No. 19, Oct. 1, 2007, pp. 5805-5809.
Schwarzenbach et al., Cell-Free Nucleic Acids as Biomarkers in Cancer Patients, Nature Reviews Cancer, Advance Online Publication, vol. 11, No. 6, Jun. 2011, pp. 426-437.
Singapore Application No. 1201408113Q, Written Opinion, mailed on Aug. 16, 2017, 6 pages.
Singapore Application No. 11201408113Q, Written Opinion, mailed on Aug. 4, 2016, 7 pages.
Singapore Application No. 11201408113Q, Written Opinion, mailed on Dec. 8, 2015, 8 pages.
Singapore Application No. 11201706529T, Written Opinion, mailed on Jun. 19, 2018, 7 pages.
Shaw et al., Genomic Analysis of Circulating Cell-Free DNA Infers Breast Cancer Dormancy, Genome Research, vol. 22, No. 2, Feb. 2012, pp. 220-231.
Shoda et al., Clinical Utility of Circulating Cell-Free Epstein-Barr Virus DNA in Patients with Gastric Cancer, Oncotarget, vol. 8, No. 17, Apr. 25, 2017, pp. 28796-28804.
Shotelersuk et al., Epstein-Barr Virus DNA in Serum/Plasma as a Tumor Marker for Nasopharyngeal Cancer, Clinical Cancer Research, vol. 6, Mar. 31, 2000, pp. 1046-1051.
Snyder et al., Cell-Free DNA Comprises an in Vivo Nucleosome Footprint that Informs its Tissues-of-Origin, Cell, vol. 164, Jan. 14, 2016, pp. 57-68.
Snyder et al., Noninvasive Fetal Genome Sequencing: A Primer, NIH Public Access Author Manuscript in PMC, vol. 33, No. 6, Jun. 2013, pp. 547-554.
Snyder et al., Universal Noninvasive Detection of Solid Organ Transplant Rejection, Proceedings of the National Academy of Sciences, vol. 108, No. 15, Apr. 12, 2011, pp. 6229-6234.
Stratton, Exploring the Genomes of Cancer Cells: Progress and Promise, Science, vol. 331, No. 6024, Mar. 25, 2011, pp. 1553-1558.
Stratton et al., The Cancer Genome, Nature, vol. 458, No. 7239, Apr. 9, 2009, pp. 719-724.
Straver et al., Calculating the Fetal Fraction for Noninvasive Prenatal Testing Based on Genome-Wide Nucleosome Profiles, Prenatal Diagnosis, vol. 36, 2016, pp. 614-621.
Su et al., Inferring Combined CNV/SNP Haplotypes from Genotype Data, Bioinformatics, vol. 26, No. 11, Jun. 1, 2010, pp. 1437-1445.
Sun et al., Research Progress of Circulating DNA and Clinical Tumor, Medical Recapitulate, vol. 16, No. 9, May 31, 2010, pp. 1348-1350.
Taback et al., Prognostic Significance of Circulating Microsatellite Markers in the Plasma of Melanoma Patients, Cancer Research, vol. 61, Aug. 1, 2001, pp. 5723-5726.
Tan et al., Evaluation of Plasma Epstein-Barr Virus DNA Load as a Prognostic Marker for Nasopharyngeal Carcinoma, Singapore Medical Journal, vol. 47, No. 9, Sep. 2006, pp. 803-807.
Tao et al., Rapid Growth of a Hepatocellular Carcinoma and the Driving Mutations Revealed by Cell-Population Genetic Analysis of Whole-Genome Data, Proceedings of the National Academy of Sciences of the United States of America, vol. 108, No. 29, Jul. 19, 2011, pp. 12042-12047.
Thierry et al., Origin and Quantification of Circulating DNA in Mice with Human Colorectal Cancer Xenografts, Nucleic Acids Research, vol. 38, Issue 18, May 21, 2010, pp. 6159-6175.
Torchinsky et al., Sizing Femtogram Amounts of dsDNA by Single-Molecule Counting, Nucleic Acids Research, vol. 44, No. 2, e17, Sep. 13, 2015, 6 pages.
Tsang et al., Circulating Nucleic Acids in Plasma/Serum, Pathology, vol. 39, No. 2, Apr. 30, 2007, pp. 197-207.
Taiwan Application No. 102122036, Office Action, mailed on Feb. 8, 2017, 8 pages (4 pages of Original Document and 4 pages of English Translation).
Van Dijk et al., Library Preparation Methods for Next-Generation Sequencing: Tone Down the Bias, Experimental Cell Research, vol. 322, No. 1, Mar. 10, 2014, pp. 12-20.
Wagner, Free DNA—New Potential Analyte in Clinical Laboratory Diagnostics, Biochemia Medica, vol. 22, No. 1, Feb. 15, 2012, pp. 24-38.
Wang et al., Digital Karyotyping, Proceedings of the National Academy of Sciences U.S.A., vol. 99, No. 25, Dec. 10, 2002, pp. 16156-16161.
Weber et al., Detection of Human Tumor Cells by Amplicon Fusion Site Polymerase Chain Reaction (AFS-PCR), The Journal of Clinical Investigation, vol. 121, No. 2, Feb. 2011, pp. 545-553.
Welch et al., The Origin and Evolution of Mutations in Acute Myeloid Leukemia, Cell, vol. 150, No. 2, Jul. 20, 2012, pp. 264-278.
Xie et al., CNV-Seq, A New Method to Detect Copy Number Variation Using High-throughput Sequencing, BMC Bioinformatics, vol. 10, No. 80, Mar. 6, 2009, 9 pages.
Xu et al., Single-Cell Exome Sequencing Reveals Single-Nucleotide Mutation Characteristics of a Kidney Tumor, Cell, vol. 148, No. 5, Mar. 2, 2012, pp. 886-895.
Yap et al., Intratumor Heterogeneity: Seeing the Wood for the Trees, Science Translational Medicine, vol. 4, No. 127, Available online at: www.sciencetranslationalmedicine.org, Mar. 28, 2012, pp. 1-4.
Yu et al., Size-Based Molecular Diagnostics Using Plasma DNA for Noninvasive Prenatal Testing, Proceedings of the National Academy of Sciences, vol. 111, No. 23, Jun. 10, 2014, pp. 8583-8588.
Yung et al., Single-Molecule Detection of Epidermal Growth Factor Receptor Mutations in Plasma by Microfluidics Digital PCR in Non-Small Cell Lung Cancer Patients, Clinical Cancer Research, vol. 15, No. 6, Mar. 15, 2009, pp. 2076-2084.
Zhao et al., Homozygous Deletions and Chromosome Amplifications in Human Lung Carcinomas Revealed by Single Nucleotide Polymorphism Array Analysis, Cancer Research, vol. 65, No. 13, Jul. 1, 2005, pp. 5561-5570.
Zheng et al., Nonhematopoietically Derived DNA is Shorter than Hematopoietically Derived DNA in Plasma: A Transplantation Model, Clinical Chemistry, vol. 58, No. 3, Mar. 2012, pp. 549-558.
U.S. Appl. No. 16/858,018, Notice of Allowance mailed on Jul. 1, 2022, 8 pages.
Ambinder et al., Using CpG Methylation to Monitor EBV in Plasma, Annals of Oncology, vol. 25, No. 5, Oct. 2014, p. v24.

(56) References Cited

OTHER PUBLICATIONS

Australian Application No. 2018305609, First Examination Report mailed on Jul. 11, 2022, 4 pages.

Japanese Application No. 2020-503956, Office Action mailed on Jun. 7, 2022, 10 pages (4 pages of Original Document and 6 pages of English Translation).

Malaysia Application No. PI2019002339, Substantive Examination Adverse Report mailed on Sep. 29, 2022, 3 pages.

Malaysia Application No. PI2019003873, Substantive Examination Adverse Report mailed on Mar. 22, 2022, 5 pages.

Singapore Application No. 11201906397U, Further Written Opinion mailed on Aug. 19, 2022, 7 pages.

Shamay et al., CpG Methylation as a Tool to Characterize Cell-free Epstein-Barr Virus DNA, Infectious Agents and Cancer, vol. 7, No. 1, Apr. 19, 2012, pp. 1-2.

Sun et al., Size-Tagged Preferred Ends in Maternal Plasma DNA Shed Light on the Production Mechanism and Show Utility in Noninvasive Prenatal Testing, Proceedings of the National Academy of Sciences, vol. 115, No. 22, May 29, 2018, pp. E5106-E5114.

Taiwan Application No. 107102794, Office Action mailed on May 19, 2022, 10 pages (9 pages of Original Document and 1 pages of English Translation).

Taiwan Application No. 107125941, Office Action mailed on Jul. 15, 2022, 12 pages (7 pages of Original Document and 5 pages of English Translation).

Office Action dated Jul. 25, 2023 in IL Patent Application No. 272030. 4 pages.

Extended European Search Report dated Aug. 21, 2023 in EP Patent Application No. 23171661.4. 12 pages.

English translation of Office Action mailed Sep. 1, 2023 in CN Patent Application No. 201780080329.5. 11 pages.

Chinese Application No. 201780080329.5, Office Action mailed on Dec. 1, 2023, 18 pages. (8 pages of Original Document and 10 pages of English Translation).

Philippines Application No. 1-2020-500156, Office Action mailed on Nov. 7, 2023, 6 pages. (1 pages of Original Document and 1 pages of English Translation).

English translation of Office Action mailed Apr. 4, 2023 in JP Patent Application No. 2020-503956. 8 pages.

Mrozek-Gorska, Paulina et al.; "Epstein-Barr virus reprograms human B lymphocytes immediately in the prelatent phase of infection"; PNAS; 2019; vol. 116, No. 32; https://www.pnas.org/doi/full/10.1073/pnas.1901314116; pp. 16046-16055.

Examination Report No. 1 dated May 31, 2023 in AU Patent Application No. 2017347790. 4 pages.

Canadian Application No. 3,070,898, Office Action mailed on Feb. 29, 2024, 5 pages.

Clarke et al., Human Papillomavirus DNA Methylation as a Potential Biomarker for Cervical Cancer, Cancer Epidemiology, Biomarkers & Prevention, vol. 21, No. 12, Dec. 2012, pp. 2125-2137.

Ji et al., Evaluation of Plasma Epstein-Barr Virus DNA Load to Distinguish Nasopharyngeal Carcinoma Patients From Healthy High-Risk Populations in Southern China, Cancer, vol. 120, No. 9, May 1, 2014, pp. 1353-1360.

Kwok et al., From Conventional to Next Generation Sequencing of Epstein-Barr Virus Genomes, Viruses, vol. 8, No. 3, Feb. 24, 2016, pp. 1-15.

Malaysian Application No. PI2020000327, Substantive Examination Adverse Report mailed on Feb. 16, 2024, 4 pages.

English translation of Office Action and Search Report mailed Mar. 20, 2024 in TW Patent Application No. 112116081. 5 pages.

English translation of Office Action mailed Aug. 6, 2024 in JP Patent Application No. 2023-126899. 7 pages.

Office Action dated Oct. 9, 2024 in CA Patent Application No. 3,041,647. 5 pages.

Examination Report No. 1 dated Oct. 10, 2024 in AU Patent Application No. 2023202318. 4 pages.

\* cited by examiner

| | 101 | 102 | 103 | 104 |
|---|---|---|---|---|
| | | Chromosomes | Sizes of capturing regions (bp) | Probe tiling fold |
| Autosomes | | chr1 | 2018178 | 5x tiling capturing probes |
| | | chr2 | 959395 | |
| | | chr3 | 1143882 | |
| | | chr4 | 1035300 | |
| | | chr5 | 464688 | |
| | | chr6 | 693162 | |
| | | chr7 | 696688 | |
| | | chr8 | 889727 | |
| | | chr9 | 1257194 | |
| | | chr10 | 383650 | |
| | | chr11 | 1410412 | |
| | | chr12 | 1463254 | |
| | | chr13 | 570007 | |
| | | chr14 | 213784 | |
| | | chr15 | 468290 | |
| | | chr16 | 1115989 | |
| | | chr17 | 843909 | |
| | | chr18 | 971357 | |
| | | chr19 | 1157954 | |
| | | chr20 | 1028902 | |
| | | chr21 | 806977 | |
| | | chr22 | 878150 | |
| Viral targets | | EBV | 171326 | 200x tiling capturing probes |
| | | HBV | 2741 | |
| | | HPV16 | 7902 | |
| | | HPV18 | 7847 | |
| | | HPV31 | 7902 | |
| | | HPV33 | 7899 | |
| | | HPV35 | 7837 | |
| | | HPV39 | 7823 | |
| | | HPV45 | 7841 | |
| | | HPV51 | 7809 | |
| | | HPV52 | 7905 | |
| | | HPV56 | 7817 | |
| | | HPV58 | 7819 | |
| | | HPV66 | 7815 | |
| | | HPV68 | 7836 | |
| | | HPV70 | 7895 | |

FIG. 1

| 1001 Virus genome | 1002 start | 1003 end | Methylation density (%) 1004 ||
|---|---|---|---|---|
| | | | Infectious mononucleosis (TBR1610) | NPC (TBR1392) |
| EBV | 10000 | 10500 | 7.5 | 88.7 |
| EBV | 10500 | 11000 | 0.6 | 91.3 |
| EBV | 11000 | 11500 | 3.5 | 87.7 |
| EBV | 114500 | 115000 | 42.7 | 87.1 |
| EBV | 11500 | 12000 | 0.3 | 91.3 |
| EBV | 115000 | 115500 | 31.0 | 82.6 |
| EBV | 12000 | 12500 | 19.5 | 86.6 |
| EBV | 137000 | 137500 | 42.0 | 83.5 |
| EBV | 137500 | 138000 | 39.4 | 91.7 |
| EBV | 139000 | 139500 | 29.3 | 87.6 |
| EBV | 139500 | 140000 | 46.0 | 92.6 |
| EBV | 140000 | 140500 | 24.4 | 90.0 |
| EBV | 140500 | 141000 | 47.2 | 90.6 |
| EBV | 143000 | 143500 | 37.2 | 91.0 |
| EBV | 143500 | 144000 | 13.8 | 90.2 |
| EBV | 165000 | 165500 | 35.7 | 83.0 |
| EBV | 168000 | 168500 | 42.7 | 86.5 |
| EBV | 36500 | 37000 | 39.6 | 90.0 |
| EBV | 37000 | 37500 | 36.7 | 82.9 |
| EBV | 37500 | 38000 | 39.1 | 86.8 |
| EBV | 38000 | 38500 | 36.6 | 89.9 |
| EBV | 39500 | 40000 | 17.8 | 80.2 |
| EBV | 40000 | 40500 | 28.7 | 80.9 |
| EBV | 41000 | 41500 | 37.6 | 83.5 |
| EBV | 41500 | 42000 | 35.1 | 89.4 |
| EBV | 42500 | 43000 | 45.6 | 81.6 |
| EBV | 43000 | 43500 | 48.0 | 86.9 |
| EBV | 45000 | 45500 | 48.5 | 81.4 |
| EBV | 51000 | 51500 | 38.2 | 86.0 |
| EBV | 51500 | 52000 | 50.0 | 89.0 |
| EBV | 58000 | 58500 | 48.4 | 88.3 |
| EBV | 59500 | 60000 | 49.4 | 88.6 |
| EBV | 61000 | 61500 | 43.0 | 88.3 |
| EBV | 63500 | 64000 | 48.0 | 86.6 |
| EBV | 73500 | 74000 | 48.6 | 87.0 |
| EBV | 79500 | 80000 | 48.4 | 82.1 |
| EBV | 82000 | 82500 | 48.4 | 85.2 |
| EBV | 84500 | 85000 | 49.5 | 82.4 |
| EBV | 9500 | 10000 | 23.9 | 88.3 |

*FIG. 10*

| Type | Sample | Stage |
|---|---|---|
| HNSCC | TBR1245 | I |
| HNSCC | TBR1988 | I |
| HNSCC | TBR1989 | II |
| HNSCC | TBR2002 | I |
| HNSCC | TBR2175 | II |

FIG. 29

ENHANCEMENT OF CANCER SCREENING USING CELL-FREE VIRAL NUCLEIC ACIDS

CROSS-REFERENCES TO RELATED APPLICATIONS

The present application is a continuation application of U.S. patent application Ser. No. 16/046,795, entitled "ENHANCEMENT OF CANCER SCREENING USING CELL-FREE VIRAL NUCLEIC ACIDS" filed Jul. 26, 2018, which claims priority from and is a non-provisional of U.S. Provisional Application No. 62/537,328, entitled "Enhancement Of Cancer Screening Using Cell-Free Viral Nucleic Acids" filed Jul. 26, 2017, the entire contents of which are herein incorporated by reference for all purposes.

BACKGROUND

The discovery that tumor cells release tumor-derived DNA into the blood stream has sparked the development of non-invasive methods capable of determining the presence, location and/or type of tumor in a subject using cell-free samples (e.g., plasma). Many tumors can be treatable if detected early in their development. However, current methods can lack the sensitivity and/or specificity to detect a tumor at an early stage and can return a large number of false positive or false negative results. For example, certain viruses are associated with cancer, but viral DNA can be detected in subjects that do not have cancer, thereby causing false positive results.

The sensitivity of a test can refer to the likelihood that a subject that is positive for a condition tests positive for the condition. The specificity of a test can refer to the likelihood that a subject that is negative for a condition tests negative for that condition. The problems of sensitivity and specificity can be exaggerated in assays for the early detection of tumors, e.g., because samples on which such tumor detection methods are performed can have relatively small amounts of tumor-derived DNA and because the condition itself can have a relatively low prevalence among individuals tested in the early stage. Accordingly, there is a clinical need for methods having higher sensitivity and/or specificity for the detection of tumors.

SUMMARY

Embodiments provide systems, apparatuses, and methods for analyzing a biological sample of a subject, e.g., in the animal kingdom, such as a human. Cell-free DNA molecules in a mixture of the biological sample can be analyzed to detect viral DNA, e.g., by determining a location in a particular viral genome. A methylation status of the viral DNA at one or more sites in the viral genome can be determined. Mixture methylation level(s) can be measured based on one or more amounts of the plurality of cell-free DNA molecules methylated at a set of site(s) of the particular viral genome. The mixture methylation level(s) can be determined in various ways, e.g., as a percentage/density of cell-free DNA molecules that are methylated at a particular site or across multiple sites, and potentially across multiple regions, each including one or more sites.

The mixture methylation level(s) can be compared to reference methylation level(s), e.g., determined from at least two cohorts of other subjects. The cohorts can have different classifications (including the first condition) associated with the particular viral genome. Other cohort(s) can correspond to other condition(s). The comparison can be performed in a variety of ways, e.g., by forming a multidimensional point of N methylation levels and determining differences from N reference methylation levels. A first classification of whether the subject has the first condition can be determined based on the comparing.

These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the design of capture probes for targeted bisulfite sequencing according to embodiments of the present disclosure.

FIG. 10 is a table listing the genomic coordinates of the differentially methylated regions fulfilling the criteria described in FIG. 9.

FIG. 29 shows the clinical stage of the 5 cases of HPV positive-head and neck squamous cell carcinoma (HPV+ve HNSCC).

Figure 2:
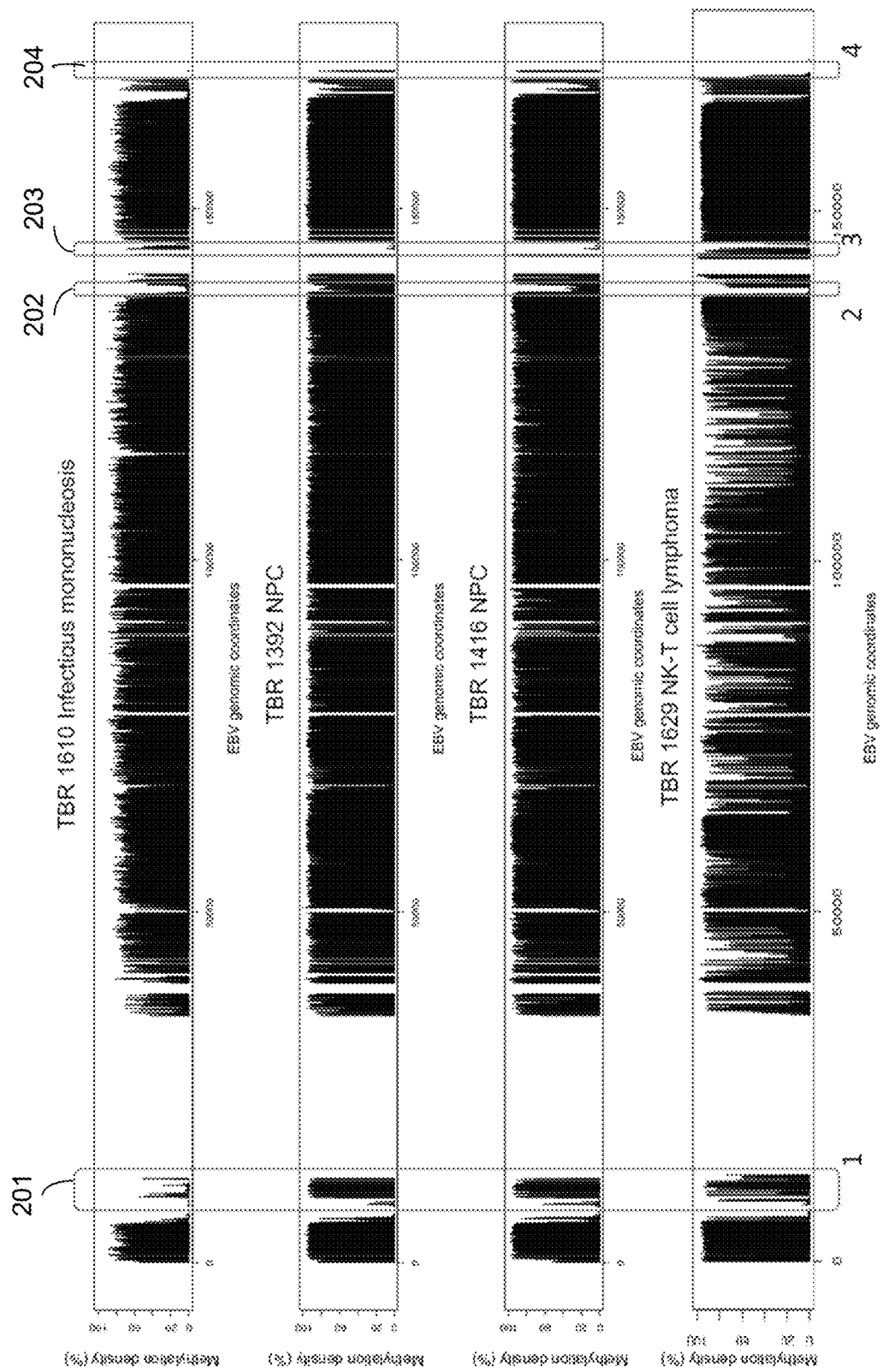
FIG. 2 shows the methylation densities of CpG sites across the Epstein-Barr virus (EBV) genome in patients with infectious mononucleosis, nasopharyngeal carcinoma (NPC) and Natural killer (NK)-T cell lymphoma according to embodiments of the present disclosure.

Appendix A shows the list of individual CpG sites across the EBV genome with differential methylation levels, when the differences in the methylation percentages over these CpG sites between the pooled sequencing data of 3 subjects with persistently positive EBV DNA and the 3 patients with NPC are greater than 20%. Those sites marked with * have a difference in methylation percentages greater than 40%,  have a difference greater than 60%, and * have a difference greater than 80%.

Terms

The term "sample", "biological sample" or "patient sample" is meant to include any tissue or material derived from a living or dead subject. A biological sample may be a cell-free sample, which may include a mixture of nucleic acid molecules from the subject and potentially nucleic acid molecules from a pathogen, e.g., a virus. A biological sample generally comprises a nucleic acid (e.g., DNA or RNA) or a fragment thereof. The term "nucleic acid" may generally refer to deoxyribonucleic acid (DNA), ribonucleic acid (RNA) or any hybrid or fragment thereof. The nucleic acid in the sample may be a cell-free nucleic acid. A sample may be a liquid sample or a solid sample (e.g., a cell or tissue sample). The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). The centrifugation protocol can include, for example, 3,000 g×10 minutes, obtaining the fluid part, and re-centrifuging at, for example, 30,000 g for another 10 minutes to remove residual cells.

The term "fragment" (e.g., a DNA fragment), as used herein, can refer to a portion of a polynucleotide or polypeptide sequence that comprises at least 3 consecutive nucleotides. A nucleic acid fragment can retain the biological activity and/or some characteristics of the parent polypeptide. A nucleic acid fragment can be double-stranded or single-stranded, methylated or unmethylated, intact or nicked, complexed or not complexed with other macromolecules, e.g. lipid particles, proteins. In an example, nasopharyngeal cancer cells can release fragments of Epstein-Barr Virus (EBV) DNA into the blood stream of a subject, e.g., a patient. These fragments can comprise one or more BamHI-W sequence fragments, which can be used to detect the level of tumor-derived DNA in the plasma. The BamHI-W sequence fragment corresponds to a sequence that can be recognized and/or digested using the Bam-HI restriction enzyme. The BamHI-W sequence can refer to the sequence 5'-GGATCC-3'.

A tumor-derived nucleic acid can refer to any nucleic acid released from a tumor cell, including pathogen nucleic acids from pathogens in a tumor cell. For example, Epstein-Barr virus (EBV) DNA can be released from a cancer cell of a subject with nasopharyngeal carcinoma (NPC).

The term "assay" generally refers to a technique for determining a property of a nucleic acid. An assay (e.g., a first assay or a second assay) generally refers to a technique for determining the quantity of nucleic acids in a sample, genomic identity of nucleic acids in a sample, the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art may be used to detect any of the properties of nucleic acids mentioned herein. Properties of nucleic acids include a sequence, quantity, genomic identity, copy number, a methylation state at one or more nucleotide positions, a size of the nucleic acid, a mutation in the nucleic acid at one or more nucleotide positions, and the pattern of fragmentation of a nucleic acid (e.g., the nucleotide position(s) at which a nucleic acid fragments). The term "assay" may be used interchangeably with the term "method". An assay or method can have a particular sensitivity and/or specificity, and their relative usefulness as a diagnostic tool can be measured using ROC-AUC statistics.

The term "random sequencing," as used herein, generally refers to sequencing whereby the nucleic acid fragments sequenced have not been specifically identified or predetermined before the sequencing procedure. Sequence-specific primers to target specific gene loci are not required. In some embodiments, adapters are added to the end of a fragment, and the primers for sequencing attached to the adapters. Thus, any fragment can be sequenced with the same primer that attaches to a same universal adapter, and thus the sequencing can be random. Massively parallel sequencing may be performed using random sequencing.

A "sequence read" generally refers to a string of nucleotides sequenced from any part or all of a nucleic acid molecule. For example, a sequence read may be a short string of nucleotides (e.g., 20-150 bases) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification, or based on biophysical measurements, such as mass spectrometry.

A "methylome" provides a measure of an amount of DNA methylation at a plurality of sites or loci in a genome (e.g., a human or other animal genome or a viral genome). The methylome may correspond to all of the genome, a substantial part of the genome, or relatively small portion(s) of the genome. Examples of methylomes of interest are the methylomes of tumor cells (e.g. nasopharyngeal carcinoma, hepatocellular carcinoma, cervical carcinoma), viral methylomes (e.g., of EBV resident within healthy or tumor cells of a subject); bacterial methylomes, and organs (e.g. methylomes of brain cells, bones, the lungs, the heart, the muscles and the kidneys, etc.) that can contribute DNA into a bodily fluid (e.g. plasma, serum, sweat, saliva, urine, genital secretions, semen, stools fluid, diarrheal fluid, cerebrospinal fluid, secretions of the gastrointestinal tract, ascitic fluid, pleural fluid, intraocular fluid, fluid from a hydrocele (e.g. of the testis), fluid from a cyst, pancreatic secretions, intestinal secretions, sputum, tears, aspiration fluids from breast and thyroid, etc.). The organs may be transplanted organs. The methylome of a fetus is another example.

A "plasma methylome" is a methylome determined from the plasma or serum of an animal (e.g., a human). The plasma methylome is an example of a cell-free methylome since plasma and serum include cell-free DNA. The plasma methylome is also an example of a mixed methylome since it is a mixture of fetal/maternal methylome, tumor/patient methylome, DNA derived from different tissues or organs, donor/recipient methylome in the context or organ transplantation, and/or mixture of DNA from different genomes (e.g., animal genome and bacterial/viral genomes).

A "site" (also called a "genomic site") corresponds to a single site, which may be a single base position or a group of correlated base positions, e.g., a CpG site or larger group of correlated base positions. A "locus" may correspond to a region that includes multiple sites. A locus can include just one site, which would make the locus equivalent to a site in that context.

The "methylation index" for each genomic site (e.g., a CpG site) can refer to the proportion of DNA fragments (e.g., as determined from sequence reads or probes) showing methylation at the site over the total number of reads covering that site. A "read" can correspond to information (e.g., methylation status at a site) obtained from a DNA fragment. A read can be obtained using reagents (e.g. primers or probes) that preferentially hybridize to DNA fragments of a particular methylation status. Typically, such reagents are applied after treatment with a process that differentially modifies or differentially recognizes DNA molecules depending of their methylation status, e.g. bisulfite conversion, or methylation-sensitive restriction enzyme, or methylation binding proteins, or anti-methylcytosine antibodies. In another embodiment, single molecule sequencing techniques that recognize methylcytosines and hydroxymethylcytosines can be used for elucidating the methylation status and for determining a methylation index.

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer to the number of cytosine sites, "C's", that are shown to be methylated (for example unconverted after bisulfite conversion) over the total number of analyzed cytosine residues, i.e. including cytosines outside of the CpG context, in the region. The methylation index, methylation density, and proportion of methylated cytosines are examples of "methylation levels," which may include other ratios involving counts of methylated reads at sites. Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci 2013; 110: 18910-18915) and by the Pacific Biosciences single molecule real time analysis (Flusberg et al. Nat Methods 2010; 7: 461-465)).

A "methylation profile" (also called methylation status) includes information related to DNA methylation for a region. Information related to DNA methylation can include, but not limited to, a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part (e.g., covering more than 10%, 20%, 30%, 40%, 50%, 60%, 70%, 80%, or 90%) of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as $N^6$-methyladenine, has also been reported.

"Methylation-aware sequencing" refers to any sequencing method that allows one to ascertain the methylation status of a DNA molecule during a sequencing process, including, but not limited to bisulfite sequencing, or sequencing preceded by methylation-sensitive restriction enzyme digestion, immunoprecipitation using anti-methylcytosine antibody or methylation binding protein, or single molecule sequencing that allows elucidation of the methylation status. A "methylation-aware assay" or "methylation-sensitive assay" can include both sequencing and non-sequencing based methods, such as MSP, probe based interrogation, hybridization, restriction enzyme digestion followed by density measurements, anti-methylcytosine immunoassays, mass spectrometry interrogation of proportion of methylated cytosines or hydroxymethylcytosines, immunoprecipitation not followed by sequencing, etc.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (host vs. virus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" may be used to refer to a tissue from which a cell-free nucleic acid originates. In one example, viral nucleic acid fragments may be derived from blood tissue, e.g., for Epstein-Barr Virus (EBV). In another example, viral nucleic acid fragments may be derived from tumor tissue, e.g., EBV or Human papillomavirus infection (HPV).

A "separation value" (or relative abundance) corresponds to a difference or a ratio involving two values, e.g., two amounts of DNA molecules, two fractional contributions, or two methylation levels, such as a sample (mixture) methylation level and a reference methylation level. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms ($ln$) of the two values. A separation value can include a difference and/or a ratio. A methylation level is an example of a relative abundance, e.g., between methylated DNA molecules (e.g., at particular sites) and other DNA molecules (e.g., all other DNA molecules at particular sites or just unmethylated DNA molecules). The amount of other DNA molecules can act as a normalization factor. As another example, an intensity of methylated DNA molecules (e.g., fluorescent or electrical intensity) relative to intensity of all or unmethylated DNA molecules can be determined. The relative abundance can also include an intensity per volume.

The term "classification" as used herein refers to any number(s) or other characters(s) that are associated with a particular property of a sample. For example, a "+" symbol (or the word "positive") could signify that a sample is classified as having a particular level of a condition (e.g., cancer). The classification can be binary (e.g., positive or negative) or have more levels of classification (e.g., a scale from 1 to 10 or 0 to 1).

The terms "cutoff" "threshold," or reference level can refer to a predetermined number used in an operation. A threshold or reference value may be a value above or below which a particular classification applies, e.g., a classification of a condition, such as whether a subject has a condition or a severity of the condition. A cutoff may be predetermined with or without reference to the characteristics of the sample or the subject. For example, cutoffs may be chosen based on the age or sex of the tested subject. A cutoff may be chosen after and based on output of the test data. For example, certain cutoffs may be used when the sequencing of a sample reaches a certain depth. As another example, reference subjects with known classifications of one or more conditions and measured characteristic values (e.g., a methylation level) can be used to determine reference levels to discriminate between the different conditions and/or classifications of a condition (e.g., whether the subject has the condition). Any of these terms can be used in any of these contexts.

The terms "control", "control sample", "reference", "reference sample", "normal", and "normal sample" may be interchangeably used to generally describe a sample that does not have a particular condition, or is otherwise healthy. In an example, a method as disclosed herein may be performed on a subject having a tumor, where the reference sample is a sample taken from a healthy tissue of the subject. In another example, the reference sample is a sample taken from a subject with the disease, e.g. cancer or a particular stage of cancer. A reference sample may be obtained from the subject, or from a database. The reference generally refers to a reference genome that is used to map sequence reads obtained from sequencing a sample from the subject. A reference genome generally refers to a haploid or diploid genome to which sequence reads from the biological sample and the constitutional sample can be aligned and compared. For a haploid genome, there is only one nucleotide at each locus. For a diploid genome, heterozygous loci can be identified, with such a locus having two alleles, where either allele can allow a match for alignment to the locus. A reference genome may correspond to a virus, e.g., by including one or more viral genomes.

The phrase "healthy," as used herein, generally refers to a subject possessing good health. Such a subject demonstrates an absence of any malignant or non-malignant disease. A "healthy individual" may have other diseases or conditions, unrelated to the condition being assayed, that may normally not be considered "healthy".

The terms "cancer" or "tumor" may be used interchangeably and generally refer to an abnormal mass of tissue wherein the growth of the mass surpasses and is not coordinated with the growth of normal tissue. A cancer or tumor may be defined as "benign" or "malignant" depending on the following characteristics: degree of cellular differentiation including morphology and functionality, rate of growth, local invasion, and metastasis. A "benign" tumor is generally well differentiated, has characteristically slower growth than a malignant tumor, and remains localized to the site of origin. In addition, a benign tumor does not have the capacity to infiltrate, invade, or metastasize to distant sites. A "malignant" tumor is generally poorly differentiated (anaplasia), has characteristically rapid growth accompanied by progressive infiltration, invasion, and destruction of the surrounding tissue. Furthermore, a malignant tumor has the capacity to metastasize to distant sites. "Stage" can be used to describe how advance a malignant tumor is. Early stage cancer or malignancy is associated with less tumor burden in the body, generally with less symptoms, with better prognosis, and with better treatment outcome than a late stage malignancy. Late or advanced stage cancer or malignancy is often associated with distant metastases and/or lymphatic spread.

The term "level of cancer" (or more generally "level of disease" or "level of condition") can refer to whether cancer exists (i.e., presence or absence), a stage of a cancer, a size of tumor, whether there is metastasis, the total tumor burden of the body, the cancer's response to treatment, and/or other measure of a severity of a cancer (e.g. recurrence of cancer). The level of cancer may be a number or other indicia, such as symbols, alphabet letters, and colors. The level may be zero. The level of cancer may also include premalignant or precancerous conditions (states). The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can mean 'screening' or can mean checking if someone, with suggestive features of cancer (e.g. symptoms or other positive tests), has cancer. A "level of pathology" can refer to level of pathology associated with a pathogen, where the level can be as described above for cancer. The level of diseases/condition can also be as described above for cancer. When the cancer is associated with a pathogen, a level of cancer can be a type of a level of pathology.

The terms "size profile" and "size distribution" generally relate to the sizes of DNA fragments in a biological sample. A size profile may be a histogram that provides a distribution of an amount of DNA fragments at a variety of sizes. Various statistical parameters (also referred to as size parameters or just parameter) can distinguish one size profile to another. One parameter is the percentage of DNA fragment of a particular size or range of sizes relative to all DNA fragments or relative to DNA fragments of another size or range.

The term "false positive" (FP) can refer to subjects not having a condition. False positive generally refers to subjects not having a tumor, a cancer, a pre-cancerous condition (e.g., a precancerous lesion), a localized or a metastasized cancer, a non-malignant disease, or are otherwise healthy. The term false positive generally refers to subjects not having a condition, but are identified as having the condition by an assay or method of the present disclosure.

The terms "sensitivity" or "true positive rate" (TPR) can refer to the number of true positives divided by the sum of the number of true positives and false negatives. Sensitivity may characterize the ability of an assay or method to correctly identify a proportion of the population that truly has a condition. For example, sensitivity may characterize the ability of a method to correctly identify the number of subjects within a population having cancer. In another example, sensitivity may characterize the ability of a method to correctly identify one or more markers indicative of cancer.

The terms "specificity" or "true negative rate" (TNR) can refer to the number of true negatives divided by the sum of the number of true negatives and false positives. Specificity may characterize the ability of an assay or method to correctly identify a proportion of the population that truly does not have a condition. For example, specificity may characterize the ability of a method to correctly identify the number of subjects within a population not having cancer. In another example, specificity may characterize the ability of a method to correctly identify one or more markers indicative of cancer.

The term "ROC" or "ROC curve" can refer to the receiver operator characteristic curve. The ROC curve can be a graphical representation of the performance of a binary classifier system. For any given method, an ROC curve may be generated by plotting the sensitivity against the specificity at various threshold settings. The sensitivity and specificity of a method for detecting the presence of a tumor in a subject may be determined at various concentrations of tumor-derived nucleic acid in the plasma sample of the subject. Furthermore, provided at least one of the three parameters (e.g., sensitivity, specificity, and the threshold setting), and ROC curve may determine the value or expected value for any unknown parameter. The unknown parameter may be determined using a curve fitted to the ROC curve. The term "AUC" or "ROC-AUC" generally refers to the area under a receiver operator characteristic curve. This metric can provide a measure of diagnostic utility of a method, taking into account both the sensitivity and specificity of the method. Generally, ROC-AUC ranges from 0.5 to 1.0, where a value closer to 0.5 indicates the method has limited diagnostic utility (e.g., lower sensitivity and/or specificity) and a value closer to 1.0 indicates the method has greater diagnostic utility (e.g., higher sensitivity and/or specificity). See, e.g., Pepe et al, "Limitations of the Odds Ratio in Gauging the Performance of a Diagnostic, Prognostic, or Screening Marker," Am. J. Epidemiol 2004, 159 (9): 882-890, which is entirely incorporated herein by reference. Additional approaches for characterizing diagnostic utility using likelihood functions, odds ratios, information theory, predictive values, calibration (including goodness-of-fit), and reclassification measurements are summarized according to Cook, "Use and Misuse of the Receiver Operating Characteristic Curve in Risk Prediction," Circulation 2007, 115: 928-935, which is entirely incorporated herein by reference.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

The terminology used herein is for the purpose of describing particular cases only and is not intended to be limiting. As used herein, the singular forms "a", "an" and "the" are intended to include the plural forms as well, unless the context clearly indicates otherwise. The use of "or" is intended to mean an "inclusive or," and not an "exclusive or" unless specifically indicated to the contrary. The term "based on" is intended to mean "based at least in part on." Furthermore, to the extent that the terms "including", "includes", "having", "has", "with", or variants thereof are used in either the detailed description and/or the claims, such terms are intended to be inclusive in a manner similar to the term "comprising."

DETAILED DESCRIPTION

In the present disclosure, we describe an approach to differentiate among different EBV-associated diseases, malignancies, states or completely healthy individuals based on the analysis of methylation patterns of circulating EBV DNA fragments in blood. There are a number of applications or utilities for the analysis of methylation patterns of cell-free EBV DNA molecules. The feasibility of methylation analysis of cell-free viral molecules in a noninvasive manner would enhance the clinical applications in the context of screening, predictive medicine, risk stratification, surveillance and prognostication.

Embodiments can differentiate subjects with different virus-associated conditions (e.g., patients with NPC) and apparently healthy subjects with detectable plasma EBV DNA, with even a single time-point analysis, e.g., from a single blood draw. Embodiments can also be used for screening or detecting if a subject has a disease or cancer, for disease monitoring in a cancer patient, for prognostication and for disease or cancer risk prediction (i.e., for predicting if a subject may develop a disease or cancer in the future). This approach can also be generalized to viruses other than EBV. This approach is thus a general approach for identifying viral DNA-based biomarkers.

I. Cancer and Viruses

Both DNA and RNA viruses have been shown to be capable of causing cancer in humans. In some embodiments, a subject may have a cancer caused by a virus (e.g., an oncovirus). In some embodiments, a subject may have a cancer, and the cancer may be detectable using viral DNA. For analysis of RNA, the nucleic acids would exist as complementary DNA (cDNA), which is copied from the RNA and is the medium for replication in the host cells. These cDNA could have methylation and be used in embodiments.

Various viral infections are associated with various cancers or other pathological conditions. For example, EBV infection is closely associated with NPC and natural killer (NK) T-cell lymphoma, Hodgkin lymphoma, gastric cancer, and infectious mononucleosis. Hepatitis B virus (HBV) infection and hepatitis C virus (HCV) infection are associated with increased risks of developing hepatocellular carcinoma (HCC). Human papillomavirus infection (HPV) are associated with increased risks of developing cervical cancer (CC) and head and neck squamous cell carcinoma (HN-SCC). Although examples focus more on EBV, techniques are equally applicable for cancer and other conditions relating to HPV, HBV, and other viruses, particularly those associated with cancer.

A. EBV

It has been estimated that 95% of the world's population have an asymptomatic lifelong Epstein-Barr virus (EBV) infection, whereby the virus remains latent in the memory B cells of healthy individuals and persists in the body (Young et al. Nat Rev Cancer 2016 16(12):789-802). A small proportion of subjects develop a symptomatic infection, presenting as infectious mononucleosis with the viral infection. EBV is also regarded as an oncogenic virus for its association with a number of malignancies or cancer-like syndromes of epithelial and hematological origins, including nasopharyngeal carcinoma (NPC), gastric carcinoma, Burkitt's lymphoma, Hodgkin's lymphoma, natural killer-T cell (NK-T cell) lymphoma and post-transplant lymphoproliferative disorder (PTLD).

Circulating EBV DNA has been explored for its diagnostic and prognostic role in patients with EBV-associated malignancies. In this regard, plasma EBV DNA has been established as a biomarker of NPC (Lo et al. Cancer Res 1999; 59:1188-91). Regular surveillance with plasma EBV DNA is recommended for patients with a confirmed diagnosis of NPC for detection of residual disease and recurrence (Lo et al. Cancer Res 1999; 59:5452-5, Chan et al. J Natl Cancer Inst 2002; 94:1614-9, Leung et al. Cancer 2003, 98(2), 288-91 & Leung et al. Ann Oncol 2014; 25(6):1204-8). Plasma EBV DNA has also been shown to have prognostic significance in other EBV-associated malignancies, including Hodgkin's lymphoma (Kanakry et al. Blood 2013; 121(18): 3547-3553), extranodal NK-T cell lymphoma (Wang et al. Oncotarget 2015; 6(30):30317-26, Kwong et al. Leukemia 2014; 28(4):865-870) and PTLD (Gulley and Tang. Clin Microbiol Rev 2010; 23(2): 350-66).

However, not all subjects that have such an infection will get an associated cancer. The source of the plasma EBV DNA must be different in persons without NPC. Unlike the persistent release of EBV DNA into the circulation from NPC cells, the source of EBV DNA only contributes such DNA transiently in the persons without NPC B. False Positives In the context of cancer screening, we have recently conducted a large-scale prospective study on NPC screening using plasma EBV DNA analysis by quantitative PCR (qPCR) (Chan et al. N Engl J Med 2017; 377:513-522). We analyzed the plasma EBV DNA level in all recruited subjects (screening cohort) who were asymptomatic for NPC upon enrollment. Subjects with detectable amount of plasma EBV DNA were retested for EBV DNA at 4 weeks after the initial test. Among 20,174 subjects recruited, 1,112 had detectable plasma EBV DNA on their first test. There were 309 subjects who were persistently positive on the follow-up test based on a measure of an amount of plasma EBV DNA. Subsequently, 34 subjects with persistently positive plasma EBV DNA results were confirmed to have NPC by endoscopy and magnetic resonance imaging (MM). As mentioned, plasma EBV DNA could be detected in apparently healthy individuals without NPC or other EBV-associated malignancies.

In the 20,174 subjects undergone NPC screening, the false plasma EBV DNA positive rate was approximately 5% based on single time-point analysis ((1112−34)/(20174−34) =5.3%). The false positive rate was lowered to 1.5% with serial EBV DNA analysis on two occasions. However, the sequential testing of plasma EBV DNA requires the collection of an additional blood sample from subjects with initial positive results, which can present logistical challenges. Also, a substantial proportion of subjects who have positive plasma EBV DNA results do not have NPC (96% of subjects showing positive results on single time-point analysis do not have NPC, determined as (1112−34)/1112). Subjects with false positive results would need serial assessment and unnecessary investigations including endoscopy and Mill for definitive diagnosis. All these would lead to patient anxiety and higher follow-up costs. Therefore, we aim to distinguish patients with NPC from subjects with false positive plasma EBV DNA results with a single time-point blood analysis. In this example, a false plasma EBV DNA positive rate can be considered a non-NPC positive rate or also referred to as a one-time positive rate.

C. Use of Methylation

Previous studies have described different types of viral latency (Types 0, I, II and III), which are defined by latency-associated viral gene transcription patterns, found in different EBV-associated malignancies (Young et al. Nat Rev Cancer 2016; 16(12):789-802). Viral latency is defined by the latency-associated gene transcription patterns. Therefore, viruses in different types of viral latency have different patterns of viral gene transcription. Different EBV-associated diseases or conditions with the same type of viral latency can have similar viral gene transcription patterns.

Among the different types of latency, there are different viral gene expression profiles and different methylation status of different viral gene promoters, including the origin of replication, C-promoter, W-promoter, Q-promoter and LMP1/2 promoters (Woeller et al. Curr Opin Virol 2013; 3(3):260-5). It has been suggested that DNA methylation contributes to regulate the gene expression and that there are latency-specific methylation patterns (Lieberman. Nat Rev Microbiol 2013; 11(12):863-75). In one example, a previous study found a methylated state of C promoter, which is compatible with latency type II-specific methylation pattern, in EBV DNA from nasopharyngeal brush cytology samples of patients with NPC using methylation-specific PCR (Ramayanti et al. 2017 Int J Cancer 140, 149-162). However, different EBV-associated diseases or conditions may have the same type of viral latency and would therefore have similar viral gene transcription patterns (examples described in the next paragraph). Thus, viral latency has no correlation with the stage of disease or cancer.

It is expected that different EBV-associated diseases with the same type of viral latency would have similar methylation patterns (Tempera et al. Semin Cancer Biol 2014; 26:22-9, Fejer et al. J Gen Virol 2008; 89:1364-70). In one example, a previous study has shown a similar methylation pattern across the viral promoter regions of EBV in both B cells from healthy EBV-seropositive individuals and tumor tissues from EBV-positive lymphomas, which both exhibit type I latency, using methylation-specific PCR (Paulson et al. J Virol 1999; 73:9959-68).

A previous study has also attempted to study the methylation profiles of EBV by amplicon sequencing of bisulfite-converted DNA from cell lines and tissue samples of different EBV-associated diseases (Fernandex et al. Genome Res 2009; 19(3):438-51). The 77 amplicons designed covered the transcription start sites of 94 different EBV latent and lytic genes and two structural RNAs, EBER1 and EBER2. The methylation status, either methylated or unmethylated, of the transcription start sites across the EBV genome was assessed. These results only demonstrated that the free viral DNA was devoid of DNA methylation as opposed to quantification, and the viral DNA from the cell lines or tissue samples of EBV-associated malignancies had a large number of methylated EBV transcription start sites. Importantly, samples with different malignant conditions (i.e. NPC and different lymphomas) were clustered together with the clustering analysis based on the methylation patterns of the transcription start sites, and transiently positive or persistently positive subjects were not identified. Based on their methylation patterns, the different malignant conditions could not be differentiated.

Most of the previous studies have focused on the analysis of the viral methylation profiles in tumor and cell line samples. These tumor samples need to be obtained through invasive procedures, for example surgical biopsies. This may limit the diagnostic applications e.g., for screening and serial monitoring. And, previous studies have been focused on qualitative aspects, and not quantitative results.

Despite the above reported data, we investigate the feasibility of differentiating among different EBV-associated diseases that exhibit the same type of viral latency. In contrast to the reported data above, we describe methods based on the analysis of the methylation profiles of plasma EBV DNA sequences that could differentiate between different EBV-related diseases or stage of diseases. For example, instead of only analyzing the methylation status (either methylated or unmethylated) of the viral gene promoters, we studied the methylation level of each CpG site of cell-free EBV DNA molecules at a higher resolution in a genomewide manner. Remarkably, our data reveal that we could differentiate among different EBV-associated conditions and malignancies with the same latency type based on the methylation analysis of cell-free EBV DNA molecules. Our data thus provide new information on cell-free EBV DNA methylation patterns beyond that of latency type-specific variability.

Embodiments can analyze the methylation patterns of cell-free EBV DNA molecules in blood (e.g. in plasma or serum). Embodiments of the present disclosure can also be used in other bodily fluids containing cell-free EBV DNA molecules, e.g. urine (Chan et al. Clin Cancer Res 2008; 14(15):4809-13), serum, vaginal fluid, uterine or vaginal flushing fluids, plural fluid, ascitic fluid, cerebrospinal fluid, saliva, sweat, tears, sputum, bronchoalveolar lavage fluid, etc. Stool samples can also be used. The technical challenges are the low abundance and fragmented nature of viral molecules, when compared to analysis of tumoral DNA in tissue samples. Our present disclosure demonstrates the feasibility of methylation analysis of cell-free viral molecules in a noninvasive manner.

II. Measuring Methylation of Cell-Free Ebv DNA Molecules

Methylation level(s) can be measured at various sites in a genome, e.g., animal (such as human), viral, or other. Methylation levels can be determined using methylation information at one or more sites, e.g., CpG sites. The methylation information can include counts of DNA molecules methylated at a given site or intensity signals corresponding to an amount of methylated/unmethylated DNA molecules. The methylation level can provide a relative abundance between methylated DNA molecules and unmethylated DNA molecules, e.g., where the amount of all or unmethylated DNA molecules at sites can act as a normalization factor.

For a viral genome, the mean methylated CpG density (also called methylation density, MD) of specific loci across the viral genome in the plasma can be calculated using the equation:

$$MD = \frac{M}{M+U}$$

where M is the count of methylated viral reads and U is the count of unmethylated viral reads at the CpG sites within the genetic locus across the viral genome. If there is more than one CpG site within a locus, then M and U correspond to the counts of methylated and unmethylated reads, respectively, across the sites. As examples, such counts of individual DNA fragments being methylated or unmethylated can be determined using sequencing or digital PCR. As another example, the methylation density can also be determined using real-time PCR to obtain a ratio of intensity of signals (e.g., a ratio a methylated intensity vs. unmethylated intensity), as opposed to counting specific numbers of reads. Thus, the analysis of nucleic acids can be performed collectively, where an intensity signal corresponds to multiple nucleic acids. The particular form for the methylation level can vary, e.g., a proportion as above or a ratio between M and U.

A. Various Techniques for Assessing Methylation Levels

Different approaches can be used for determining the methylation levels, e.g., to determine a methylation profile spanning all or a substantial part of a genome, e.g., a human genome or a viral genome. To interrogate a methylation profile comprehensively, example embodiments can use massively parallel sequencing (MPS) of bisulfite-converted DNA to provide genomewide information and quantitative assessment of the level of methylation on a per nucleotide and per allele basis. Any methylation-sensitive assay could be used to determine the methylation levels of the selected CpG sites. Other example techniques include single molecule sequencing (e.g. nanopore sequencing (Simpson et al. Nat Methods 2017; 14(4):407-410)), methylation-specific PCR (Herman et al. Proc Natl Acad Sci USA 1996; 93(18): 9821-9826), treatment with enzymes that differentially modify DNA molecules based on their methylation status (e.g. methylation-sensitive restriction enzymes), methylation binding proteins (e.g. antibodies), or mass spectrometry based methods (e.g. Lin et al. Anal Chem 2016; 88(2): 1083-7).

Various types of methylation can be analyzed. In some embodiments, we have used 5-methylation of cytosine residues as an example. Other types of DNA methylation changes can also be used, e.g. hydroxymethylation or methylation of adenine. Hence, technologies for detecting hydroxymethylation can also be used, e.g. oxidative bisulfite sequencing (Booth et al. Science 2012; 336(6083):934-7) and Tet-assisted bisulfite sequencing (Nat Protoc 2012; 7(12):2159-70). Further details for determination and use of a methylation profile can be found in U.S. Patent Publications 2015/0011403 and 2016/0017419, and 2017/0029900, which are incorporated by reference in their entirety.

During bisulfite modification, unmethylated cytosines are converted to uracils and subsequently thymines after PCR amplification while the methylated cytosines would remain intact (Frommer M, et al. Proc Natl Acad Sci USA 1992; 89:1827-31). After sequencing and alignment, the methylation of an individual CpG site could thus be inferred from the count of methylated sequence reads 'M' (methylated) and the count of unmethylated sequence reads 'U' (unmethylated) at the cytosine residue of the CpG site. Using bisulfite sequencing data, viral methylomes from the plasma of subjects with different virus-associated conditions could be constructed.

As described above, methylation profiling can be performed using massively parallel sequencing (MPS) of bisulfite converted DNA. The MPS of the bisulfite converted DNA can be performed in a random or shotgun fashion, or in a targeted fashion. For example, region(s) of interest in the bisulfite converted DNA can be captured using a solution-phase or solid-phase hybridization-based process, followed by the MPS.

The MPS can be performed using a sequencing-by-synthesis platform (e.g., the Illumina HiSeq or NextSeq or NovaSeq platform), a sequencing-by-ligation platform (e.g., the SOLiD platform from Life Technologies), a semiconductor-based sequencing system (e.g., the Ion Torrent or Ion Proton platforms from Life Technologies), the GenapSys Gene Electronic Nano-Integrated Ultra-Sensitive (GENIUS) technology, single molecule sequencing system (e.g., the Helicos system or the Pacific Biosciences system) or a nanopore-based sequencing system (e.g. from Oxford Nanopore Technologies or the Genia platform from Roche (sequencing.roche.com/research—development/nanopore-sequencing.html)). Nanopore-based sequencing including nanopores that are constructed using lipid bilayers and protein nanopore, and solid-state nanopores (such as those that are graphene-based). As selected single molecule sequencing platforms would allow the methylation status of DNA molecules (including N6-methyladenine, 5-methylcytosine and 5-hydroxymethylcytosine) to be elucidated directly without bisulfite conversion (B. A. Flusberg et al. 2010 Nat Methods; 7:461-465; J. Shim et al. 2013 Sci Rep: 3:1389. doi: 10.1038/srep01389), the use of such platforms would allow the methylation status of non-bisulfite converted sample DNA (e.g. plasma or serum DNA) to be analyzed. The sequence may include paired-end sequencing or provide a single sequence read for the entire DNA molecule.

Besides sequencing, other techniques can be used, e.g., as mentioned above. In one embodiment, methylation profiling can be done by methylation-specific PCR or methylation-sensitive restriction enzyme digestion followed by PCR or ligase chain reaction followed by PCR. In yet other embodiments, the PCR is a form of single molecule or digital PCR (B. Vogelstein et al. 1999 Proc Natl Acad Sci USA; 96:9236-9241). In yet further embodiments, the PCR can be a real-time PCR (Lo et al. Cancer Res 1999; 59(16):3899-903 and Eads et al. Nucleic Acids Res 2000; 28(8):E32). In other embodiments, the PCR can be a multiplex PCR. In one embodiment, methylation profiling can be done by using microarray-based technologies.

After sequencing, the sequence reads can be processed in Methyl-Pipe, a methylation data-analysis pipeline (Jiang et al. PLoS One 2014; 9:e100360) and mapped to an artificially combined reference sequence that consists of the whole human genome (hg19), the whole EBV genome (AJ507799.2), the whole HBV genome, and the whole HPV genome. Different reference sequences can be used, and the mapping can be performed to each of the genomes separately, as opposed to combining into one reference sequence. Sequenced reads mapping to unique position in the combined genomic sequence can be used for downstream analysis.

B. Targeted Bisulfite Sequencing Using Capture Probes

Certain embodiments can interrogate specific regions for the methylation patterns of plasma EBV DNA molecules. In one embodiment, targeted bisulfite sequencing with capture enrichment can be used to analyze the cell-free viral DNA molecules in the circulation of subjects with different EBV-associated diseases or conditions. For example, capture probes may be designed to cover all or some of the CpG sites of the EBV genome. This approach can also be used for other viruses. Hence, capture probes can also be designed to cover all or some of the CpG sites of the hepatitis B virus (HBV) genome, the human papillomavirus (HPV) genome, and other viral/bacterial genomes. In the same analysis, capture probes can also be included to target genomic regions in the human genome.

In some embodiments, to take into account of the differences in size between a viral genome and the human genome, more probes can be designed to hybridize to viral genomic sequences than human genomic regions of interest may be used. In another embodiment, one can target whole viral genomes, e.g., designing on average 200 hybridizing probes covering each viral genomic region with ~200 bp in size (e.g., 200× tiling capturing probes). In one embodiment and as an example, for the regions of interest in the human genome, we designed on average 5 hybridizing probes covering each region with ~200 bp in size (e.g., 5× tiling capturing probes). As an illustration, the capture probes may be designed according to FIG. 1.

FIG. 1 shows the design of capture probes for targeted bisulfite sequencing according to embodiments of the present disclosure. FIG. 1 provides information about capture probes, e.g., size of capturing regions and the amount of tiling covered by the probes. The capture probes can be various lengths and overlap with each other. Such capture probes can use the SeqCap-Epi system (Nimblegen). Other embodiments may not use such capture probes.

Column 101 identifies the type of sequence, i.e., autosomes of the human or viral targets. Column 102 identifies the particular sequence (e.g., of a chromosome or of a particular viral genome). Column 103 provides the total length in base pairs (bp) that the capture probes cover. The capture probes may not cover the entire sequence (e.g. as shown for the autosomes), but may cover the entire sequence, e.g., for a viral genome. Column 104 provides the capture probe depth, also referred to as probe filing fold. These numbers convey the number of probes covering any given position. For the autosomes, the capture probes provide 5× tiling on average. For the viral targets, the capture probes provide 200× tiling on average. Thus, the number of probes for the viral is a higher percentage/proportion per unit length than the autosomes. Such a higher level of concentration of capture probes for the viral targets can help maximize the chance of capturing the viral DNA.

III. Methylation Levels of Plasma EBV DNA for Various Conditions

We have analyzed the methylation patterns of plasma EBV DNA molecules in patients with various EBV-associated diseases/condition, e.g., NPC, infectious mononucleosis, Hodgkin's lymphoma, NK-T cell lymphoma, and apparently healthy individuals with detectable plasma EBV DNA. Those apparently healthy subjects with detectable plasma EBV DNA were retrieved from a subject cohort recruited for the screening of NPC and were classified into 2 groups. The first group included those subjects who had detectable plasma EBV DNA levels on the initial test, but undetectable levels on the follow-up test and were denoted as 'transiently positive'. The second group included those subjects who had detectable plasma EBV DNA levels on both the initial and follow-up tests and were denoted as 'persistently positive'.

Targeted bisulfite sequencing with capture enrichment by specifically designed capture probes was used. For each plasma sample analyzed, DNA was extracted from 4 mL plasma using the QIAamp DSP DNA blood mini kit. For each case, all extracted DNA was used for the preparation of sequencing library using the KAPA library preparation kit (Roche) or TruSeq DNA PCR-free library preparation kit) (ILLUMINA®). The adapter-ligated DNA products were subjected to two rounds of bisulfite treatment using an EpiTect Bisulfite Kit (Qiagen). Twelve to fifteen cycles of PCR amplification were performed on the bisulfite-converted samples using the KAPA HiFi HotStart Uracil+ ReadyMix PCR kit (Roche). The first PCR amplification can increase the quantity of DNA for the target capture. An input amount of DNA can be suggested for the target capture reaction. The input DNA amount from plasma (without amplification) may not be sufficient for target capture.

The amplification products were then captured with the SeqCap-Epi system (Nimblegen) using the custom-designed probes covering the viral and human genomic regions stated above (FIG. 1). Substantial 'loss of DNA' can occur the capturing step. The amount of DNA after target capture reaction may be less than required for sequencing. Therefore, a second amplification stage (e.g., using PCR) can amplify the DNA amount for subsequent sequencing step. Thus, in some embodiments, after the target capture, the captured products were enriched by 14 cycles of PCR to generate DNA libraries. The DNA libraries were sequenced on a NextSeq platform)(ILLUMINA®. For each sequencing run, four to six samples with unique sample barcodes were sequenced using the paired-end mode. From each DNA fragment, 75 nucleotides were sequenced from each of the two ends, but other numbers of nucleotides can be sequenced.

A. Methylation Profiles of Plasma EBV DNA in Different EBV-Associated Conditions FIG. 2 shows the methylation densities of CpG sites across the EBV genome in patients with infectious mononucleosis, NPC, and NK-T cell lymphoma according to embodiments of the present disclosure. The methylation profiles of EBV DNA were generated through targeted capture bisulfite sequencing of plasma EBV DNA fragments. The horizontal axis provides the genomic coordinates in the EBV reference genome. The vertical axis provides the methylation density at a single CpG site resolution.

The methylation densities of the CpG sites across the EBV genome were derived with the formula described above:

$$MD = \frac{M}{M+U}.$$

We could observe different patterns of methylation density of plasma EBV DNA amongst different subjects. These differences in the profiles of DNA methylation could be analyzed on a global or locus-specific level. For example, on a global level, we observed a total lower methylation level in the patient with infectious mononucleosis (TBR1610) (methylation density of 57.3%) than the two patients with NPC (TBR1392 and TBR1416) (methylation densities of 83.8% and 81.3%). The global methylation level uses methylation measurements for sites across the genome to determine a single value.

Also on a relatively macroscopic level, the patient with NK-T cell lymphoma (TBR1629) exhibited a greater heterogeneity in the methylation levels across the EBV genome than the two patients with NPC (TBR1392 and TBR1416), for example, between genomic coordinates 50000 to 100000. The heterogeneity shows up as dips in the methylation density plot. The NPC patients have relatively uniform density, whereas the lymphoma patient show many tiny valleys where the density drops significantly, thereby giving a comb-like structure.

Patterns of DNA methylation could also be analyzed on a locus-specific or region-specific level. These loci could be of any size and of at least 1 CpG site. These loci may or may not associated with any annotated viral genes. Such region-specific methylation levels can have similar values across different subject with the same condition, but have different values relative to other subjects with a different condition.

In FIG. 2, we define 4 genomic regions, namely region 201 (7,000-13,000), region 202 (138,000-139,000), region 203 (143,000-145,000), and region 204 (169,000-170,000). The region-specific methylation densities in regions 201 and 204 were higher in the two cases of NPC (TBR 1392 and TBR 1416) than the case of infectious mononucleosis (TBR 1610). The region-specific methylation density in region 203 was, on the contrary, lower in the two cases of NPC than the case of infectious mononucleosis. The region-specific DNA methylation density in region 203 was highest in the case of NK-T cell lymphoma (TBR 1629) than the other cases of NPC and infectious mononucleosis. Such results demonstrate that there are different patterns of methylation profiles of plasma EBV DNA fragments on a global and locus-specific level in patients with different EBV-associated conditions.

Accordingly, a low methylation level in region 201 can indicate that a subject has infectious mononucleosis. A high methylation level in region 204 can indicate the subject has NPC. And, a high methylation level in region 203 can indicate the subject has NK-T cell lymphoma. The specific values for threshold defining what is high or low (or an intermediate range) can be determined for each region based on measurements of the type shown in FIG. 2. Such regions can be selected by analyzing the methylation profiles of subjects with the different conditions and choosing regions that have different methylation densities for different conditions. Further, measurements from multiple regions may be combined, e.g., via clustering techniques or a decision tree.

B. Early Stage NPC

Figure 3:
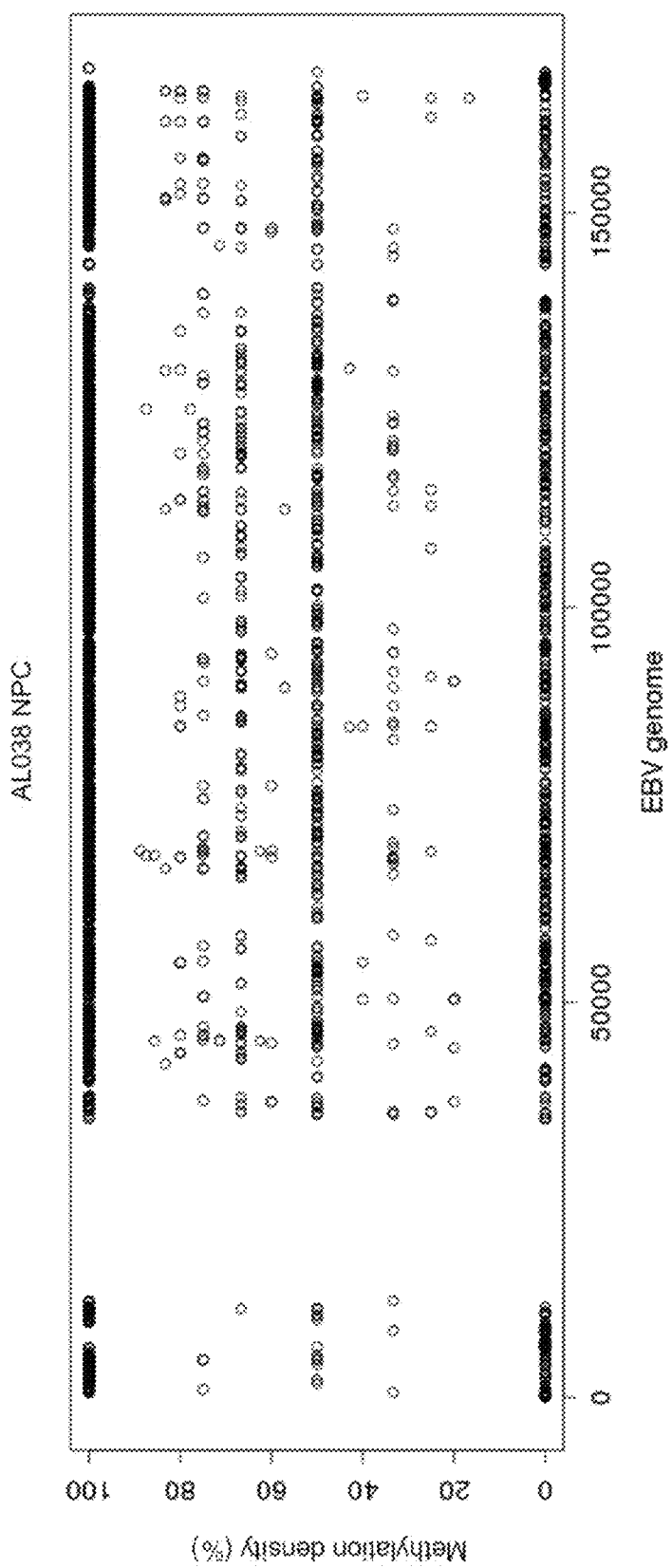
FIG. 3 shows the methylation profiles of plasma EBV DNA in a patient (AL038) from a screening cohort with early stage NPC (Stage I) according to embodiments of the present disclosure.

FIG. 3 shows the methylation profiles of plasma EBV DNA in a patient (AL 038) from our screening cohort with early stage NPC (Stage I) and a low concentration of plasma EBV DNA (8 copies/mL plasma as measured by quantitative PCR). Plasma DNA was extracted from the initial blood sample. Subjects with a positive initial (baseline) test were be retested 4 weeks later, and that was regarded as a follow-up test. This patient did not have symptoms of NPC at the time of blood sampling, and the cancer was detected through screening using real-time PCR analysis of plasma EBV DNA with a two stage analysis. Subjects with persistently positive plasma EBV DNA by real-time PCR were further confirmed using nasal endoscopy and Mill.

FIG. 3 shows that the signal is more noisy, e.g., some sites have 100% methylation density and some sites have very low methylation density, such as zero. To remove such noisy behavior, embodiments can use region methylation levels that are measured using the combined methylation density of all the sequence reads at sites within the window. For example, a 200 bp window can be used, which can reduce the noise and provide smoother data. Accordingly, even with low EBV DNA sequence concentration in the sample, methylation levels can be measured and used to distinguish different conditions. More data showing such ability to distinguish conditions is provided below.

In this patient, the amount of plasma EBV DNA fragments being captured was comparatively lower than the other two patients (TBR1392 and TBR1416) with advanced stage NPC and high concentrations of plasma EBV DNA. As mentioned above, this illustrates a case where methylation level(s) can still be used to identify a particular condition—NPC in this case—even though the EPV concentration is low. Further, the amount of plasma EBV can be used as part of determining a level of disease (e.g., a level of cancer).

C. Difference Values in Methylation Profiles Among Patients

A difference in the methylation profiles can provide a comparison between patients with NPC and infectious mononucleosis As shown earlier in FIG. 2, there are different methylation patterns of plasma EBV DNA among patients with different EBV-associated conditions. We analyze the difference in the methylation patterns by comparing the methylation densities of CpG sites across the EBV genome between these different patients.

1. Different Conditions

Figure 4:
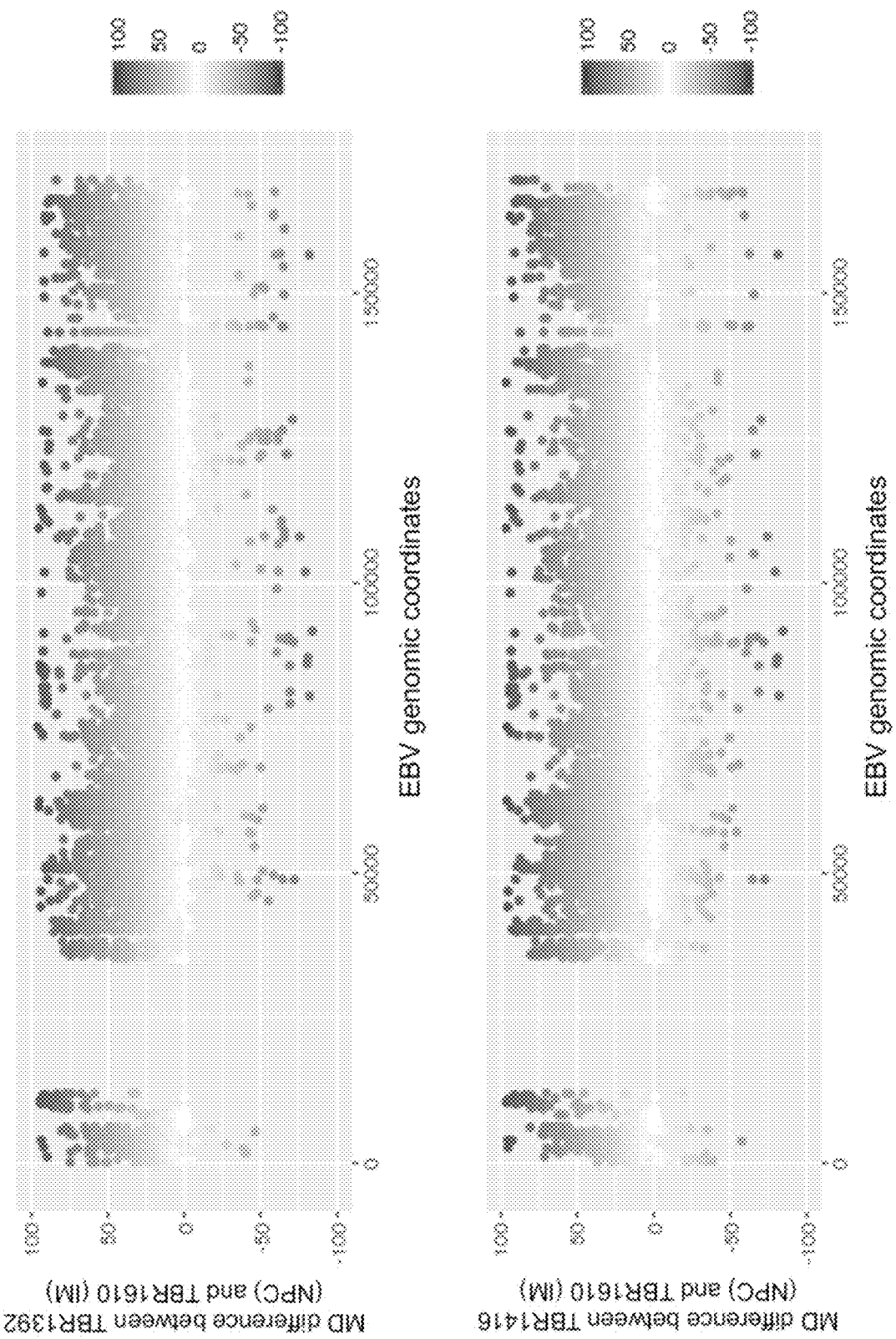
FIG. 4 shows the differences in methylation densities of CpG sites across the EBV genome between two patients with different conditions according to embodiments of the present disclosure.

FIG. 4 shows the differences in methylation densities of the CpG sites across the EBV genome between two patients with different conditions according to embodiments of the present disclosure. The horizontal axis is the genomic coordinate in the EBV genome. The vertical axis shows the per-site difference in the methylation between the two patients. The median methylation difference between NPC (TBR1392) and infectious mononucleosis (TBR1610) was 23.9% (IQR (interquartile range): 14.8-39.3%), suggesting the NPC methylation level across CpG sites in EBV genome was systematically higher in NPC than in infectious mononucleosis. Similar patterns of methylation difference (median: 22.9%; IQR: 13.3-37.8%) were observed in another comparison between NPC (TBR1416) and infectious mononucleosis (TBR1610).

The upper diagram shows the differences in methylation densities between a patient with NPC (TBR1392) and a patient with infectious mononucleosis (TBR1610). A positive value at one CpG site indicates a higher methylation density in case TBR1392 than case TBR1610 at that particular site. A negative value indicates a lower methylation density in case TBR1392 than case TBR1610 at that CpG site.

The lower diagram shows the differences in methylation densities between another patient with NPC (TBR1416) and the same patient with infectious mononucleosis (TBR1610). This graphical presentation illustrates one example of analysis and comparison of methylation patterns of plasma EBV DNA in different EBV-associated conditions.

In general, the NPC patients have higher methylation, and the differences in methylation have significant values. Such difference values can be quantified in various ways, e.g., by summing to get a global difference value. This global difference value can act as a distance between two subjects, as may be used in clustering, where each methylation value (e.g., as an index per site or a level per region) is one data point in a multidimensional data point.

2. Same Condition

Figure 5:
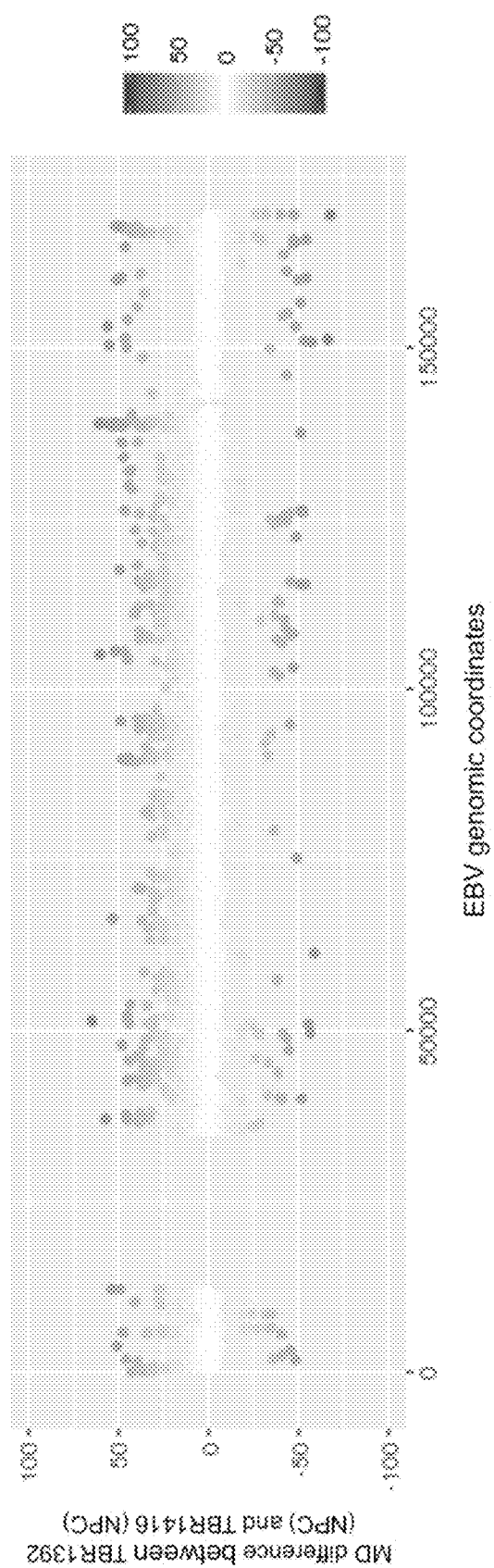
FIG. 5 shows the differences in methylation densities of CpG sites across the EBV genome between two patients with NPC (TBR1392 and TBR1416) according to embodiments of the present disclosure.

FIG. 5 shows the differences in methylation densities of the CpG sites across the EBV genome between two patients with the same diagnosis of NPC (TBR1392 and TBR1416) according to embodiments of the present disclosure. In general, there are smaller differences in methylation densities across the EBV genomes, compared to previous analyses for patients with two different diseases (FIG. 4). The median methylation difference between two NPC subjects (TBR1392 vs. TBR1416) was 0.3% (IQR: −1.2-2.5%). This suggests that patients with the same diagnosis of EBV-associated disease would have similar methylation patterns of plasma EBV DNA. The difference in methylation densities could have implications on some disease characteristics specific to the particular case and provide additional diagnostic or prognostic information.

3. NPC and False Positive

Figure 6:
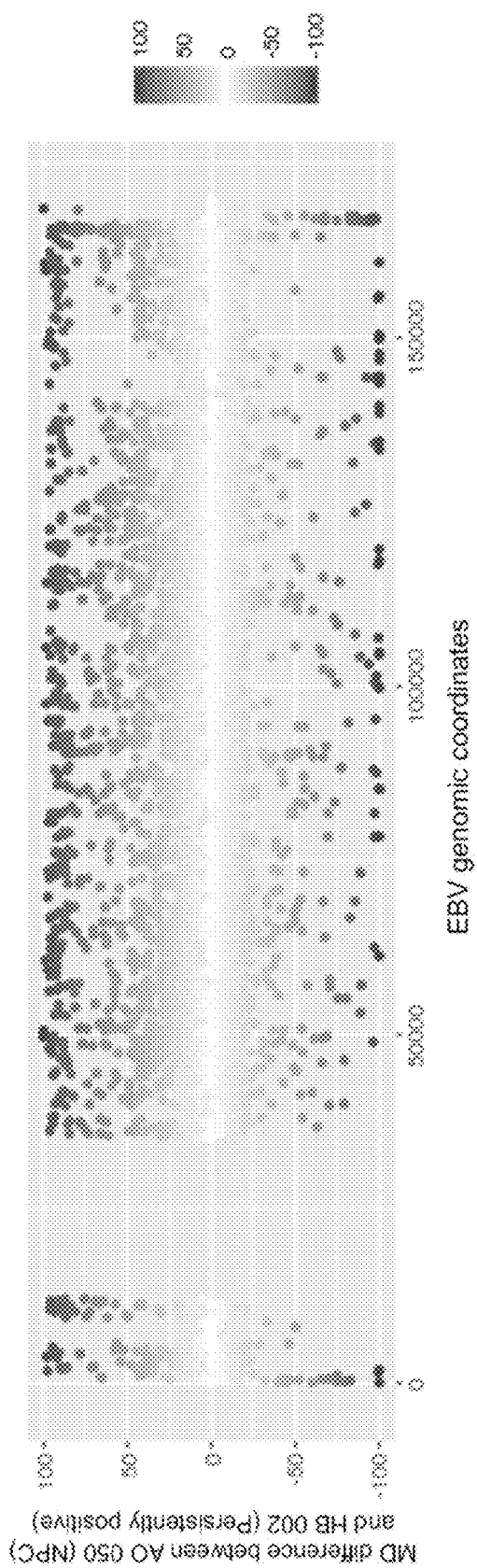
FIG. 6 shows the differences in the methylation patterns of plasma EBV DNA between a patient with early stage NPC (A0050) and a subject with false positive result of plasma EBV DNA (HB002) according to embodiments of the present disclosure.

FIG. 6 shows the differences in the methylation patterns of plasma EBV DNA between a patient with early stage NPC (A0050) and a subject with false positive result of plasma EBV DNA (HB002) according to embodiments of the present disclosure. This comparison shows the methylation patterns of plasma EBV DNA between a patient with early stage NPC and a subject without NPC, but who was persistently positive for plasma EBV DNA on serial tests. Both of them were from our screening cohort. The plasma DNA was extracted from their initial blood samples upon recruitment.

As shown in FIG. 6, there are differences in the methylation patterns of plasma EBV DNA between the patient with early stage NPC (A0050) and the subject with false positive result of plasma EBV DNA (HB002). But, the number and size of the differences is less than in the plots of FIG. 4, between an NPC subject and an IM subject. Thus, the fact that there are differences between the NPC subject and the false positive subject indicates an ability to increase the accuracy of cancer screening. And, the fact that the differences are of a different scale than for the IM subject indicates any ability to distinguish subjects having any of the three conditions. Based on this observation, we explored the diagnostic utility to differentiate the two groups (subjects with early-stage NPC and false positive results) using plasma EBV DNA methylation patterns, for which data is provide in a later section.

D. Correlation Between Methylation Densities of Similar and Different Patients Besides analyzing the difference values between methylation densities at different sites, the methylation densities can be plotted together to identify a correlation or lack therefore. For example, each data point in a two dimensional plot can include the two methylation densities from two subjects at a same site. If the methylation densities are correlated (e.g., the two subjects have the same condition), then the plot will exhibit linear behavior. If the methylation densities are not correlated (e.g., the two subjects have the same condition), then the plot will not exhibit linear behavior.

Figure 7C:
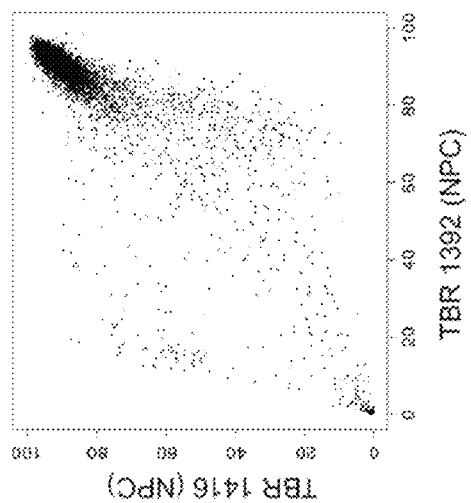
FIGS. 7A-7C are dot plots showing the methylation density of a CpG site across the EBV genome in one patient (on the x-axis) and the corresponding methylation density of the same CpG site in the other patient (on the y-axis) according to embodiments of the present disclosure.
Figure 7B:
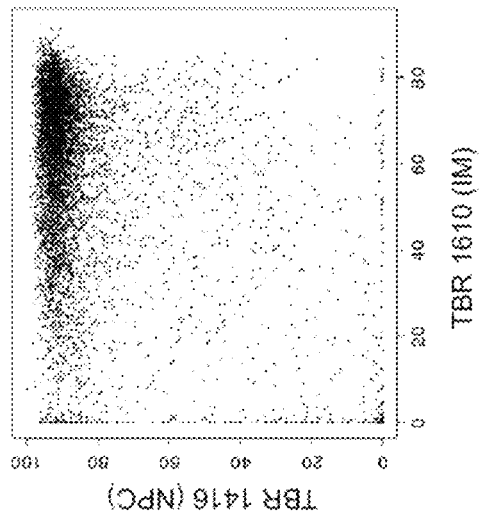
Figure 7A:
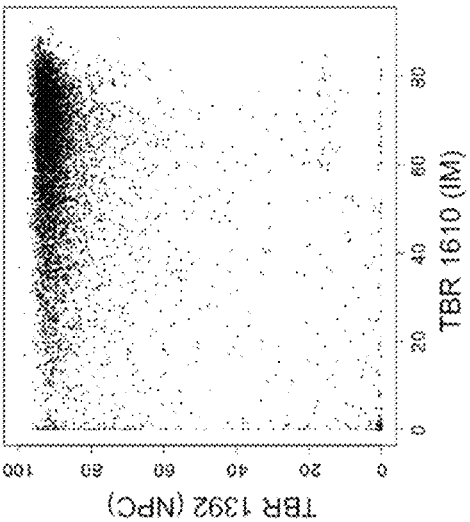

FIGS. 7A-7C illustrate the differences in methylation profiles of plasma EBV DNA between two clinical cases. In FIGS. 7A-7C, each data point in the three graphs represents the methylation density of a CpG site across the EBV genome in one patient (on the x-axis) and the corresponding methylation density of the same CpG site in the other patient (on the y-axis).

FIGS. 7A and 7B show the methylation densities between two patients of different diseases (one NPC and one infectious mononucleosis). As can be seen, the methylation densities are not correlated. The NPC subjects consistently have a high methylation density (e.g., above 80%) that is not matched by the IM subject, thereby causing a horizontal band along the top. Such behavior indicates that the two subject are different, e.g., different conditions. Different conditions can include one with disease and the other without disease.

FIG. 7C shows the methylation densities between two different patients with NPC. In FIG. 7C, we can observe a diagonal trend line (slope being approximately equal to 1), suggesting that the methylation density of each CpG site is similar between two different patients with NPC. This graphical pattern is not observed in FIGS. 7A and 7B. These results again suggest that patients with different EBV-associated diseases have different methylation profiles of plasma EBV DNA fragments. Embodiments can use such different methylation properties of the sites (or of regions of sites) to identify sites/regions that have different methylation densities between different conditions, and use those sites/regions to determine a methylation level(s) for discriminating between the conditions.

IV. Discriminating Among Ebv-Associated Conditions Using Methylation Patterns of Plasma Ebv DNA For a systematic comparison of the methylation profiles of plasma EBV DNA in different EBV-associated conditions, we used a 'methylation percentage' (one example of a type of 'methylation density'), for each case. The methylation percentage of plasma EBV DNA fragments can be derived using the equation:

$$\text{Methylation \%} = \frac{M'}{M' + U'}$$

where M' is the count of methylated reads and U' is the count of unmethylated reads at one or more CpG sites, which may be pre-selected. The methylation percentage can be calculated based on all CpG sites or some CpG sites within the EBV genome covered by our capture probes. Other examples of methylation levels can also be used.

A. Genomewide Aggregated Methylation Level

As one example of a single methylation level across the EBV genome can be determined. The aggregate number of methylated EBV DNA molecules at a specific set of CpG sites can be used to determine the methylation percentage as a genomewide methylation level, with a normalization by a measured amount including other DNA molecules, e.g., as a measure of volume, an intensity corresponding to the other DNA molecules, or a count of the other DNA molecules. In one embodiment, we calculated the methylation percentage of plasma EBV DNA molecules based on the CpG sites within the EBV genome covered by our capture probes.

Figure 8:
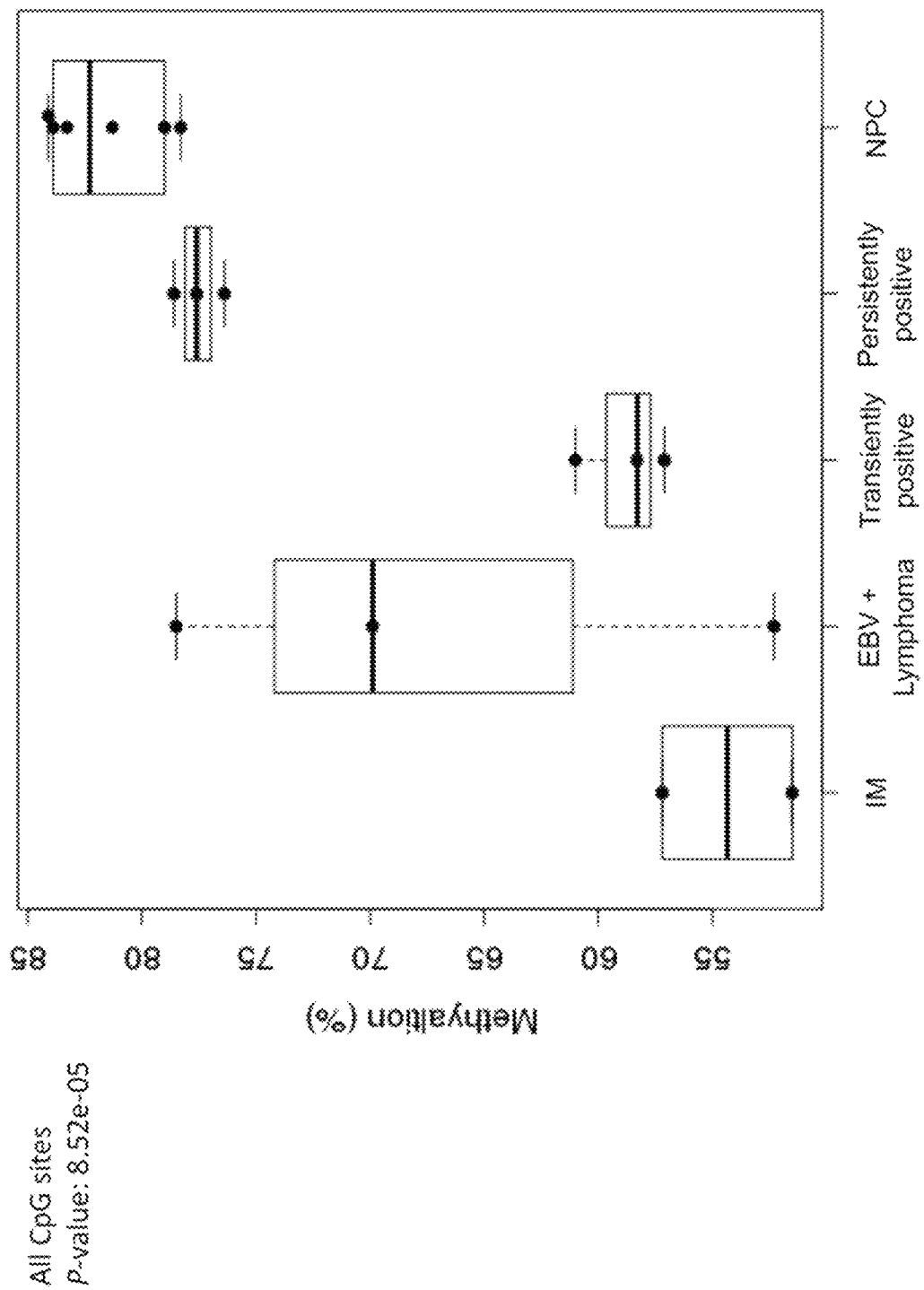
FIG. 8 shows the methylation percentages of plasma EBV DNA based on CpG sites in the EBV genome in subjects with infectious mononucleosis (IM) (n=2), EBV-associated lymphoma (n=3), transiently positive plasma EBV DNA (n=3), persistently positive plasma EBV DNA (n=3) and NPC (n=6) according to embodiments of the present disclosure.

FIG. 8 shows the methylation percentages of plasma EBV DNA based on all CpG sites covered in subjects with infectious mononucleosis (IM) (number of patients n=2), EBV-associated lymphoma (n=3), transiently positive plasma EBV DNA (n=3), persistently positive plasma EBV DNA (n=3), and NPC (n=6) according to embodiments of the present disclosure. FIG. 8 shows box and whisker plots for the five different conditions. As can be seen, the median values are sufficiently separated to discriminate between the different conditions. For example, a reference level of about 79% can discriminate between patients that are persistently positive for EBV and those that have NPC.

Overall, we could differentiate among different EBV-associated diseases/conditions through analysis of genomewide aggregated methylation percentage of plasma EBV DNA (p-value=8.52e−05, one-way ANOVA test). Four out of the six patients with NPC were from the screening cohort and had early stage NPC (stage I or II). Thus, even early stages of a condition can be discriminated from subjects not having the condition (e.g., even the persistently positive subjects). Different reference levels can be used to discriminate between different conditions, e.g., lower than about 57% can be used to identify IM and between 57% and 63% can be used to identify transiently positive subjects. In some embodiments, more than one condition out of a larger set of conditions can be identified for a given methylation level (e.g., lymphoma and transiently positive could be identified in the range 57% to 63%). In such a situation, a probability can be assigned to each of the conditions. For example, the methylation of a tested subject can be compared to two groups of reference subjects, one group suffering from condition A (e.g. lymphoma) and the other suffering from condition B (e.g. infectious mononucleosis). The number of standard deviations from the means of the two groups of reference subjects can be determined. Based on the number of standard deviations, the probabilities of suffering from the two conditions can be computed. These probabilities can be used to determine the relative likelihood of suffering from these two conditions.

The specific reference value(s) selected can depend on the specific manner in which the methylation level is determined. For example, a methylation percentage would have different reference levels than if the number of methylated DNA molecules M (e.g., as determined using a number of reads or an intensity) is divided by the number of unmethylated DNA molecules U (e.g., as determined using a number of reads or an intensity), e.g., M/U. Other scaling factors or additive factors would change the particular reference values. As long as a methylation level of a current sample is determine in a same manner as the methylation levels of the reference samples, then the selected reference levels will be applicable. The reference levels can also depend on the sites selected for measuring the methylation level, as shown in later results.

The ability to discriminate between different conditions using a methylation level can depend on the number of DNA molecules detected at the sites, but the results presented herein show that the number of EBV DNA molecules can be relatively low. For example, in FIG. 8, the $5^{th}$ percentile of plasma EBV DNA molecules analyzed in the different subjects is 44, with the minimum being 26. In various embodiments, the number of cell-free viral DNA molecules can include at least 10 cell-free DNA molecules, e.g., 20, 30, 40, 50, 100, or 500). In other embodiments, the total number of cell-free DNA molecules analyzed for the subject and the particular viral genome can be at least 1,000 cell-free DNA molecules or more (e.g., at least 10,000, at least 100,000, or at least 1,000,000).

B. Differentially Methylated Regions (DMRs)

Instead of using all sites covered by the capture probes, only certain sites may be used. These sites may be determined by analyzing all the sites and then selecting ones having a certain properties, e.g., having different methylation levels among between certain conditions. The sites can be analyzed individually or collectively by regions, e.g., more than one site can be allocated to a region and a methylation level determined for that region. The sites and regions can be genomewide by spanning the viral genome, e.g., not restricted to just one site/region. For example, at least one site/region can be used for every 1 kb, 2 kb, 5 kb, or 10 kb.

Accordingly, some embodiments can calculate the methylation percentages based on CpG sites within differentially methylated regions (DMRs). We have shown earlier that the methylation patterns of plasma EBV DNA are different in different EBV-associated diseases. Therefore, there should exist DMRs within which the methylation levels are different between different diseases/conditions. Besides using individual sites, non-overlapping windows of different sizes can be used. For example, the sizes of the non-overlapping regions could be set at, but not limited to, 50 bp, 100 bp, 200 bp, 300 bp, 400 bp, 500 bp, 600 bp, 800 bp and 1000 bp. In another example, each CpG site can be analyzed separately, e.g., without use of regions combining sites.

The DMRs can be selected to have particular methylation levels in subjects have different conditions. For example, the DMR could be defined if the methylation percentages of the CpG sites within the region are less than 10%, 20%, 30%, 40%, 50%, 60%, 70%, 80% or 90% in one or more cases of a disease/condition and greater than 10%, 20%, 30%, 40%, 50%, 60%, 70%, 80% or 90% in one case of another disease/condition. In yet another embodiment, more than one case per disease can be used to define the DMR. And, cutoff criteria for more than two diseases/conditions can be used, e.g., different ranges of methylation levels for each of the conditions.

1. DMRs Using IM<50% and NPC>80%

To demonstrate the mining of such DMRs, we randomly selected one patient with infectious mononucleosis (TBR1610) and one patient with NPC (TBR1392). Here, we first set non-overlapping windows of 500 base pairs (bp) in size across the EBV genome, e.g., bins of positions 1-500, 501-1000, etc. . . . . Within the 500-bp regions, we calculated the average methylation percentages of all the CpG sites within the region in the patient with IM (TBR1610) and NPC (TBR1392). In this example, the 500-bp region would fulfil a first selection criteria for DMR if the average methylation percentages of all the CpG sites within the region are less than 50% in the case of infectious mononucleosis (TBR1610) and greater than 80% in the case of NPC (TBR1392).

Figure 9:
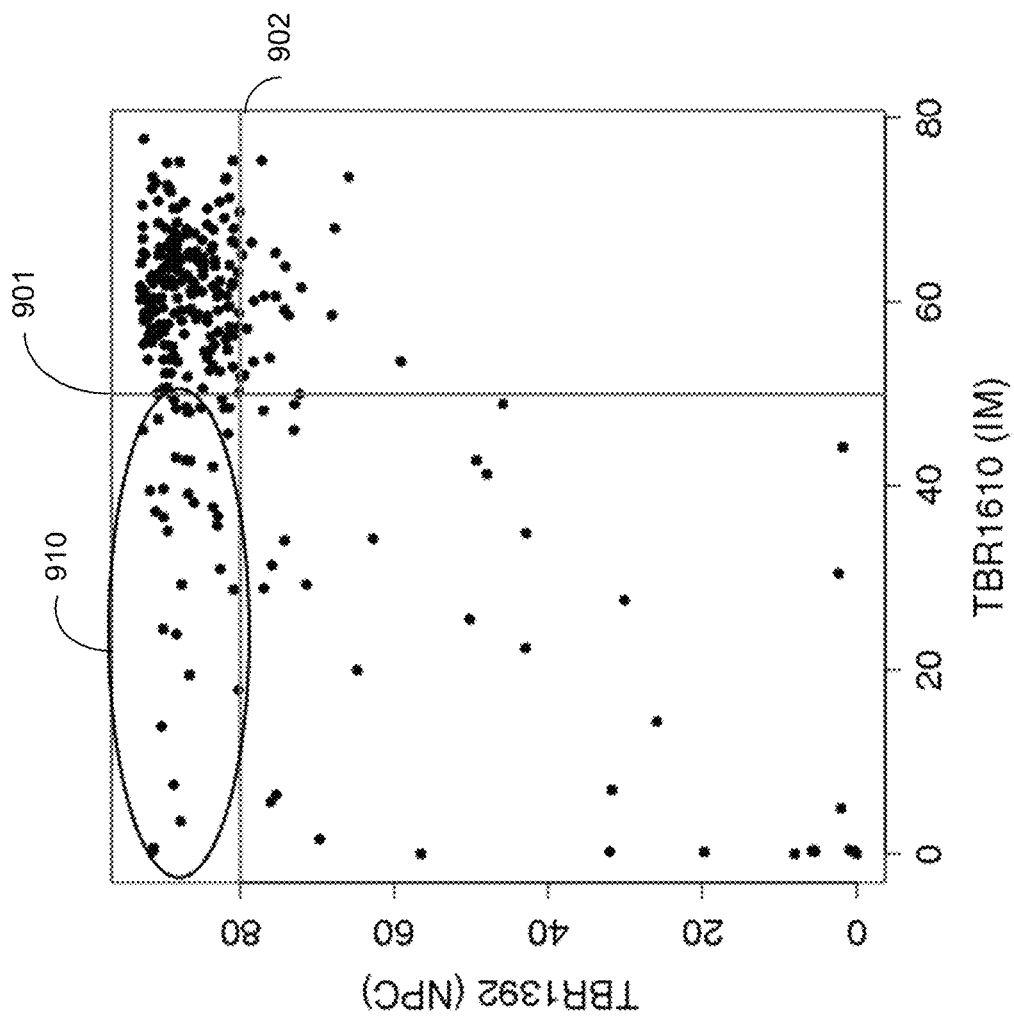
FIG. 9 illustrates the mining of differentially methylated regions (DMRs) fulfilling first selection criteria according to embodiments of the present disclosure.

FIG. 9 illustrates the mining of differentially methylated regions (DMRs) fulfilling the first selection criteria according to embodiments of the present disclosure. FIG. 9 corresponds to the two cases shown in FIG. 7A. Each data point in FIG. 9 represents the methylation percentage of a 500-bp region across the EBV genome in the IM subject (on the x-axis) and the corresponding methylation percentage of the same 500-bp region in the NPC subject (on the y-axis). With this first selection criteria defined above, we identified a total of 39 DMRs that comprised of 821 CpG sites (approximately 10% of the total CpG sites within the EBV genome being captured with our probes). These 39 DMRs are those within the upper left corner of FIG. 9.

In FIG. 9, the methylation percentage for the NPC subject is shown on the vertical axis, and the methylation percentage for the IM subject is shown on the horizontal axis. Vertical line 901 shows the cutoff of 50% for the methylation percentage in the case of IM. Horizontal line 902 shows the cutoff of 80% in the case of NPC. Thus, the regions in the upper left section (generally marked as 910) correspond to the DMRs for this example.

FIG. 10 is a table listing the genomic coordinates of the 39 differentially methylated regions fulfilling the criteria described in FIG. 9. Column 1001 lists the viral genome, which is EBV for this example. Column 1002 provides the starting genomic coordinate in the reference EBV genome. Column 1003 provides the ending genomic coordinate in the reference EBV genome. Column 1004 the methylation density in the IM subject and in the NPC subject.

These DMRs can then be used to determine methylation level(s) in other subjects. In one embodiment, the methylation status of each sequence read covering a site in one of this set of DMRs is used to determine a methylation percentage that corresponds to the set of DMRs. This methylation percentage can be determined in a similar manner as in FIG. 8, but a subset of the sequence reads are used, namely those corresponding to the sites in the set of DMRs. In other embodiments, individual methylation levels can be determined for each of the DMRs. The methylation levels for a subject can form a multidimensional data point, e.g., where clustering techniques or reference planes (hyperplanes in the multidimensional space) can separate subjects with different conditions or different classifications/levels of a condition. Other analytical methods for differentiating these conditions can be used, for example but not limited to, Naïve Bayes, random forest, decision tree, support vector machines, k-nearest neighbors, K-means clustering, Gaussian mixture model (GMM), density-based spatial clustering, hierarchical Clustering, logistic regression classifiers, and other supervised and unsupervised classification or regression methods.

Figure 11:
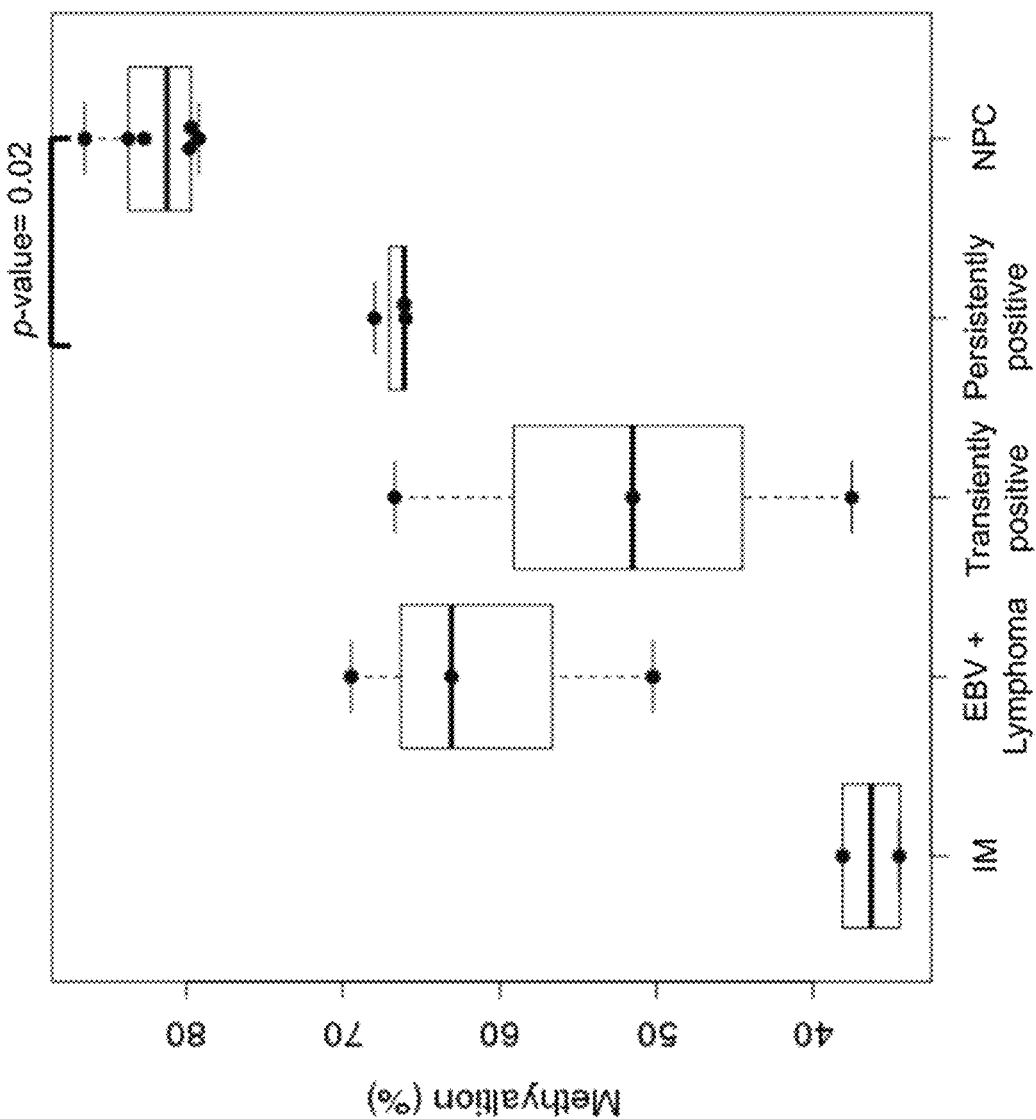
FIG. 11 shows the methylation percentages of plasma EBV DNA based on the 821 CpG sites within the 39 DMRs described in FIG. 10 in the subjects with infectious mononucleosis (IM) (n=2), EBV-associated lymphoma (n=3), transiently positive plasma EBV DNA (n=3), persistently positive plasma EBV DNA (n=3), and NPC (n=6) according to embodiments of the present disclosure.

FIG. 11 shows the methylation percentages of plasma EBV DNA based on the 821 CpG sites within the 39 DMRs defined above (FIG. 8) in the same group of subjects with infectious mononucleosis (IM) (n=2), EBV-associated lymphoma (n=3), transiently positive plasma EBV DNA (n=3), persistently positive plasma EBV DNA (n=3) and NPC (n=6) according to embodiments of the present disclosure. These are the same subjects used in FIG. 8. The methylation percentages are determined as a single value using sequence reads that correspond (e.g., align) to the 821 sites in the set of 39 DMRs.

FIG. 11 shows box and whisker plots for the five different conditions. As can be seen, the median values can discriminate between the different conditions. For example, a reference level of about 75% can discriminate between patients that are persistently positive for EBV and those that have NPC. We could observe a statistically significant difference in the methylation percentages among the different groups (p-value=1.83e−05, one-way ANOVA test), which is better than FIG. 8.

FIG. 11 has some differences than FIG. 8. For example, the spread in values for IM and NPC are smaller, resulting from the DMRs being specifically select to be in a particular range for those subjects. Such a result indicates that criteria of different ranges of methylation levels indicative of different conditions can provide more selective techniques discriminating among different classifications of subjects. Additionally, the difference between NPC subjects and persistently positive subjects is larger than in FIG. 8.

2. DMRs Using IM<80% and NPC>90%

As in the previous section, we performed an analysis for the use methylation percentages based on differentiated methylated regions to distinguish patients with early NPC and non-NPC subjects with detectable plasma EBV DNA. All the NPC patients and non-NPC subjects analyzed were identified through a prospective screening cohort (Chan et al. N Engl J Med 2017; 377:513-522). To mine the DMRs, we randomly selected two patients with NPC (TBR1416 and FD089) and one patient with infectious mononucleosis (TBR1748). In yet another embodiment, other EBV-associated disease or condition, including non-EBV subject with detectable plasma EBV DNA, could be used for mining of DMRs. We set non-overlapping windows of 500 base pairs (bp) in size across the EBV genome.

Figure 12:
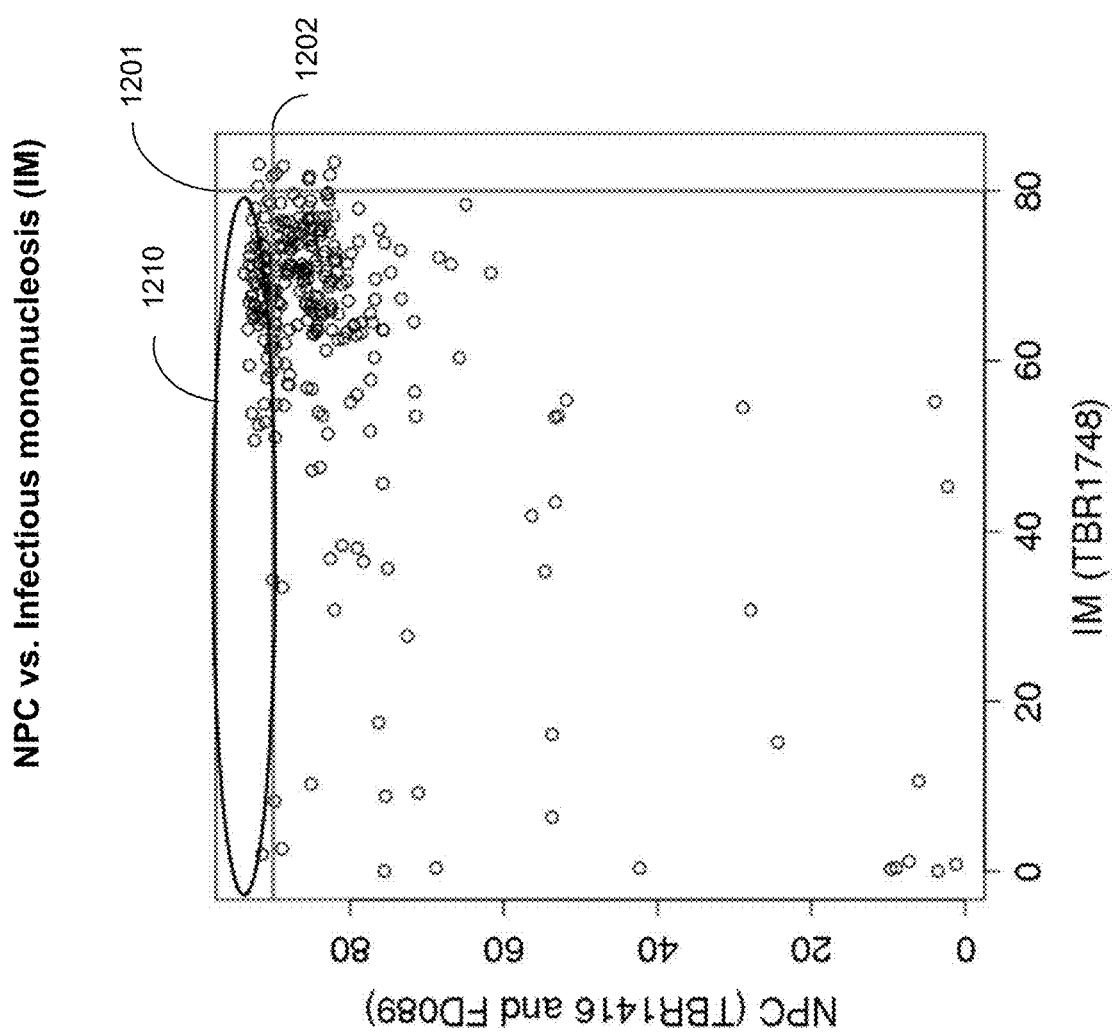
FIG. 12 illustrates the mining of differentially methylated regions (DMRs) fulfilling the second selection criteria according to embodiments of the present disclosure.

FIG. 12 illustrates the mining of differentially methylated regions (DMRs) fulfilling the second selection criteria according to embodiments of the present disclosure. In contrast to the previous section, we have included more than one case per disease (NPC in this analysis) for mining of the DMRs. The second selection criteria corresponds to: (1) non-overlapping, contiguous window of 500 bp in size and (2) methylation percentages of the CpG sites within the region less than 80% in the selected case of infectious mononucleosis (TBR1748) and greater than 90% in both cases of nasopharyngeal carcinoma (TBR1416 and FD089). Each data point in FIG. 12 represents the average methylation percentage of all the CpG site within the 500-bp regions across the EBV genome in the IM subject (on the x-axis) and the corresponding average methylation percentage of the same region in the two NPC subjects (on the y-axis).

In FIG. 12, the methylation percentage for the NPC subject is shown on the vertical axis, and the methylation percentage for the IM subject is shown on the horizontal axis. Vertical line 1201 shows the cutoff of 80% for the methylation percentage in the case of IM. Horizontal line 902 shows the cutoff of 90% in the case of NPC. With this second selection criteria defined above, we identified a total of 46 DMRs which comprised of 1,520 CpG sites (approximately 20% of the total CpG sites within the EBV genome being captured with our probes). The 46 DMRs are shown in the upper left section (generally marked as region 1210).

Figure 13:
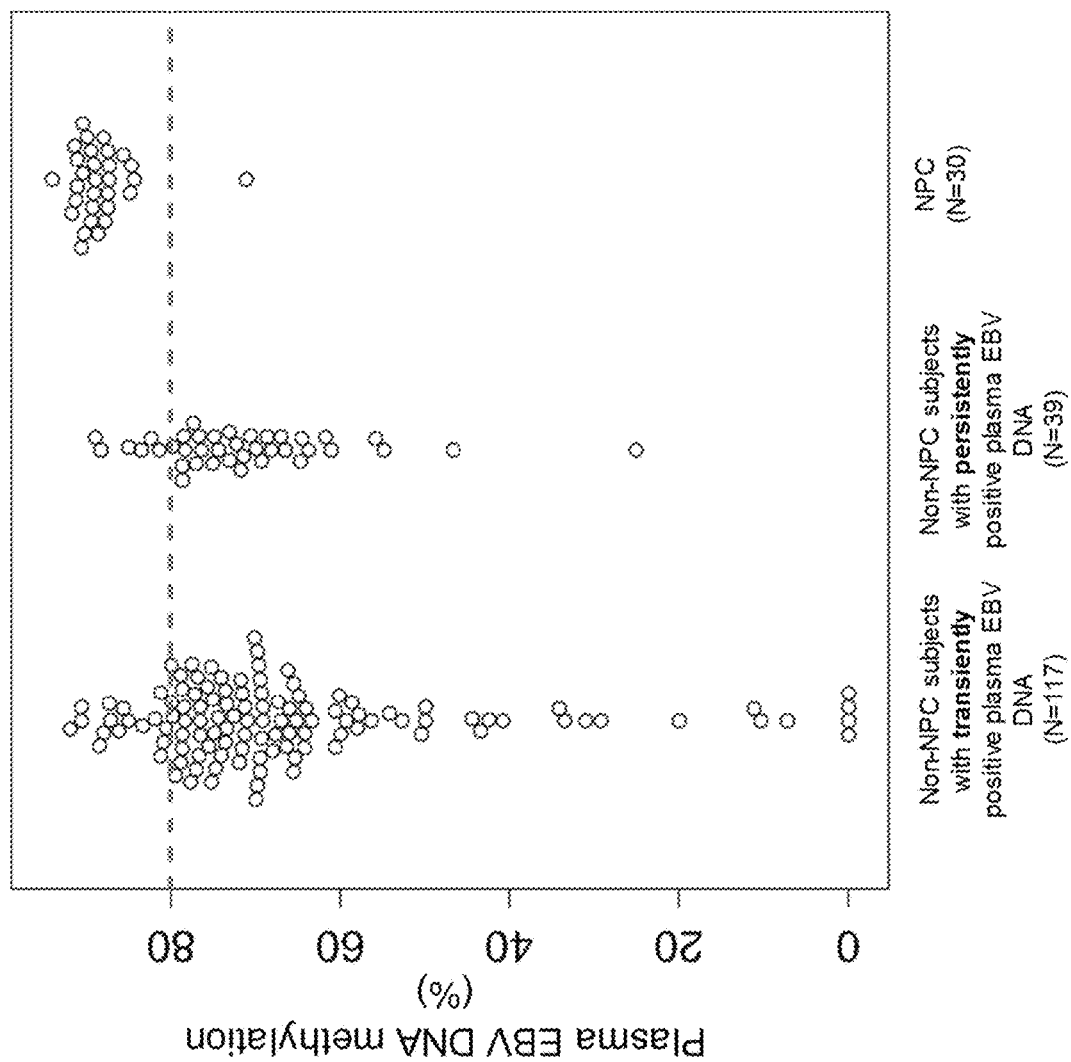
FIG. 13 shows the methylation percentages of plasma EBV DNA based on the 46 DMRs defined in FIG. 12 in the non-NPC subjects with transiently positive plasma EBV DNA, non-NPC subjects with persistently positive plasma EBV DNA, and NPC patients according to embodiments of the present disclosure.

FIG. 13 shows the methylation percentages of plasma EBV DNA based on the 46 DMRs defined in FIG. 12 in the non-NPC subjects with transiently positive plasma EBV DNA, non-NPC subjects with persistently positive plasma EBV DNA, and NPC patients according to embodiments of the present disclosure. Each data point corresponds to a different subject. The classifications of transiently positive and persistently positive are determined as described above, i.e., based on numbers of EBV DNA reads taken from samples at two times.

We analyzed 117 non-NPC subjects with transiently positive plasma EBV DNA, 39 non-NPC subjects with persistently positive plasma EBV DNA, and 30 NPC patients by targeted bisulfite sequencing. All the non-NPC subjects and NPC patients were recruited from the prospective screening cohort. We compared the methylation percentages of plasma EBV DNA based on the DMRs defined above (FIG. 12) among the three groups. The methylation percentages are determined as a single value using sequence reads that correspond (e.g., align) to the 1,520 sites in the set of 46 DMRs.

In one embodiment, different weighting could be assigned to the various DMRs for the calculation of the aggregated methylation percentage. Such weightings can be implemented in various ways, e.g., a scaling factor for each methylated sequence read at a site (e.g., multiplying by a factor greater than 1 when a region is to be weighted higher) or a scaling factor can be applied to region methylation percentages, thereby providing a weighted average of region methylation percentages. In this example, we applied equal weighting for all the DMRs defined.

The mean methylation percentage of plasma EBV DNA based on the 46 DMRs for the NPC group (mean=88.3%) was significantly higher than the mean methylation percentages of the other two non-NPC groups with transiently positive (mean=65.3%) and persistently positive (mean=71.1%) plasma EBV DNA ($p<0.0001$, Kruskal-Wallis test). Accordingly, NPC patients could be differentiated from non-NPC subjects with detectable plasma EBV DNA (transiently or persistently positive) based on the difference in the methylation profiles of plasma EBV DNA (e.g., as represented by methylation percentages of plasma EBV DNA based on DMRs).

In this example and in other embodiments described herein, the reference levels for discriminating between classifications can be determined in various ways. In one embodiment, the cutoff value (reference level) used to discriminate between a subject having NPC and not having NPC can be the lowest value in the EBV DNA methylation percentages among the NPC patients being analyzed (training set). In other embodiments, the cutoff values can be determined, for example, as the mean EBV DNA methylation percentages of the NPC patients minus one standard deviation (SD), mean minus two SD, mean minus three SD. In yet other embodiments, the cutoff can be determined using Receiver Operator Characteristics (ROC) curves or by nonparametric methods, for example but not limited to including 100%, 95%, 90%, 85%, 80% of the NPC patients being analyzed.

In the current example, a cutoff value of 80% in the methylation percentage can be set to achieve a sensitivity of greater than 95% for NPC detection. Using this cutoff value of 80%, 29 out of the 30 patients with NPC, 16 out of 119 non-NPC subjects with transiently positive plasma EBV DNA, and 6 out of 39 non-NPC subjects with persistently positive plasma EBV DNA had their methylation percentages of plasma EBV DNA, determined within the 46 defined DMRs by targeted bisulfite sequencing, higher than the cutoff value (80%). The calculated sensitivity, specificity, and positive predictive value were 96.7%, 85.9% and 58.5% respectively.

C. Representative Methylation Consensus Regions of Same Condition

In the examples below, we aimed to identify regions that have similar methylation densities across subjects with a same condition. We define such regions to be representative methylation consensus regions for a condition. In some implementations, such a criteria can also be combined with criteria of differential methylation among conditions.

To demonstrate the identification of 'representative' methylation consensus regions, we randomly selected two patients with NPC (TBR1392 and TBR1416). Here, we divided the EBV genome into non-overlapping regions of 500 bp. In other embodiments, different sizes of overlapping regions could be set. For examples, the sizes of the overlapping regions could be set at 50 bp, 100 bp, 200 bp, 300 bp, 400 bp, 600 bp, 800 bp and 1000 bp. Within the 500-bp regions, we calculated the average methylation percentages of all CpG sites within the region in the two patients with NPC (TBR1392 and TBR1416).

Figure 14:
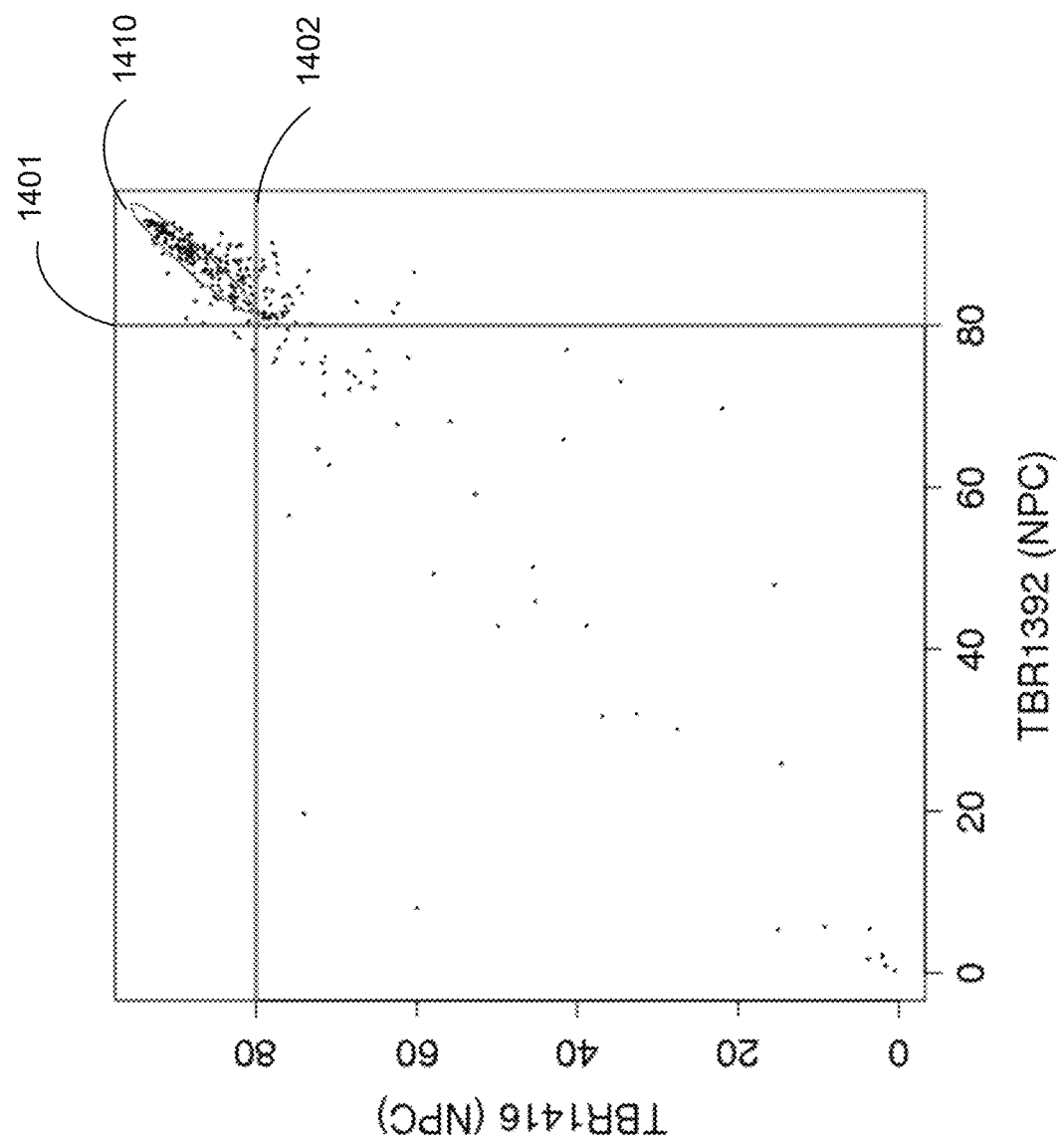
FIG. 14 illustrates the mining of representative methylation consensus regions fulfilling third selection criteria according to embodiments of the present disclosure

FIG. 14 illustrates the mining of representative methylation consensus regions fulfilling third selection criteria according to embodiments of the present disclosure. The third selection criteria corresponds to: (1) non-overlapping, contiguous window of 500 bp in size, (2) differences in the overall methylation density of the region less than 1% between the two cases of NPC, and (3) overall methylation density of the region greater than 80% for both cases.

In other embodiments, the 'representative' methylation consensus region could be defined if the differences in methylation percentages between the two NPC patients are less than 2%, 3%, 4%, 5%, 6%, 7%, 8%, 9% or 10% between the two NPC cases and the methylation percentages are greater than 10%, 20%, 30%, 40%, 50%, 60%, 70% or 90%. More than two subjects per disease can be used to define the 'representative' methylation consensus regions, e.g., the methylation percentages for each of the subjects being within the specified similarity cutoff (e.g., 1%) and being within a specified range for methylation percentage (e.g., greater than 80%).

Each data point in FIG. 14 represents the methylation percentage of a 500-bp region across the EBV genome in on NPC subject (on the x-axis) and the corresponding methylation percentage of the same region in the other NPC subject (on the y-axis). With the selection criteria defined above, we have identified 79 regions. These 79 DMRs can be found in region 1410 in FIG. 14.

In FIG. 14, the methylation percentage for the first NPC subject is shown on the vertical axis, and the methylation percentage for the second NPC subject is shown on the horizontal axis. Vertical line 1401 shows the cutoff of 80% for the methylation percentage in the case of IM. Horizontal line 1402 shows the cutoff of 80% in the case of NPC. Thus, the regions in the upper right section (generally marked as region 1410) correspond to the DMRs for this example.

Figure 15:
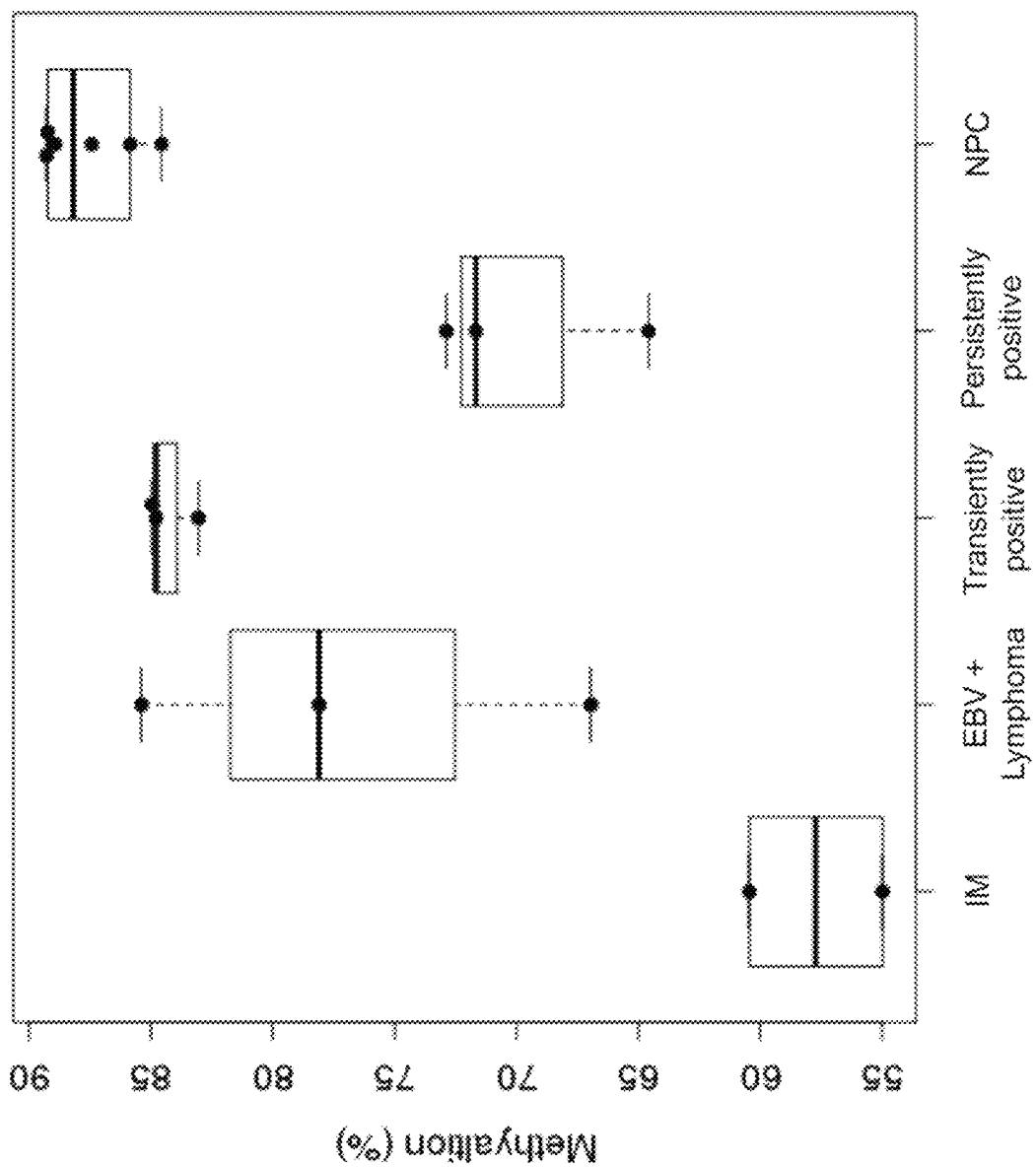
FIG. 15 shows the methylation percentages of plasma EBV DNA based on the 'representative' CpG sites described in FIG. 12 in the same group of subjects with infectious mononucleosis (IM) (n=2), EBV-associated lymphoma (n=3), transiently positive plasma EBV DNA (n=3), persistently positive plasma EBV DNA (n=3), and NPC (n=6) according to embodiments of the present disclosure.

FIG. 15 shows the methylation densities of plasma EBV DNA based on the 'representative' methylation consensus regions defined above (FIG. 12) in the same group of subjects with infectious mononucleosis (IM) (n=2), EBV-associated lymphoma (n=3), transiently positive plasma EBV DNA (n=3), persistently positive plasma EBV DNA (n=3), and NPC (n=6) according to embodiments of the present disclosure. We could observe a statistically significant difference in the methylation percentages among the groups (p-value=0.00371, one-way ANOVA test). Based on these data, one can determine the status of a tested sample by analyzing the methylation densities of the plasma DNA for the representative methylation consensus regions. For example, a methylation density of 90% would indicate that the sample is collected from a patient with NPC whereas a methylation of density of 80% is suggestive that the sample is from a patient with EBV-positive lymphoma.

D. Single CpG Site Analysis

Besides calculating an aggregate methylation level based on a set of sites (e.g., as described in sections above), embodiments can calculate the methylation percentage based on individual CpG sites within the EBV genome. To identify individual CpG sites with differential methylation levels in different EBV-associated diseases, we pooled the sequencing data of plasma DNA reads of 3 subjects with persistently positive EBV DNA, but without NPC, giving a sequencing depth of 7×. We then compared the methylation percentages of all the CpG sites between the pooled sequencing data of 3 subjects with persistently positive EBV DNA and 3 patients with NPC (A0050, TBR1392 and TBR1416). The pooling of the sequencing data means that the methylation percentage was determined as if all the sequence reads were from a same subject.

In various embodiments, these individual CpG sites with differential methylation levels could be defined if the methylation percentages of the CpG sites are less than 10%, 20%, 30%, 40%, 50%, 60%, 70%, 80% or 90% in one case (subject) of a disease and greater than 10%, 20%, 30%, 40%, 50%, 60%, 70%, 80% or 90% in one case of another disease. The criteria can apply to more than one case per disease to define the DMR, e.g., as described above for examples using regions, as may be done with different ranges for different conditions as well as specific separations between subjects with a different (greater than) or a same condition (within a threshold).

Appendix A shows the list of individual CpG sites across the EBV genome with differential methylation levels, when the differences in the methylation percentages over these CpG sites between the pooled sequencing data of 3 subjects with persistently positive EBV DNA and the 3 patients with NPC are greater than 20%. Those sites marked with * have a difference greater than 40%,  have a difference greater than 60% and * have a difference greater than 80%. In other embodiments, the CpG sites with differential methylation levels could be defined with the difference in methylation percentages larger than 20%, 30%, 50%, 70% or 90%. Some example sites having a difference greater than 60% are now analyzed.

Figure 16:
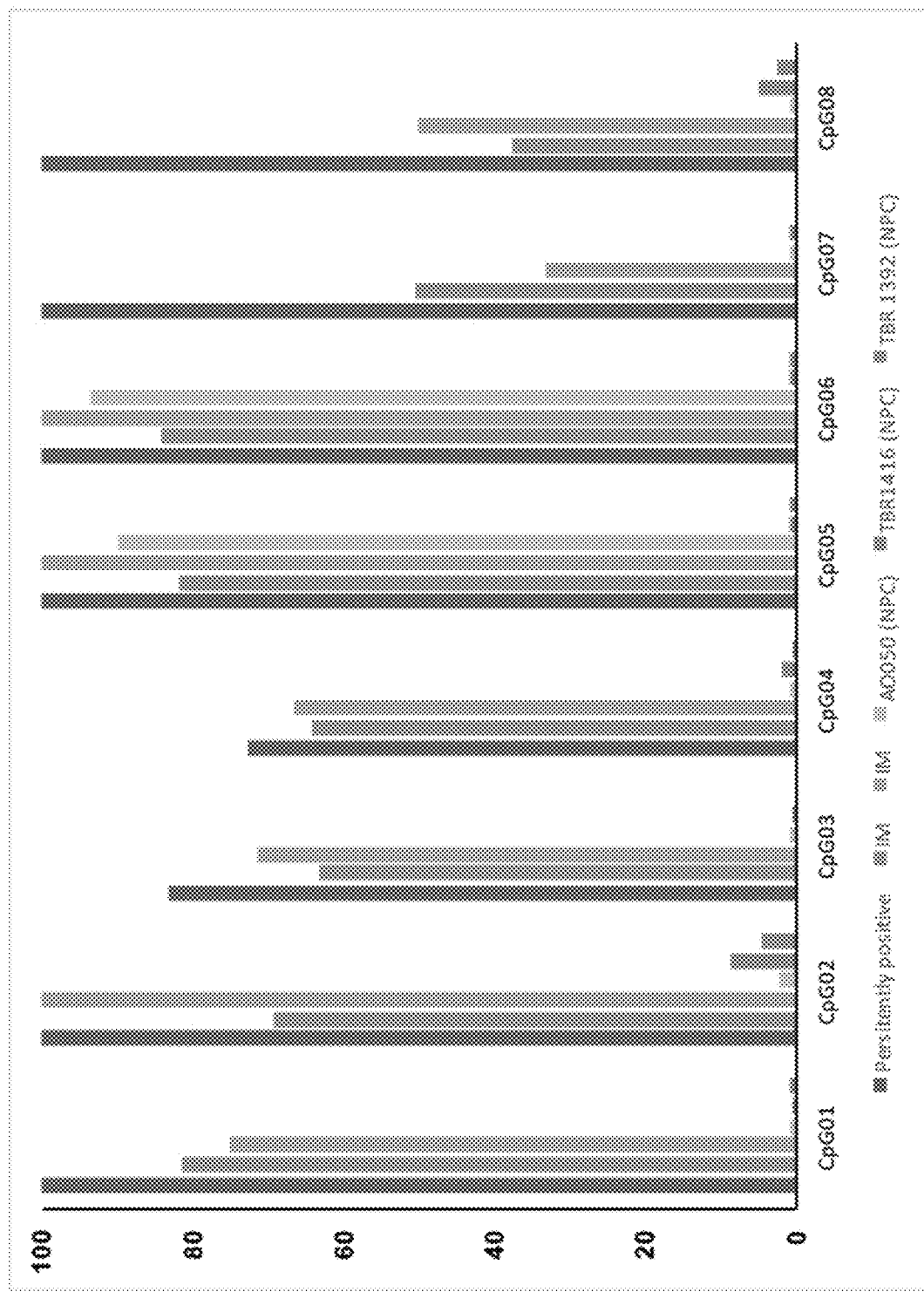
FIG. 16 shows examples of CpG sites with the methylation percentages over the sites greater than 80% in the pooled sequencing data of the 3 cases with persistently positive plasma EBV DNA and an average of less than 20% in the 3 subjects with NPC according to embodiments of the present disclosure.

FIG. 16 shows examples of CpG sites with the methylation percentages over the sites greater than 80% in the pooled sequencing data of the 3 cases with persistently positive plasma EBV DNA and an average of less than 20% in the 3 subjects with NPC according to embodiments of the present disclosure. The methylation percentages over these sites of two patients with infectious mononucleosis were also included. The methylation percentages are provided on the vertical axis, and the horizontal axis lists 8 separate sites satisfying the criteria. The sites are labeled with sequential numbers.

As can be seen, all of the sites provide a good separation between the non-NPC subjects (including persistently positive and IM) and two of the NPC subjects (TBR1416 and TBR1392). For NPC subject A0050, sites 1-4, 7, and 8 provide good separation, but sites 5 and 6 do not. Thus, individual differentially methylated sites (e.g., not just as a region) determined to discriminate between two conditions can also be used to discriminate between one condition (NPC) and two or more conditions.

Figure 17:
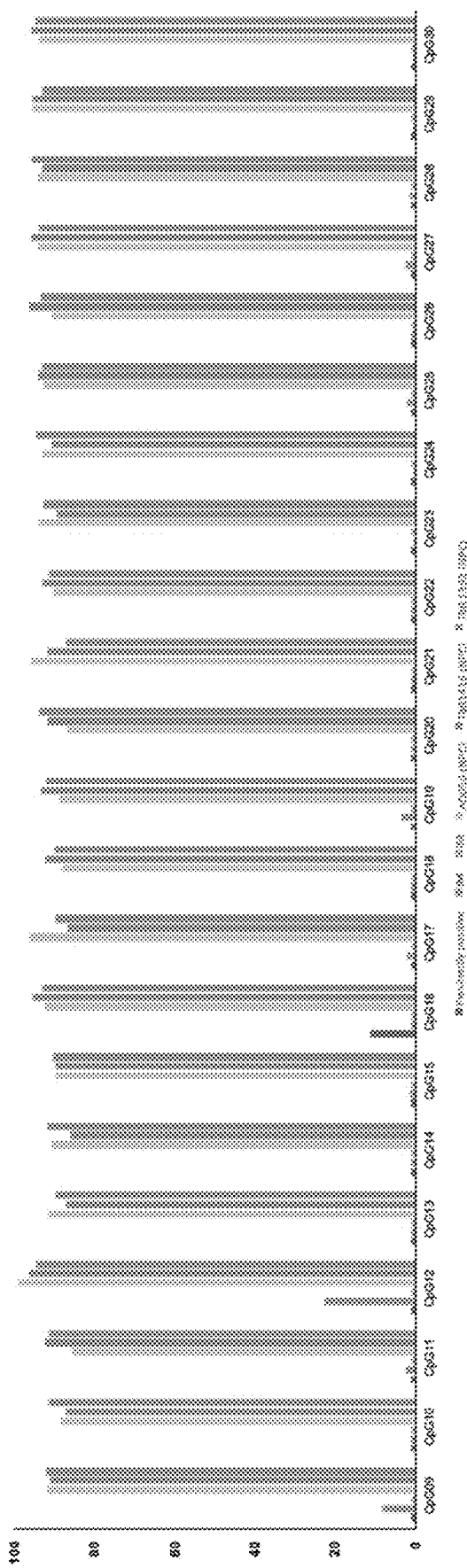
FIG. 17 shows examples of CpG sites with the methylation percentages over the sites less than 20% in the pooled sequencing data of the 3 cases with persistently positive plasma EBV DNA and greater than 80% in the 3 subjects with NPC according to embodiments of the present disclosure.

FIG. 17 shows examples of CpG sites with the methylation percentages over the sites less than 20% in the pooled sequencing data of the 3 cases with persistently positive plasma EBV DNA and greater than 80% in the 3 subjects with NPC according to embodiments of the present disclosure. The methylation percentages over these sites of two patients with infectious mononucleosis are also shown. This criteria is the opposite of those used for FIG. 16. The methylation percentages are provided on the vertical axis, and the horizontal axis lists 22 separate sites satisfying the criteria. The sites are labeled with sequential numbers.

As can be seen, all of the sites provide a good separation between the non-NPC subjects (including persistently positive and IM) and the NPC subjects. This shows that individual sites can be used to discriminate between classifications. And, sites can be selected from across the viral genome, as opposed to being within a same contiguous region of a specified length. More sites can be selected to provide greater statistical accuracy, e.g., so that more EBV DNA fragments can be detected.

In one embodiment, multiple CpG sites with differential methylation levels (e.g., those defined in Appendix A and FIGS. 16 and 17) are chosen to be within a specified distance to each other. In this manner, individual viral DNA fragments may each cover the multiple sites. For example, the specified distance can be 150 bp because this is approximately the representative size of a plasma DNA molecule. In such situation, targeted amplification of the particular region with multiple differentially methylated CpG sites by PCR amplification would be possible. This targeted analysis would be of lower cost than using genome-wide analysis approach.

Accordingly, in various embodiments, the analysis of methylation pattern can be based on the genomic regions of the whole viral genome or individual CpG sites. In such a region analysis, the viral genome can be divided into different regions based on the genomic coordinates, with each region including all the CpG sites within such a region. Alternatively, differentially methylated CpG sites can first be selected and then merged within a region to form a DMR. In another example, all CpG sites may be included in the calculation of the methylation density of the region without prior selection of the informative ones.

E. Hierarchical Clustering Analysis

Some embodiments may use more than methylation level to discriminate between classifications. In one example, clustering techniques may be used. In such clustering techniques, multiple methylation levels can be determined for each subject, e.g., methylation levels for different regions (each including one or more sites), methylation levels for individual sites, or combinations thereof. In some embodiments, the clustering can be hierarchical.

The set of methylation levels can form a vector that represents a multidimensional data point having a length that equals the number of methylation levels. The regions (bins) can be of various sizes, as described herein. And, the clustering analysis can be based on non-overlapping contiguous bins of different sizes. For examples, the sizes of bins could be defined at 50 bp, 100 bp, 200 bp, 300 bp, 400 bp, 500 bp, 600 bp, 700 bp, 800 bp, 900 bp or 1000 bp. Accordingly, the clustering analysis can be based on comparisons of the methylation levels for different sites/bins to corresponding methylation levels among the different subjects.

Figure 18:
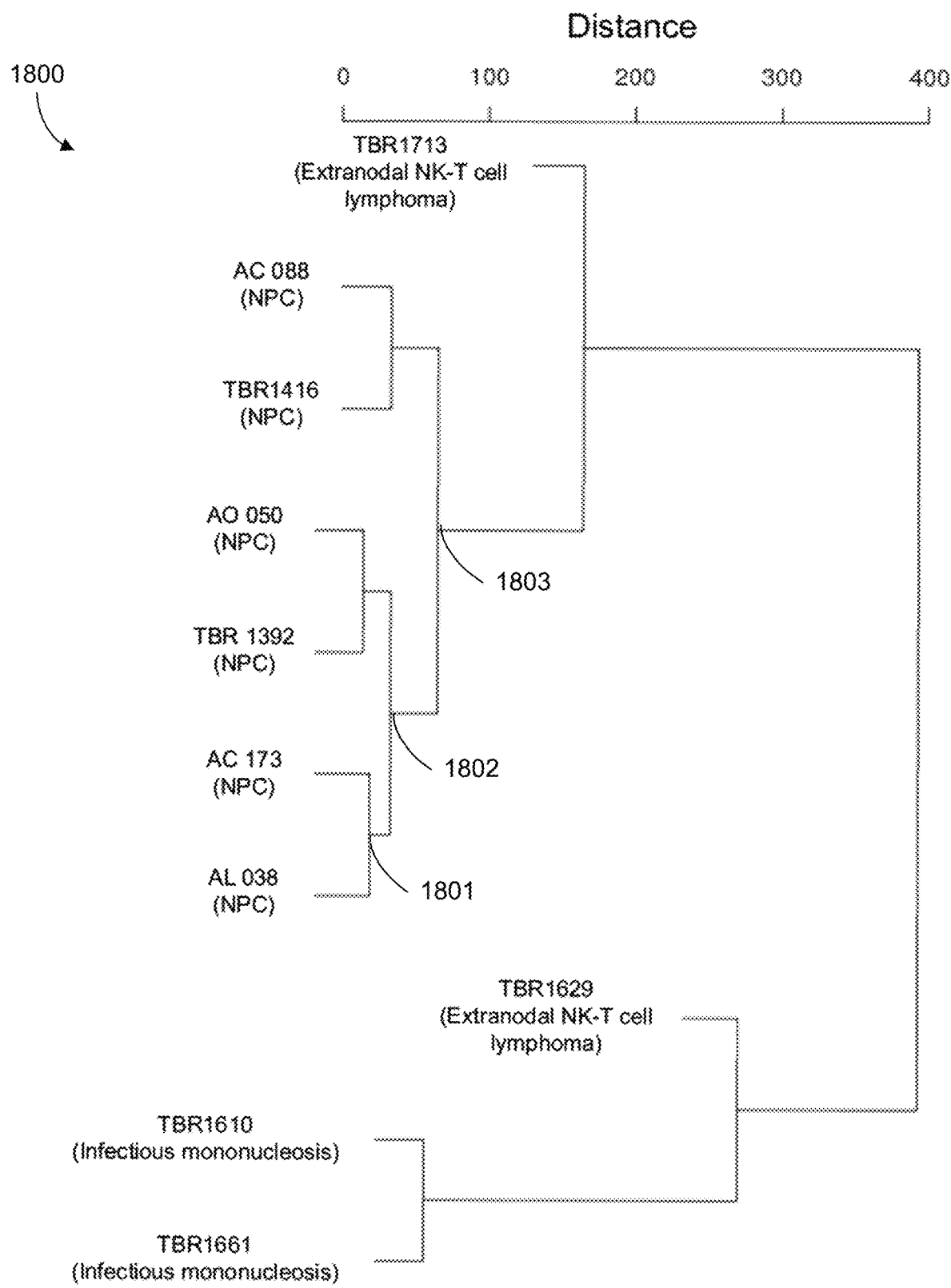
FIG. 18 shows a cluster dendrogram with the hierarchical clustering analysis based on methylation pattern analysis of plasma EBV DNA for 6 patients with NPC (including 4 patients with early stage disease from our screening cohort), 2 patients with extranodal NK-T cell lymphoma, and 2 patients with infectious mononucleosis according to embodiments of the present disclosure.

FIG. 18 shows a cluster dendrogram with the hierarchical clustering analysis based on methylation pattern analysis of plasma EBV DNA for 6 patients with NPC (including 4 patients with early stage disease from our screening cohort), 2 patients with extranodal NK-T cell lymphoma, and 2 patients with infectious mononucleosis according to embodiments of the present disclosure. In this example, the hierarchical clustering analysis was based on comparison of the methylation percentages of the CpG sites within non-overlapping contiguous regions of 500 bp in size. The clustering groups the different subject based on differences in the methylation percentages for the different regions, where the differences can be combined to provide a distance.

In FIG. 18, the distance is shown along the top horizontal axis. The distance can be determined as a sum of differences between each of the methylation densities (percentages), e.g., when the methylation densities at different loci corresponds to a vector representing a multi-dimensional point, where the distance is between two multi-dimensional points. Two subjects are combined at a point equal to the distance between them. When a new patient is tested, the new multidimensional point of methylation percentages (or other level) is used to determine a closest one of the reference subjects (e.g., those shown in FIG. 18) or a closest subgroup, as depicted at a node, e.g., nodes 1801 or 1802. The identification of a closest reference subject or reference node can provide the classification.

Cluster dendrogram 1800 shows that the NPC subject are incrementally clustered together, with all of the NPC subject being clustered into a subgroup at node 1803, which does not include subjects with other conditions. This shows an ability to discriminate the NPC subjects from the IM subjects and the lymphoma subjects. Similarly, the IM subjects are grouped together. Of note, the two NK-T cell lymphoma patients were not clustered together. Patient 1629 had stage IV disease and patient 1713 had stage I disease. This may indicate that the methylation pattern would progress across different stage of the same disease. One potential application of this would be using the methylation profile for staging and prognosticating the patients.

We have demonstrated the feasibility of differentiating among different EBV-associated diseases based on clustering analysis through methylation patterns of plasma EBV DNA. For example, after a certain pattern is identified, embodiments can rule-in or rule-out a disease. Other classification algorithms including but not limited to principle component analysis, linear discriminant analysis, logistic regression, machine learning models, k-means clustering, k-nearest neighbors and random decision forests could also be used.

Figure 19:
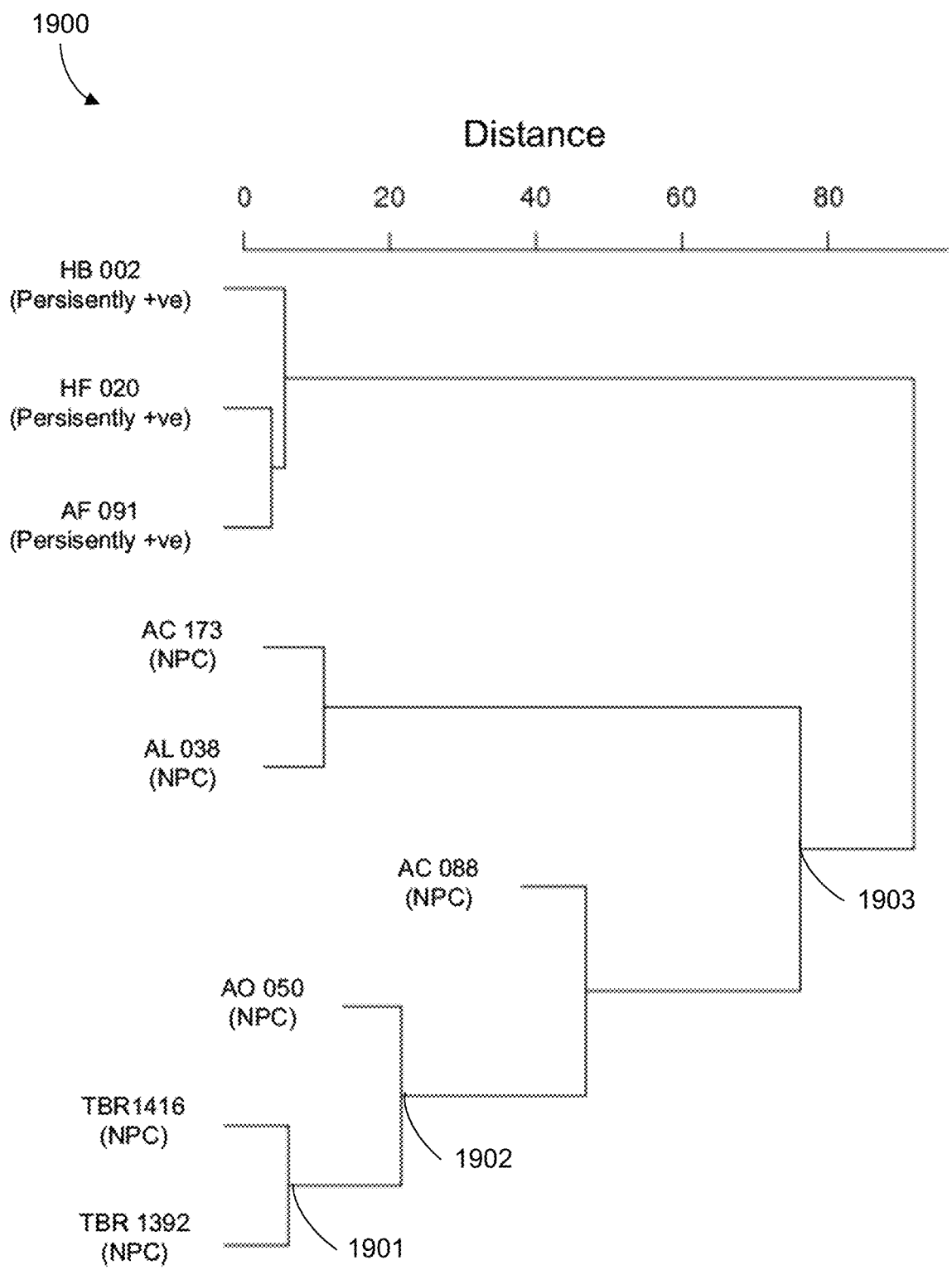
FIG. 19 shows a cluster dendrogram with the hierarchical clustering analysis based on methylation pattern analysis of plasma EBV DNA for 6 patients with NPC (including 4 patients with early stage NPC from our screening cohort) and 3 non-NPC subjects with persistently positive plasma EBV DNA according to embodiments of the present disclosure.

FIG. 19 shows a cluster dendrogram with the hierarchical clustering analysis based on methylation pattern analysis of plasma EBV DNA for 6 patients with NPC (including 4 patients with early stage NPC from our screening cohort) and 3 non-NPC subjects with persistently positive plasma EBV DNA according to embodiments of the present disclosure. The plasma DNA was extracted from their first blood samples upon recruitment. In this example, the hierarchical clustering analysis was based on comparison of the methylation percentages of the CpG sites within non-overlapping contiguous bins of 500 bp in size.

In FIG. 19, the distance is also shown along the top horizontal axis. The distance can be determined as described above. Similar to FIG. 18, two subjects can be combined at a point equal to the distance between them. As shown, the NPC subjects are clustered with other NPC subjects, e.g., at nodes 1901 and 1902. Cluster dendrogram 1900 shows that the NPC subject are incrementally clustered together, with all of the NPC subject being clustered into a subgroup at node 1903, which does not include subjects with other conditions (i.e., persistently positive for this example). Similarly, the persistently positive subjects are grouped together first. This shows an ability to discriminate the NPC subjects from the persistently positive subjects.

Accordingly, we have demonstrated the feasibility of differentiating the patients with early stage NPC from the non-NPC subjects with false positive plasma EBV DNA results based on methylation pattern analysis of plasma EBV DNA from the first blood sample without the need for serial analysis. That is, an accurate classification can be made with a single measurement, as opposed to requiring multiple measurements at different times. This would potentially save the medical costs in the logistic arrangement for serial blood tests and further investigations for confirmatory purpose.

Figure 20:
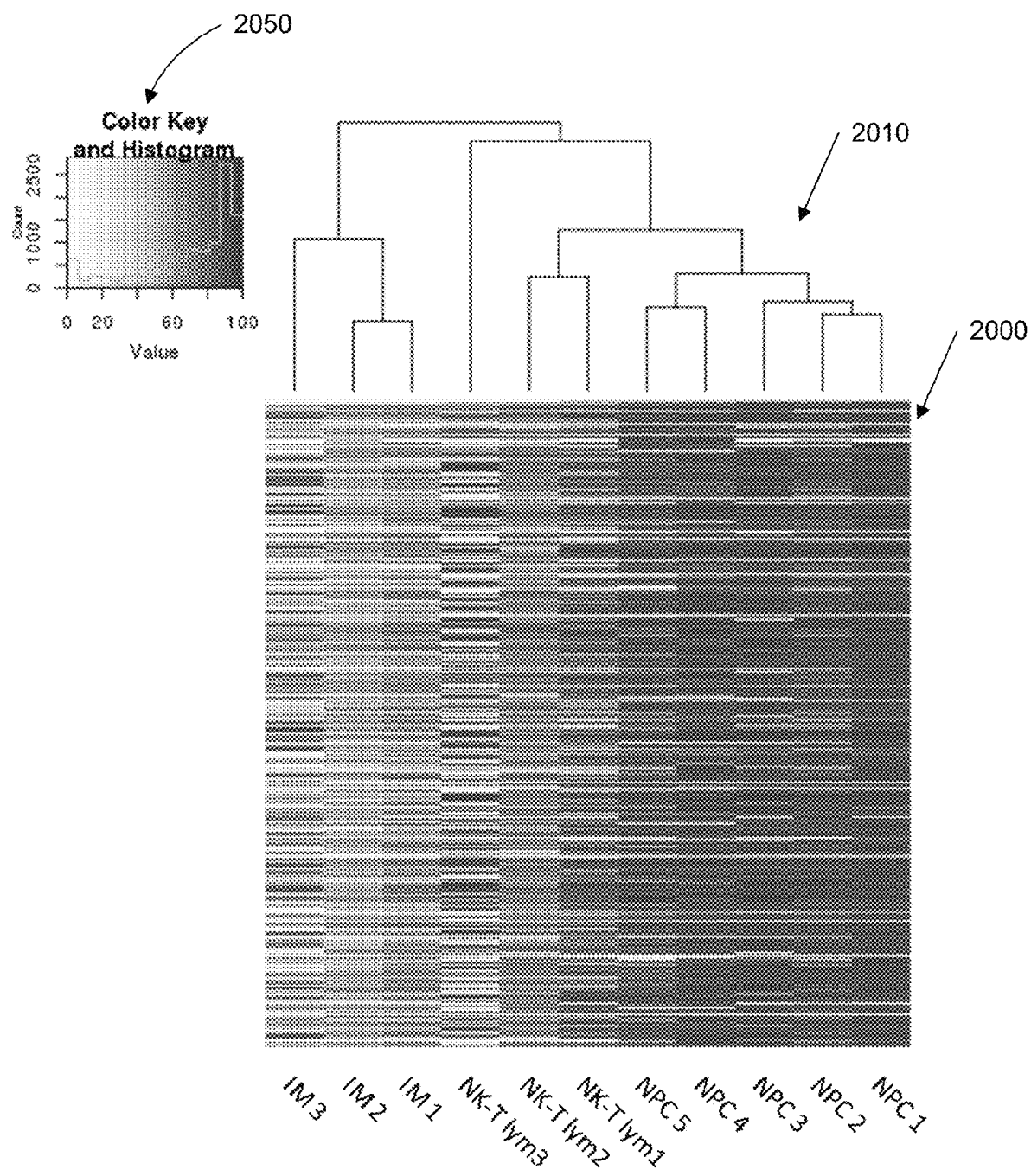
FIG. 20 shows a heatmap 2000 illustrating the methylation levels of all the non-overlapping 500-bp regions in the whole EBV genome for patients with nasopharyngeal carcinoma, NK-T cell lymphoma, and infectious mononucleosis.

FIG. 20 shows a heatmap 2000 illustrating the methylation levels of all the non-overlapping 500-bp regions in the whole EBV genome for patients with nasopharyngeal carcinoma, NK-T cell lymphoma, and infectious mononucleosis. The methylation level of each window was calculated as the average of the methylation densities of all CpG sites (without selection) within the window. We analyzed the methylation patterns of plasma EBV DNA for 5 patients with NPC, 3 patients with NK-T cell lymphoma and 3 patients with infectious mononucleosis. In the current example, the methylation pattern is analyzed through the methylation percentages over all 500-bp non-overlapping windows. Color key/histogram 2050 shows different colors for different methylation percentages, with white being near zero, yellow being low (e.g., ~20%), orange being medium (e.g., ~50%), and red being high (e.g., ~80% and higher). Color key/histogram 2050 also shows a histogram for the number of regions having a particular methylation level.

Heatmap 2000 shows the methylation levels across all the non-overlapping 500-bp window on EBV genome for all the cases. Each row represents one 500-bp region and the color represents its methylation level. Each column represents one case. Cluster dendrogram 2010 shows clustering of the different cases. Different cases with the same diagnosis were clustered together. For example, the NPC cases are all clustered on the right, and exhibit high methylation levels, as evidenced by the dark red. The lymphoma subjects are clustered in the middle and have a mix between yellow (low methylation levels) and red (high methylation levels). The cluster of infectious mononucleosis samples are shown on the left and exhibit relatively low methylation levels, as evidenced by the light yellow.

FIG. 20 demonstrates the feasibility of predicting the EBV-associated diseases through the analysis of the methylation patterns of plasma EBV DNA. Further, greater accuracy is seen using the DMRs as opposed to all regions spanning the EBV genome.

In other embodiments, the methylation patterns can be derived through the methylation percentages over all the CpG sites across the EBV genome (as genomewide analysis), e.g., on a per site bases. In another embodiment, different weighting could be assigned to any individual CpG site(s) and/or DMR(s) for prediction of the EBV-associated diseases or conditions. Such weightings can be implemented in various ways, as is described above, e.g., applying scaling factors (weights) to intermediate methylation levels to obtain a weighted average for a region or genomewide. Here, we assigned equal weighting for all the CpG sites being analyzed.

V. Use of Counts and Size

In addition to using methylation levels of cell-free viral DNA fragments in a cell-free sample to discriminate among subjects with different conditions and/or levels of a condition, some embodiments can use sizes of cell-free viral DNA fragments in a cell-free sample. Some embodiments can also use a number (e.g., a proportion) of cell-free viral DNA fragments in a cell-free sample. Various embodiments can use combinations of different techniques, e.g., by requiring a same classification for a subject using each of the techniques. For example, any combination of a) the proportion of plasma DNA fragments aligning to the EBV, b) the size profile of the plasma EBV DNA fragments, and c) the methylation profile of plasma EBV DNA, can be used for the classification. Different thresholds can be adopted for the classification when different techniques are combined to achieve the desired diagnostic sensitivity and specificity.

A. Size Profile Analysis of Plasma EBV DNA Fragments

In addition to the feasibility of methylation analysis of plasma EBV DNA fragments, the size of each plasma EBV DNA fragment was deduced based on the coordinates of the outmost nucleotide at the two ends in the EBV genome. The size distributions of cell-free EBV DNA fragments varies for different conditions (i.e., different patterns), thereby allowing discrimination among subjects with different conditions, and thus levels of a condition. These different size patterns can be quantified in various size metrics, e.g., sizes ratios of an amount of viral DNA at one size (e.g. a first size range) relative to an amount of viral DNA at another size (e.g., a second size range). For example, a size ratio can be used to compare the proportion of plasma EBV DNA reads within a certain size range (e.g., between 80 and 110 base pairs) normalized to the amount of autosomal DNA fragments within the same size range among subjects with different conditions.

Figure 21:
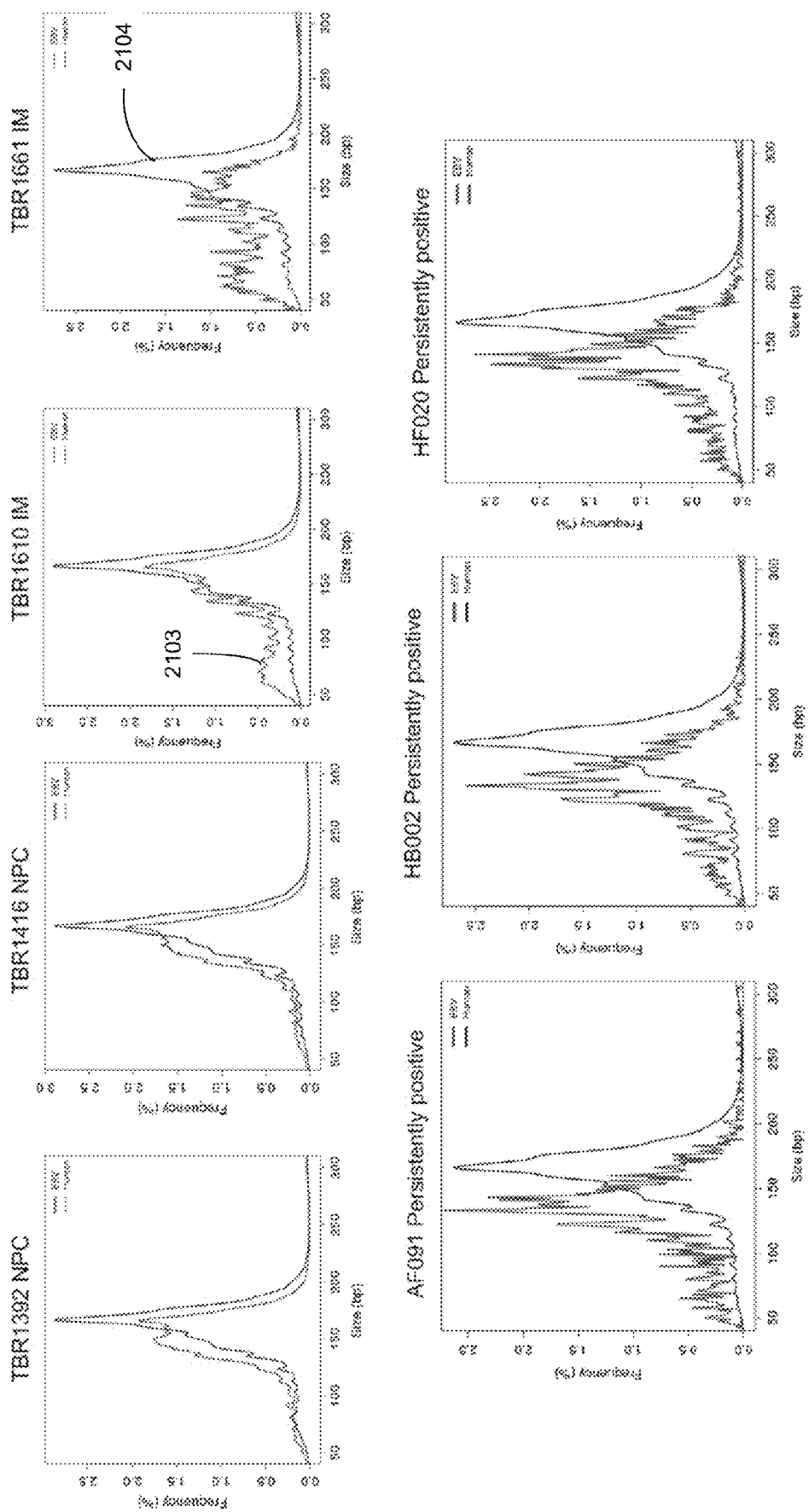
FIG. 21 shows the size profiles of size distribution of sequenced plasma DNA fragments mapped to the EBV genome and human genome in 2 patients with NPC (TBR1392 and TBR1416) and 2 patients with infectious mononucleosis (TBR1610 and TBR1661), and 3 non-NPC subjects with persistently positive plasma EBV DNA on serial analysis (AF091, HB002 and HF020) according to embodiments of the present disclosure.

FIG. 21 shows the size profiles of size distribution of sequenced plasma DNA fragments mapped to the EBV genome and human genome in 2 patients with NPC (TBR1392 and TBR1416) and 2 patients with infectious mononucleosis (TBR1610 and TBR1661), and 3 non-NPC subjects with persistently positive plasma EBV DNA on serial analysis (AF091, HB002 and HF020) according to embodiments of the present disclosure. The plots show a sizes (bp) along the horizontal axis and frequency (proportion) of DNA at a given size in the vertical axis. The size distributions of the human genomic DNA is shown in blue, e.g., in size distribution 2104. The EBV size distributions are shown in red, e.g., size distribution 2103.

A difference in the size profile pattern of plasma EBV DNA fragments aligned to the EBV genome and those aligned to the autosomal genome were observed. For example, the NPC subjects have a shift to smaller cell-free EBV DNA fragments at the peak around 160 bp with a similar amount of fragments at the lower end as human DNA, while IM subjects have a larger amount of EBV DNA than human DNA below 100 bp. The persistently positive subjects have significant fluctuations up and down as size increases, as well as a more pronounced shift of the peak relative to the NPC subjects. These differences can be used to differentiate subjects with different conditions, e.g., differentiate subjects with NPC from subjects with false-positive plasma EBV DNA results.

To compare the proportion of plasma EBV DNA reads within a certain size range (e.g., between 80 and 110 bp) among individuals, the amount of plasma EBV DNA fragments can be normalized to the amount of autosomal DNA fragments within the same size range. This metric is an example of a size ratio. A size ratio can be defined by the proportion of plasma EBV DNA fragments within a certain size range divided by the proportion of a reference set of sequences (e.g., DNA fragments from the human autosomes) within the corresponding size range. Various size ratios may be used. For example, a size ratio of fragments between 80 and 110 base pairs would be:

$$\text{Size ratio}_{80-110bp} = \frac{\text{Proportion of } EBV\ DNA \text{ fragments within } 80-110 \text{ bp}}{\text{Proportion of autosomal } DNA \text{ fragments within } 80-110 \text{ bp}}$$

Figure 22:
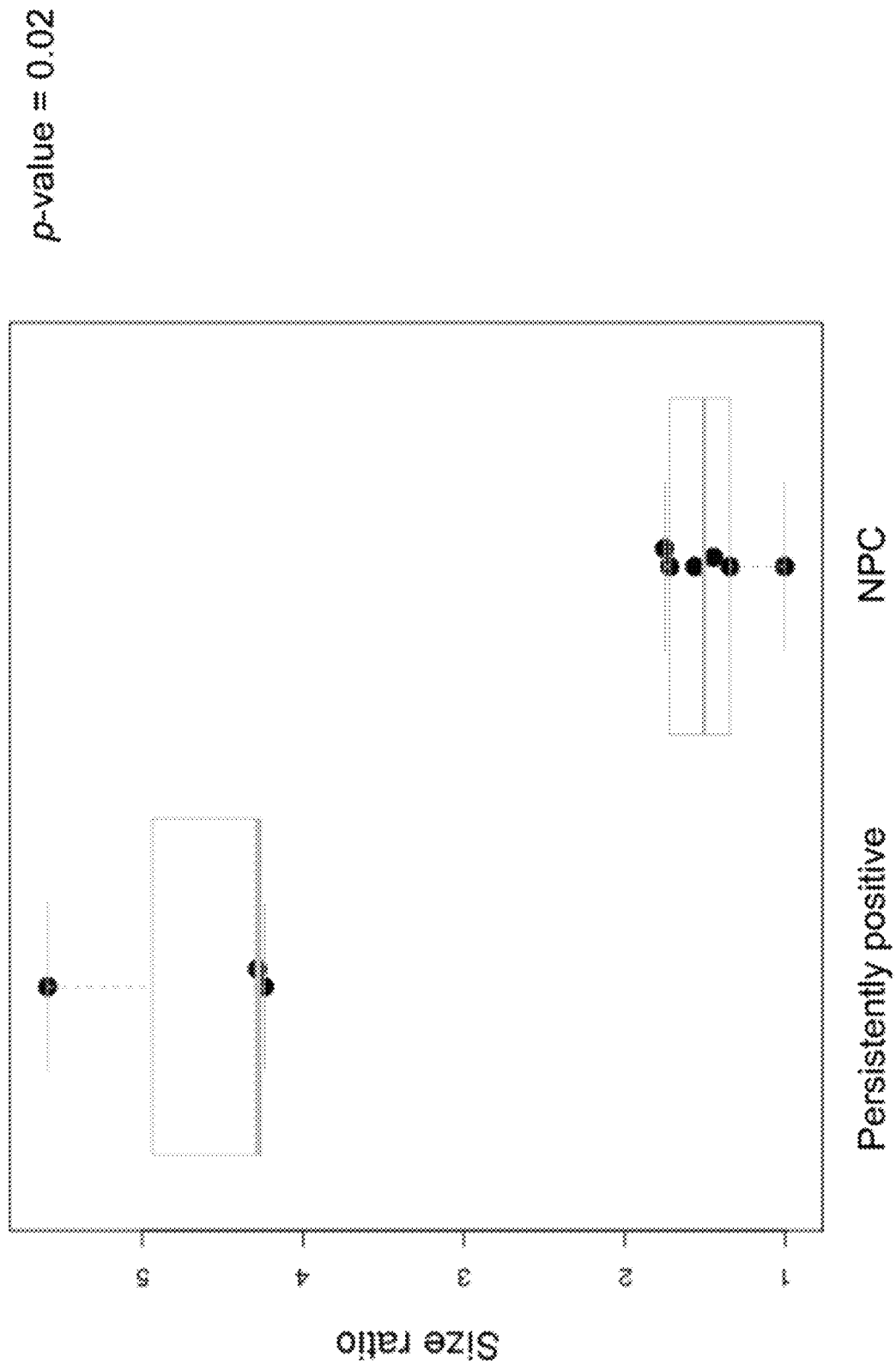
FIG. 22 shows the size ratio in 6 patients with NPC and 3 subjects that are persistently positive for plasma EBV DNA according to embodiments of the present disclosure.

FIG. 22 shows the size ratio in 6 patients with NPC and 3 subjects that are persistently positive for plasma EBV DNA according to embodiments of the present disclosure. We could observe a statistically significant difference between the size ratio of the two groups of subjects (p-value=0.02, Mann-Whitney test). Example reference size values for discriminating between NPC subjects and persistently positive subjects can be between 2-4 (e.g., 3) for this particular size ratio.

Figure 23:
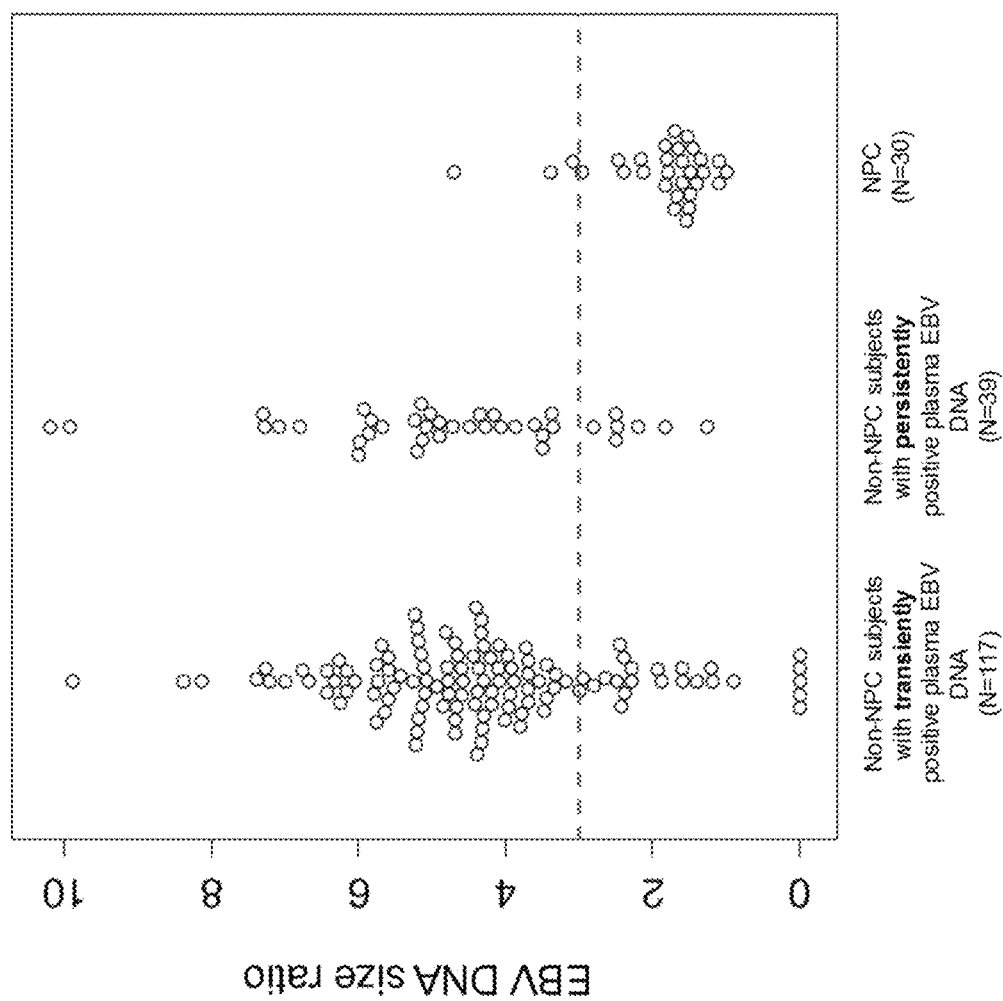
FIG. 23 shows the EBV DNA size ratios in the non-NPC subjects with transiently positive plasma EBV DNA, non-NPC subjects with persistently positive plasma EBV DNA, and NPC patients according to embodiments of the present disclosure.

FIG. 23 shows the EBV DNA size ratios in the non-NPC subjects with transiently positive plasma EBV DNA, non-NPC subjects with persistently positive plasma EBV DNA, and NPC patients according to embodiments of the present disclosure. The mean EBV DNA size ratio (80-110 bp) for the NPC group (mean=1.9) was significantly lower than the median size ratios of the other two non-NPC groups with transiently positive (mean=4.3) and persistently positive (mean=4.8) plasma EBV DNA (p<0.0001, Kruskal-Wallis test).

Accordingly, NPC patients could be differentiated from non-NPC subjects with detectable plasma EBV DNA (transiently or persistently positive) based on the difference in the size profiles of plasma EBV DNA, e.g., as represented by EBV DNA size ratios. In the current example, a cutoff value of 3 was used to achieve a detection sensitivity of 90%. Using a cutoff value of 3, 27 out of 30 patients with NPC, 23 out of 117 non-NPC subjects with transiently positive plasma EBV DNA, and 7 out of 39 non-NPC subjects with persistently positive plasma EBV DNA passed the cutoff and had their size ratios of plasma EBV DNA lower than the cutoff value. The calculated sensitivity, specificity and positive predictive value were 90%, 80.8% and 49.2% respectively.

The selection of the cutoff (reference) value can be determined in various ways. In one embodiment, a cutoff value for the EBV DNA size ratios can be selected as any value above the highest value in the EBV DNA size ratios among the NPC patients being analyzed (e.g., in a training set). In other embodiments, a cutoff values can be determined, for example, as the mean EBV DNA size ratios of the NPC patients plus one standard deviation (SD), mean plus two SD, mean plus three SD. In yet other embodiments, the cutoff can be determined using Receiver Operator Characteristics (ROC) curves or by nonparametric methods, for example, including 100%, 95%, 90%, 85%, 80% of the NPC patients being analyzed.

Other definitions of a size ratio or other statistical values of the size distribution would result in different values for each of the subjects, and thus have different reference values for discriminating among subjects. For example, a different size range can be used, or a subset of chromosomes can be used for the autosomal DNA fragments, or no autosomal DNA at all. Various statistical values of a size distribution of nucleic acid fragments can be determined. For example, an average, mode, median, or mean of a size distribution can be used. Other statistical values can be used, e.g., a cumulative frequency for a given size or various ratios of amount of nucleic acid fragments of different sizes. A cumulative frequency can correspond to a proportion (e.g., a percentage) of DNA fragments that are of a given size or smaller, or larger than a given size. Accordingly, any normalization factor (if one is used) in the denominator can be for an amount of EBV DNA for a different size range. The statistical values provide information about the distribution of the sizes of DNA fragments for comparison against one or more size thresholds for healthy control subjects or other conditions. One skilled in the art will know how to determine such thresholds based on the present disclosure. Other examples of size ratios can be found in U.S. Patent Publications 2011/0276277, 2013/0237431, and 2016/0217251.

B. Count

In addition to the analysis of methylation percentages of plasma EBV DNA, we analyzed the proportion of plasma EBV DNA reads from targeted bisulfite sequencing. The proportion of cell-free EBV DMA reads can be determined in various ways, e.g., as a proportion of all DNA reads in the human genome and several viral genomes or just of the human genome and the viral genome being analyzed. In the former example, a combined reference sequence can comprise the whole human genome (hg19), the whole EBV genome (AJ507799.2), the whole HBV genome, and the whole HPV genome. In various examples, the proportion can be determined based on counts of reads that align to the viral genome being analysed relative to the all the other DNA reads or just the ones that could be aligned (e.g., uniquely or with a specified number of mismatches). Using a reference genome of the human genome and several viral genomes, we compared the proportion of plasma EBV DNA reads among the three groups of NPC patients, non-NPC subjects with transiently positive and non-NPC subjects with persistently positive plasma EBV DNA.

Figure 24:
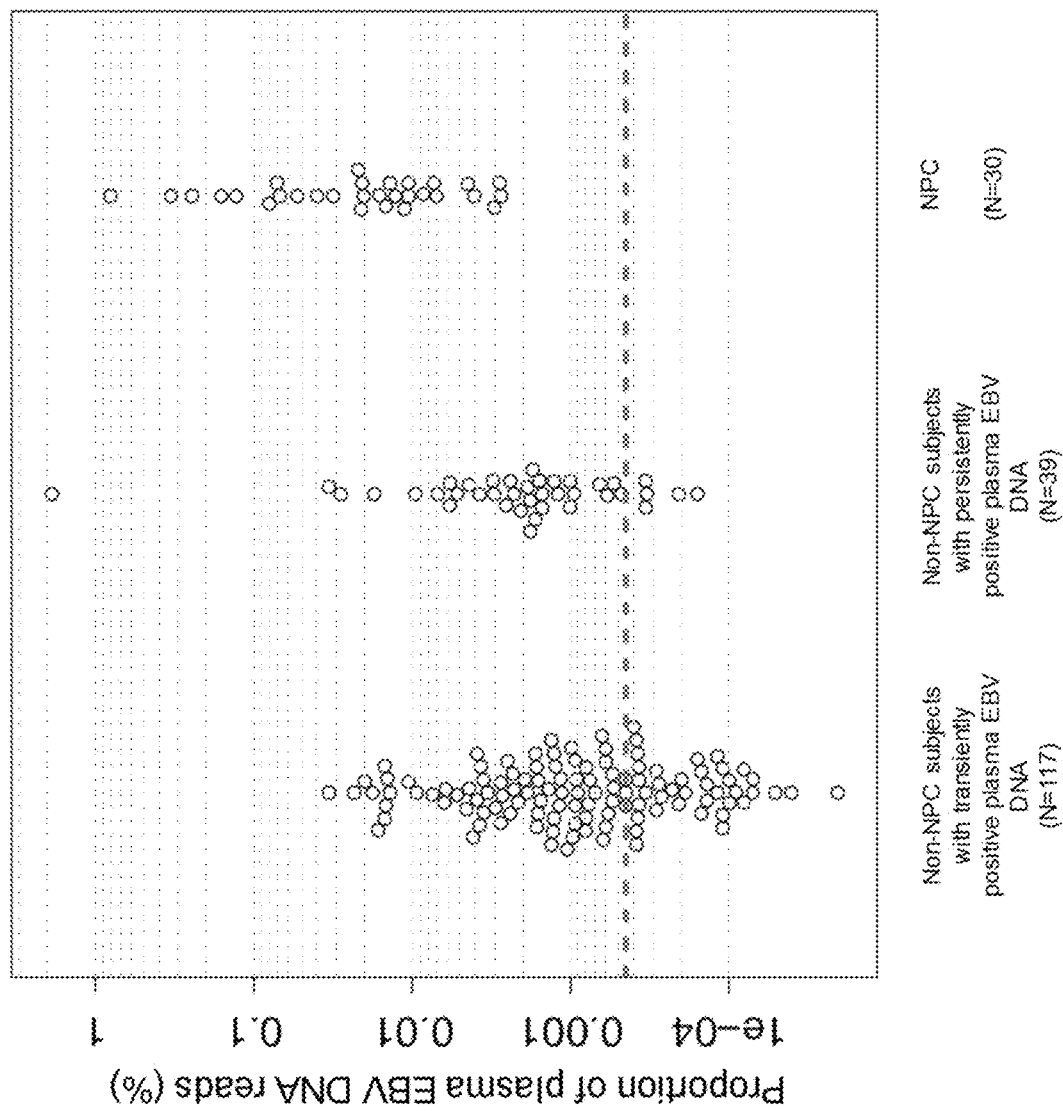
FIG. 24 shows the proportion of plasma EBV DNA reads (plasma DNA reads mapped to the EBV genome) among all sequenced plasma DNA reads in the non-NPC subjects with transiently positive plasma EBV DNA, non-NPC subjects with persistently positive plasma EBV DNA, and NPC patients according to embodiments of the present disclosure.

FIG. 24 shows the proportion of plasma EBV DNA reads (plasma DNA reads mapped to the EBV genome) among all sequenced plasma DNA reads in the non-NPC subjects with transiently positive plasma EBV DNA, non-NPC subjects with persistently positive plasma EBV DNA, and NPC patients according to embodiments of the present disclosure. The mean proportion of plasma EBV DNA reads for the NPC group (mean=0.075%) was significantly higher than the mean proportions of the other two non-NPC groups with transiently positive (mean=0.003%) and persistently positive (mean=0.052%) plasma EBV DNA (p<0.0001, Kruskal-Wallis test). Accordingly, NPC patients could be differentiated from non-NPC subjects with detectable plasma EBV DNA (transiently or persistently positive) based on the difference in the quantity of plasma EBV DNA (i.e. proportion of plasma EBV DNA).

In the current example, using a cutoff value of $4.5 \times 10^{-6}$, all the 30 patients with NPC, 79 out of 119 non-NPC subjects with transiently positive plasma EBV DNA and 34 out of 39 non-NPC subjects with persistently positive plasma EBV DNA had their proportions of plasma EBV DNA by targeted bisulfite sequencing higher than this cutoff value. The calculated sensitivity, specificity, and positive predictive value were 100%, 27.6% and 22.1% respectively The selection of the cutoff (reference) value can be determined in various ways. In one embodiment, the cutoff value for the proportion of plasma EBV DNA can be selected as any value below the lowest value in the proportion among the NPC patients being analyzed. The cutoff can be set to capture all the NPC patients and achieve the maximal sensitivity. In other embodiments, the cutoff values can be determined, for example, as the mean proportion of plasma EBV DNA reads of the NPC patients minus one standard deviation (SD), mean minus two SD, mean minus three SD. In the current example, a cutoff value was set at the mean of the proportions of plasma EBV DNA reads among all NPC patients minus three SD. In yet other embodiments, the cutoff can be determined after the logarithmic transformation of the proportion of plasma DNA fragments mapped to the EBV genome and then selected in a similar manner (e.g., using a mean, etc.). In yet other embodiments, the cutoff can be determined using Receiver Operator Characteristics (ROC) curves or by nonparametric methods, for example, including 100%, 95%, 90%, 85%, 80% of the NPC patients being analyzed.

C. Combined Analysis

These three techniques can be combined to provide increased accuracy. For example, the metrics for each of the techniques—each technique potentially including multiple metrics, e.g., multiple methylation levels—can be compared to respective reference values to classify a subject, e.g., as may be done in a decision tree or to identify the subject as corresponding to a particular section (quadrant) of a plot of training values. Clustering techniques may also be used, e.g., as described above.

We assessed the value of combining the analyses for plasma EBV DNA proportions (quantification) and size ratios for NPC identification. We also assessed the value of combining the analyses for plasma EBV DNA proportions (quantification) and methylation percentages for NPC identification, and then all three together.

Figure 25:
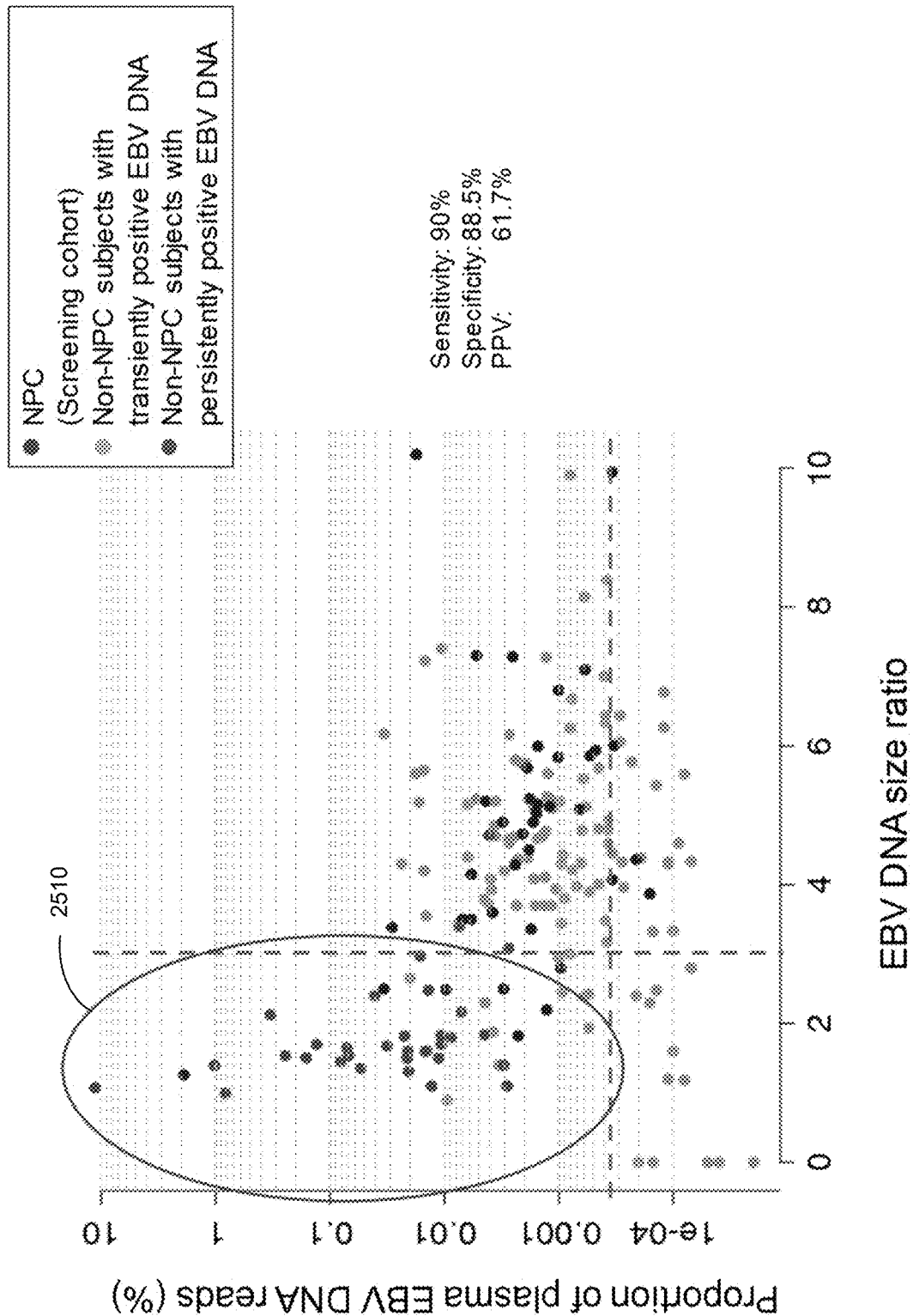
FIG. 25 is a plot of the proportions of the plasma EBV DNA reads and corresponding size ratio values for the NPC patients, non-NPC subjects with transiently positive, and persistently positive plasma EBV DNA according to embodiments of the present disclosure.

FIG. 25 is a plot of the proportions of the plasma EBV DNA reads and corresponding size ratio values for the NPC patients, non-NPC subjects with transiently positive, and persistently positive plasma EBV DNA according to embodiments of the present disclosure. The same cutoff values in EBV DNA size ratios and the proportion of plasma EBV DNA reads defined in FIGS. 23 and 24 are denoted by the grey dotted lines. The red oval highlights the quadrant 2510 that passed the combined analyses.

In this combined analysis, a plasma sample was deemed to be positive if its sequencing data concurrently passed the cutoffs in both the analyses for the proportions and size ratios of plasma EBV DNA. Using the cutoffs defined above, the sensitivity, specificity and positive predictive value for NPC detection were 90%, 88.5% and 61.7%, respectively.

Figure 26:
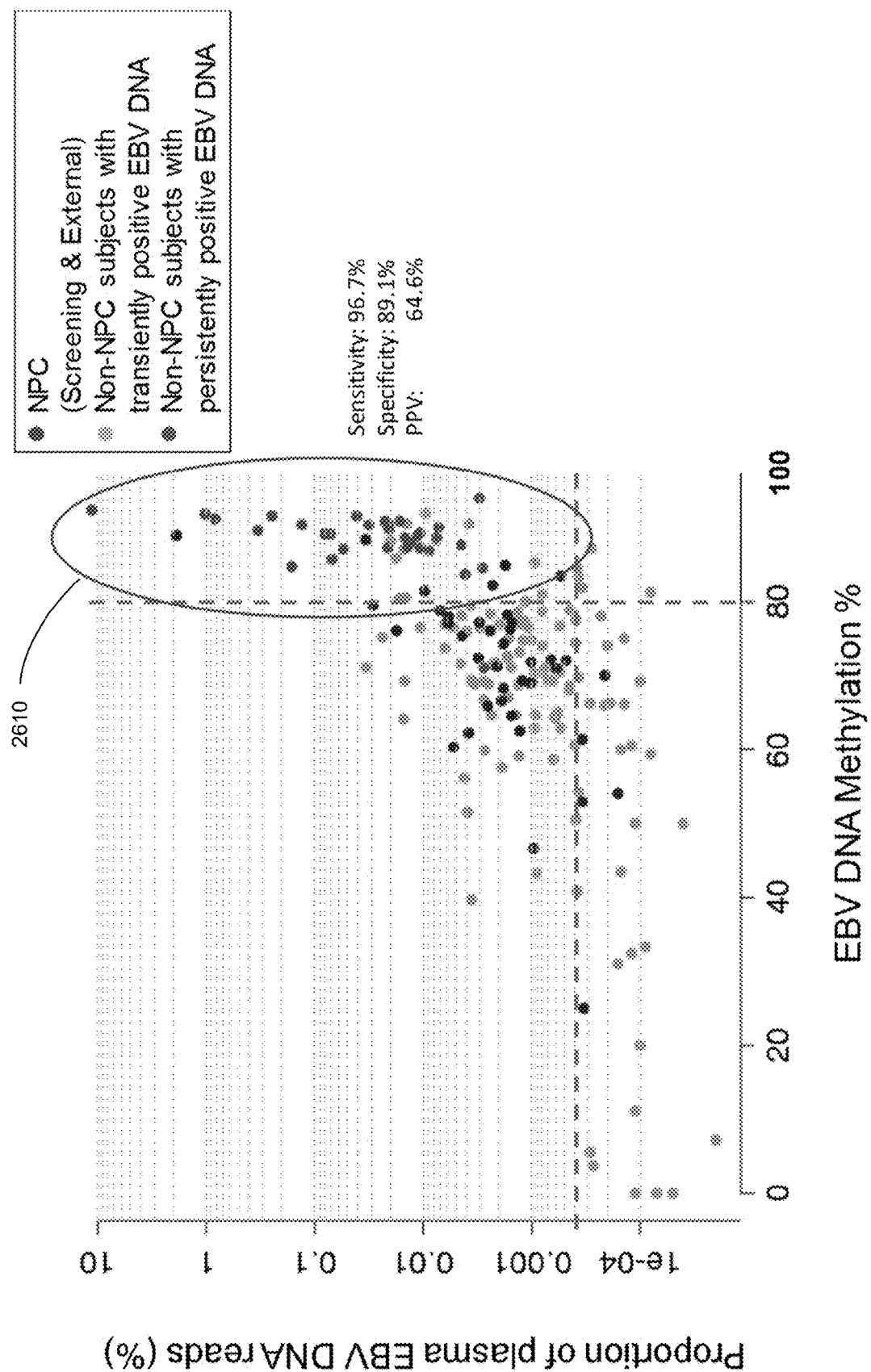
FIG. 26 is a plot of the proportions of the plasma EBV DNA reads and corresponding methylation percentage values for the NPC patients, non-NPC subjects with transiently positive, and persistently positive plasma EBV DNA according to embodiments of the present disclosure.

FIG. 26 is a plot of the proportions of the plasma EBV DNA reads and corresponding methylation percentage values for the NPC patients, non-NPC subjects with transiently positive, and persistently positive plasma EBV DNA according to embodiments of the present disclosure. The same cutoff values in the EBV DNA methylation percentages within the 46 DMRs and the proportion of plasma EBV DNA reads are respectively defined in FIGS. 13 and 24 are denoted by the grey dotted lines. The red oval highlights the quadrant 2610 that passed the combined analyses.

In this combined analysis, a plasma sample was deemed to be positive if its sequencing data concurrently passed the cutoffs in both the analyses for the proportions and methylation percentages of plasma EBV DNA (based on the DMR defined in FIG.). Using the cutoffs defined above, the sensitivity, specificity, and positive predictive value for NPC detection were 96.7%, 89.1% and 64.6%, respectively.

Figure 27B:
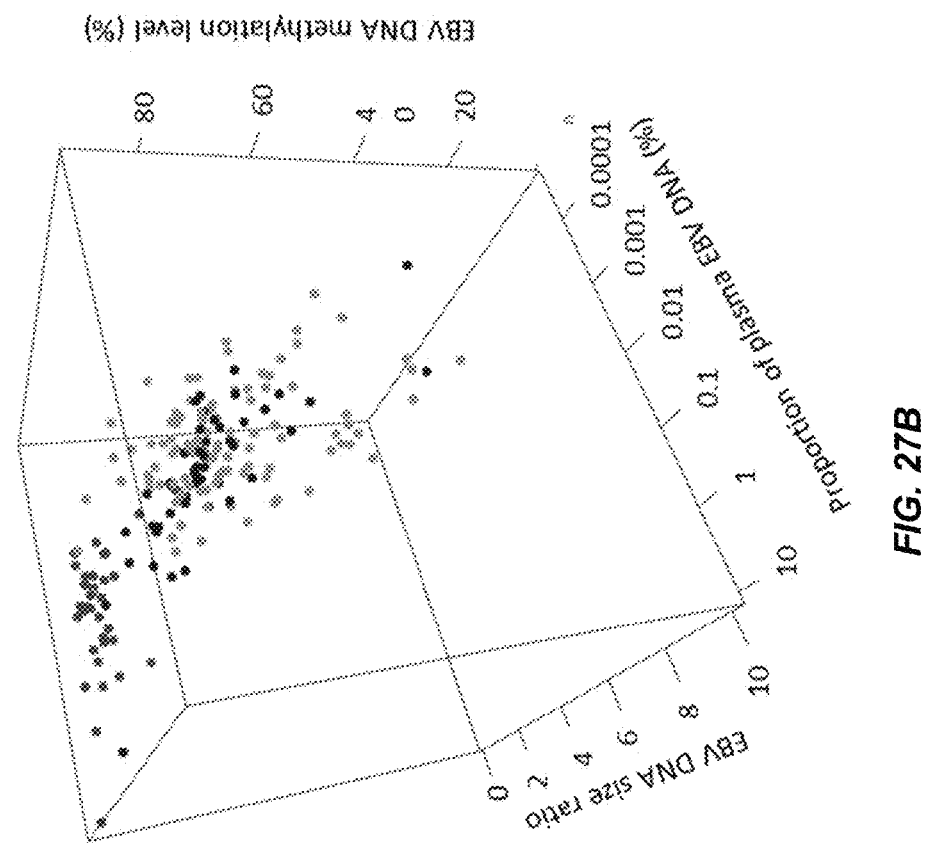
FIGS. 27A and 27B show a 3-dimensional plot of the proportions of the plasma EBV DNA reads and corresponding size ratio and methylation percentage values for the NPC patients, non-NPC subjects with transiently positive, and persistently positive plasma EBV DNA according to embodiments of the present disclosure.
Figure 27A:
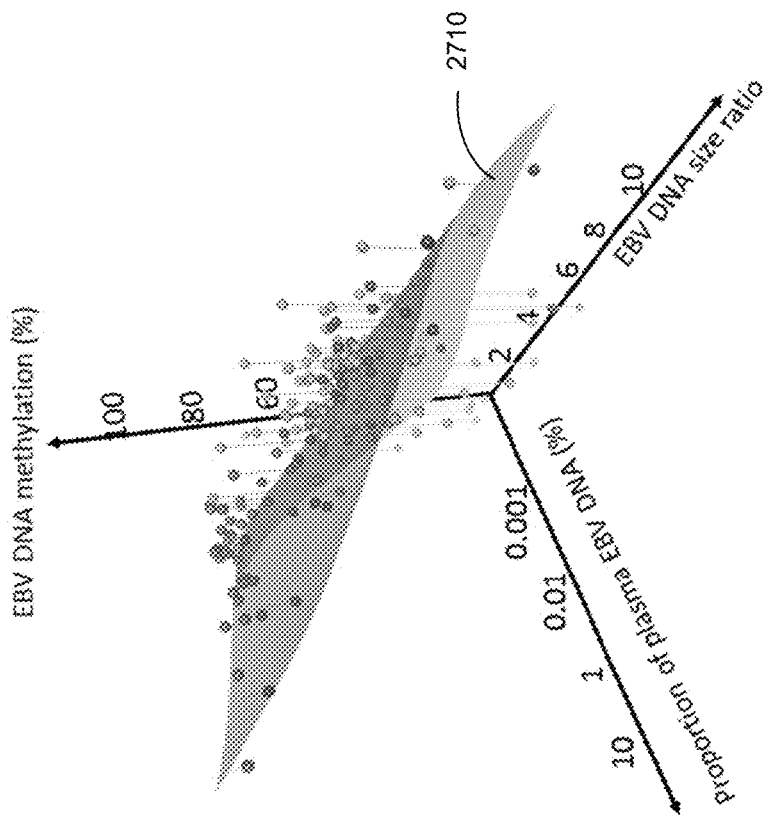

FIGS. 27A and 27B show a 3-dimensional plot of the proportions of the plasma EBV DNA reads and corresponding size ratio and methylation percentage values for the NPC patients, non-NPC subjects with transiently positive, and persistently positive plasma EBV DNA according to embodiments of the present disclosure. We assessed the value of combining all the three parameters, plasma EBV DNA proportions (quantification), size ratios, and methylation percentages for NPC identification. The proportions were determined in a same manner as FIG. 24. The size ratios were determined in a same manner as FIG. 23. And, the methylation levels are determined using the 46 DMRs used for FIG. 13.

In FIG. 27A, the purple surface 2710 denotes a fitted 3-D surface that differentiates the NPC patients from the non-NPC subjects with transiently and persistently positive plasma EBV DNA in the 3-dimensional space. The use of a fitted surface illustrates that the reference values for differentiating among subjects can be more complex than constant values. For example, in FIG. 26, the cutoff for the methylation percentage could vary with the proportion of sequence reads. Such flexibility in determining classification can provide for greater accuracy. The fitting can be selected to optimized various accuracy metrics, e.g., specificity, sensitivity, or some average of both. Such fitting can be performed using support vector machines. FIG. 27B shows the same data as in FIG. 27A, but without surface 2710, and with the axes labeled in a box around the data.

Figure 28A:
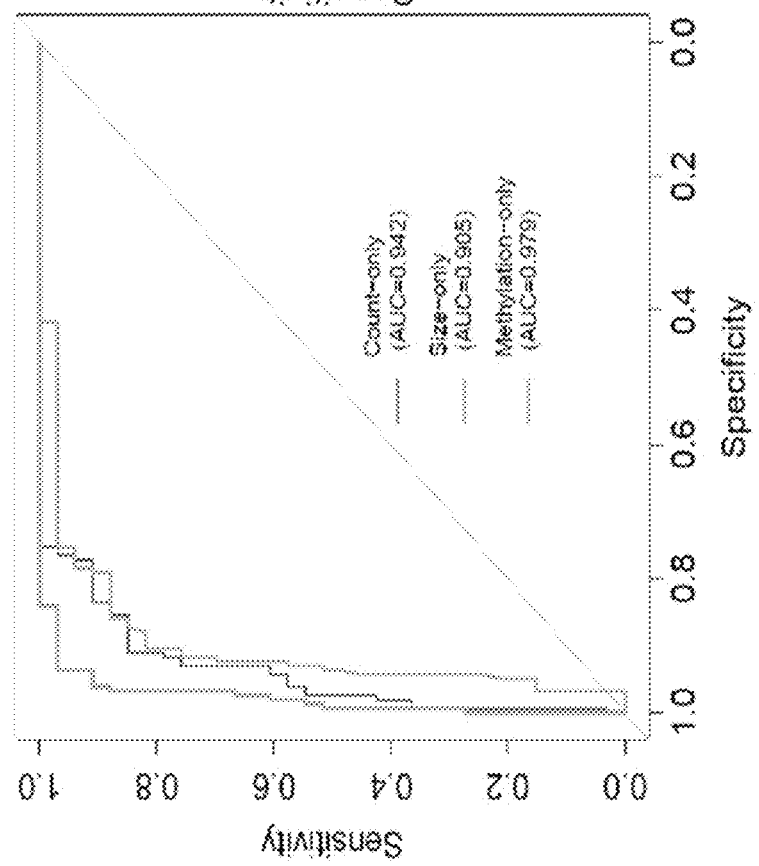
FIGS. 28A and 28B show a receiver operator characteristics (ROC) curve analysis for various combinations of count-based, size-based, and methylation-based analyses according to embodiments of the present disclosure.
Figure 28B:
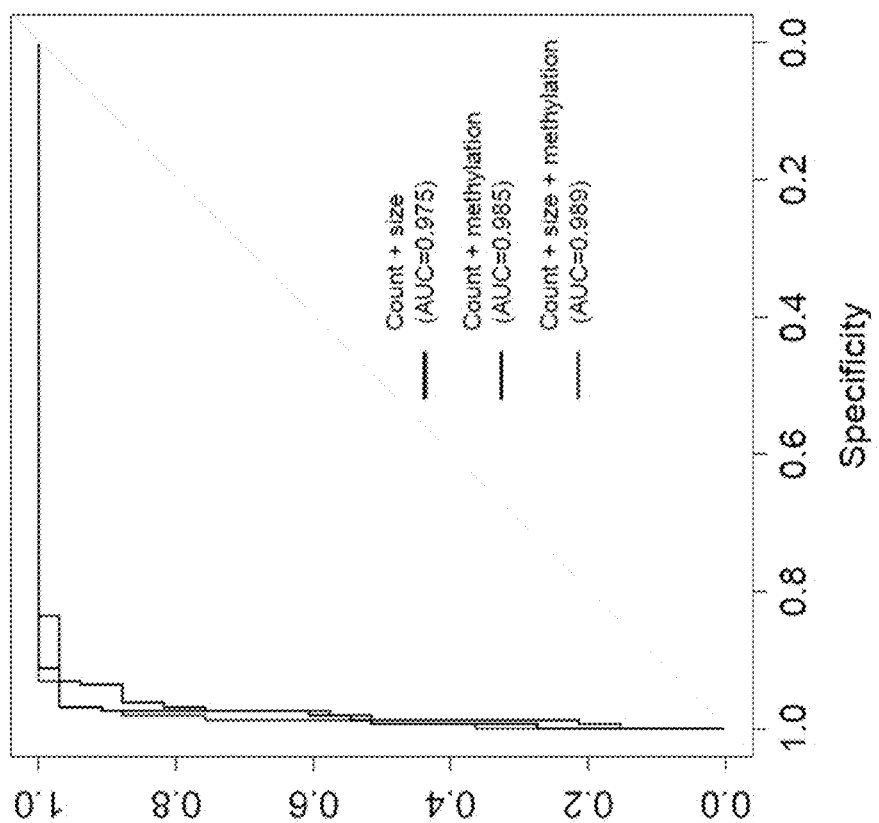

FIGS. 28A and 28B show a receiver operator characteristics (ROC) curve analysis for various combinations of count-based, size-based, and methylation-based analyses according to embodiments of the present disclosure. The accuracy is for the correct classification of NPC subjects and non-NPC subjects. The parameters (i.e., proportions, size ratios, and methylation levels) were determined in a same manner as for FIGS. 27A and 27B. Cutoff value were varied, thereby causing a change in sensitivity and specificity. FIG. 27A shows a comparison of the three techniques used individually. The area under the curve (AUC) values are shown. The AUC values were 0.905, 0.942 and 0.979 respectively for count-only, size-only, and methylation-only. Methylation provides the best results. FIG. 28B shows a comparison of three combined techniques. The AUC value for count and size is 0.97. The AUC value for count and methylation is 0.985. Using all three techniques provides the best accuracy with 0.989.

VI. Other Viral Examples

Other viruses are also associated with cancer. For example, plasma human papillomavirus (HPV) is associated with head and neck squamous cell carcinoma (HNSCC). And, hepatitis B virus (HBV) is associated with hepatocellular carcinoma (HCC). The results below show that embodiments can use methylation level(s) for other cell-free viral DNA to classify levels of a condition in a similar manner that methylation level(s) were used for cell-free EBV DNA.

A. HPV

FIG. 29 shows the clinical stage of the 5 cases of HPV positive-head and neck squamous cell carcinoma (HPV+ve HNSCC). The cases were staged according to the 8$^{th}$ Edition of AJCC Cancer Staging Manual. We have analyzed the methylation profiles of plasma human papillomavirus (HPV) DNA reads from these 5 patients with HPV positive-head and neck squamous cell carcinoma (HPV+ve HNSCC) by target bisulfite sequencing of plasma DNA. All the 5 patients had early stage (stage I or II) diseases. All of them had detectable HPV DNA fragments in their plasma DNA samples.

For each clinical case, plasma DNA was extracted from 4 mL plasma using the QIAamp DSP DNA blood mini kit. For each case, all extracted DNA was used for the preparation of sequencing library using TruSeq DNA PCR-free library preparation kit) (ILLUMINA®). The adapter-ligated DNA products were subjected to two rounds of bisulfite treatment using an EpiTect Bisulfite Kit (Qiagen). Twelve to fifteen cycles of PCR amplification were performed on the bisulfite-converted samples using the KAPA HiFi HotStart Uracil+ReadyMix PCR kit (Roche). The amplification products were then captured with the SeqCap-Epi system (Nimblegen) using the custom-designed probes covering the viral and human genomic regions stated above (FIG. 1).

After the target capture, the captured products were enriched by 14 cycles of PCR to generate DNA libraries. The DNA libraries were sequenced on a NextSeq platform) (ILLUMINA®). For each sequencing run, four to six samples with unique sample barcodes were sequenced using the paired-end mode. For each DNA fragment, 75 nucleotides were sequenced from each of the two ends. After sequencing, the sequence reads were processed in Methyl-Pipe, a methylation data-analysis pipeline (Jiang et al. PLoS One 2014; 9:e100360), and mapped to an artificially combined reference sequence comprising the whole human genome (hg19), the whole EBV genome (AJ507799.2), the whole HBV genome, and the whole HPV genome. Sequenced reads mapping to unique positions (although mismatches may be allowed in other embodiments) in the combined genomic sequence were used for downstream analysis.

Figure 30:
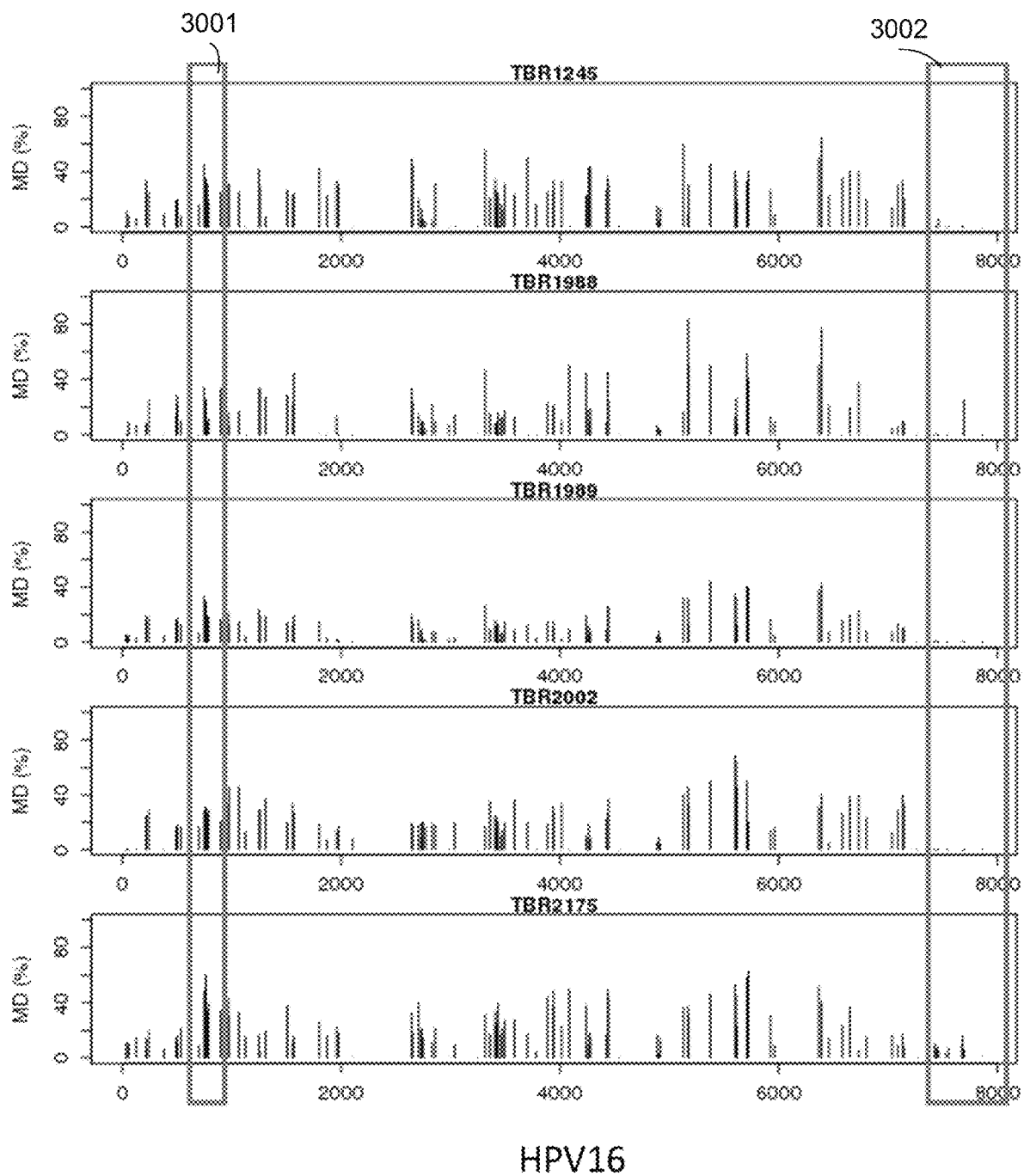
FIG. 30 shows the methylation profiles of plasma HPV DNA in individual patients with HPV positive head and neck squamous cell carcinoma (HPV+ve HNSCC) according to embodiments of the present disclosure.

FIG. 30 shows the methylation profiles of plasma HPV DNA in individual patients with HPV positive head and neck squamous cell carcinoma (HPV+ve HNSCC) according to embodiments of the present disclosure. The methylation profiles of HPV DNA were generated through targeted capture bisulfite sequencing of plasma DNA from these patients. FIG. 30 shows that HPV16 (HPV serotype 16) methylation can be detected in plasma HPV16 DNA molecules of HNSCC patients. The methylation density of all the CpG sites across the HPV genome was determined.

The methylation density MD of specific loci across the viral genome in the plasma can be calculated using the equation: MD=M/(M+U), where M is the count of methylated viral reads and U is the count of unmethylated viral reads at the CpG sites within the genetic locus across the viral genome. On a locus-specific level, these loci could be of any size and of at least 1 CpG site (1 bp). If there is more than one CpG site within a locus, then M and U corresponds to the counts across the sites. These loci could be and could be not associated with any annotated viral genes.

We could observe similar patterns of the methylation profiles of plasma HPV DNA among different patients. Usually there are no HPV in the non-cancer subjects. We defined two genomic regions, namely region 3001 and region 3002. The region-specific methylation density in region 3001 was consistently higher than that in region 3002 for all 5 cases of HPV+ve HNSCC. These similarities in the patterns among subjects with the same condition and differences in the patterns among subjects with different conditions of methylation profiles could be analyzed on a global or locus-specific level. The methylation densities of such pre-defined regions could predict the clinical presentation, for example, for cancer stage, response to treatment, and recurrence risk.

Figure 31:
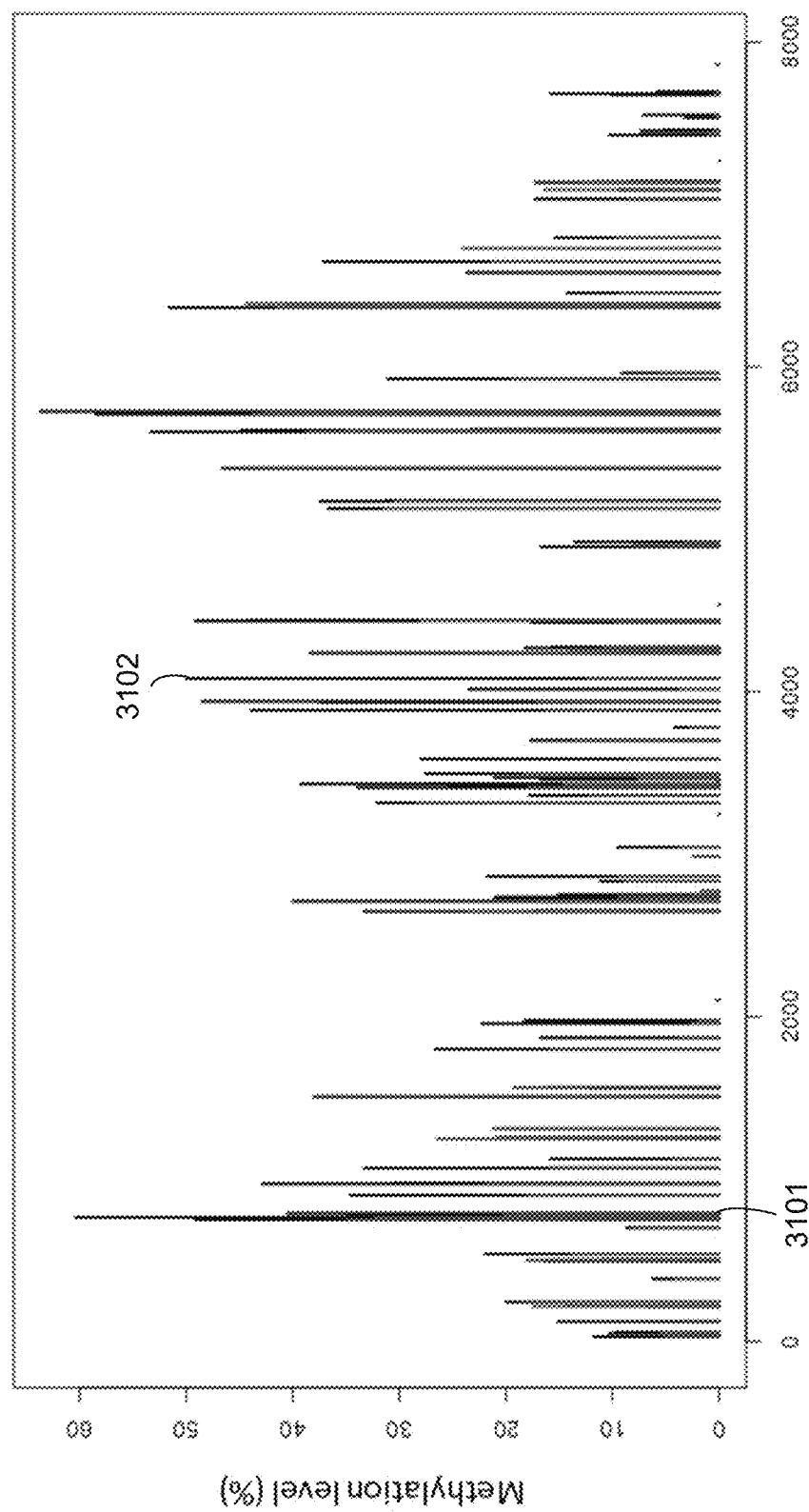
FIG. 31 shows the methylation level of all the CpG sites across the HPV genome in two patients with HPV+ve HNSCC according to embodiments of the present disclosure.

FIG. 31 shows the methylation level of all the CpG sites across the HPV genome in two patients with HPV+ve HNSCC according to embodiments of the present disclosure. A first patient is shown in red and is on the bottom, as depicted at 3101. A second patient is in black, and when larger can be seen, as in 3102. As can be seen, the two patients have appreciable methylation levels at similar loci, and many loci have similar values for the methylation levels. By comparing the methylation level on a global or locus-specific level among cases, embodiments can identify a subject as having HNSCC.

B. HBV

Targeted bisulfite sequencing of plasma DNA was performed for 9 patients with chronic hepatitis B infection and 10 patients with HCC. We also analyzed the methylation profile of plasma HBV reads from these patients with chronic hepatitis B infection and HCC.

Figure 32B:
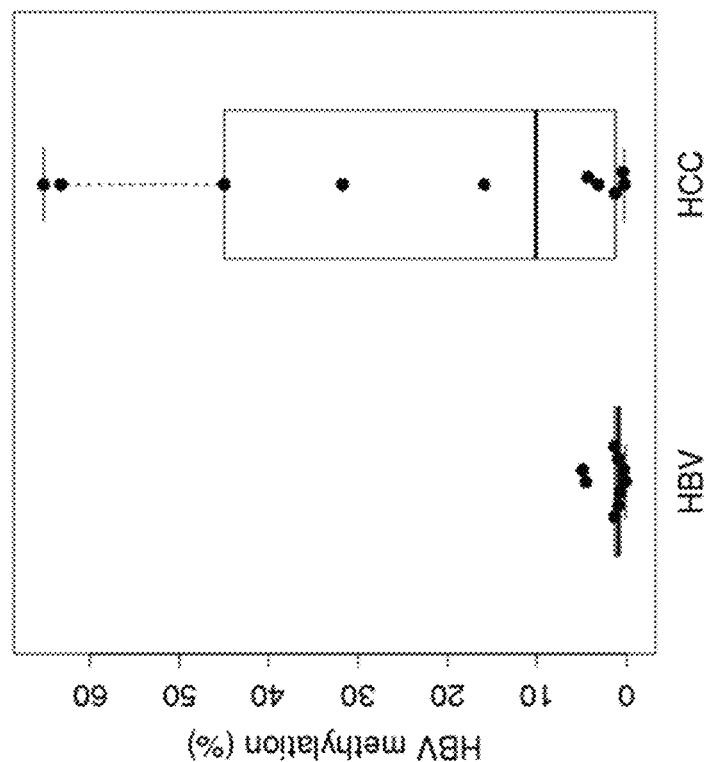
FIGS. 32A and 32B show the proportions of hepatitis B virus (HBV) DNA reads (plasma DNA reads mapped to the HBV genome) and the methylation percentages of all the CpG sites across the HBV genome for 9 patients with chronic hepatitis B infection (HBV) and 10 patients with hepatocellular carcinoma (HCC) according to embodiments of the present disclosure.
Figure 32A:
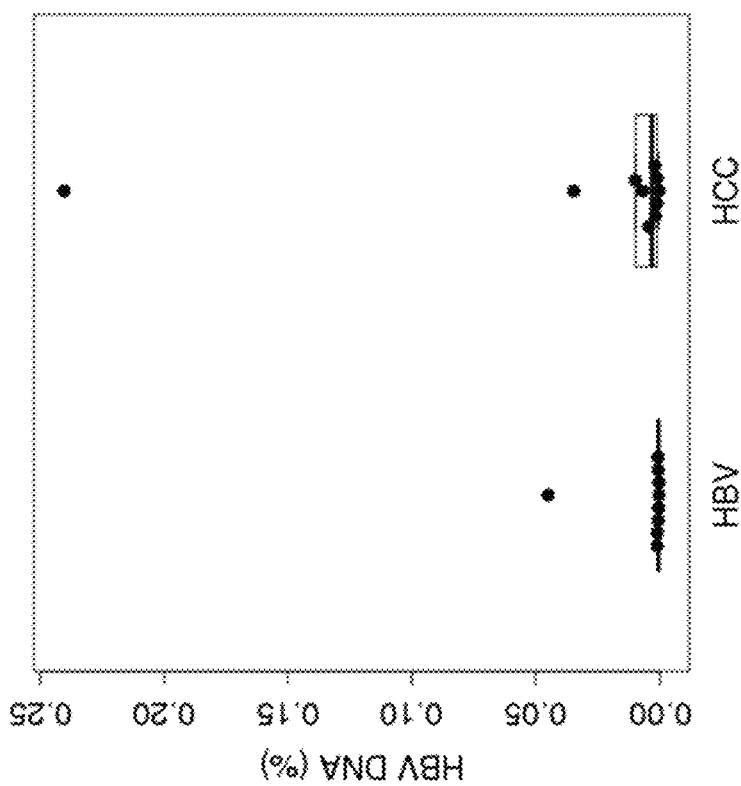

FIGS. 32A and 32B shows the proportions of hepatitis B virus (HBV) DNA reads (plasma DNA reads mapped to the HBV genome) and the methylation percentages of all the CpG sites across the HBV genome for 9 patients with chronic hepatitis B infection (HBV) and 10 patients with hepatocellular carcinoma (HCC) according to embodiments of the present disclosure.

In FIG. 32A, the percentage of DNA fragments that aligned to the HBV genome relative to the human genome was determined. In this particular example, the number of cell-free DNA fragments uniquely aligning to the HBV genome was divided by the number of cell-free DNA fragments that uniquely aligned to a combined reference genome comprising the genomes of human, HBV, HPV and EBV as listed in FIG. 1. A higher average proportion of HBV DNA reads was observed in patients with HCC (mean=0.006%) than patients with chronic HBV infection (mean=0.03%), but a statistical significance was not achieved (p=0.07, Student's t-test). As one can see visually, the means of the HCC subjects and the HBV subjects are similar. Thus, a count-based technique has a relatively low predictive capability.

In FIG. 32B, the HBV methylation percentage was determined as a global methylation level across all the CpG sites in the HBV genome. We observed a significantly higher methylation percentage of plasma HBV DNA for patients with HCC (mean=1.7%) than patients with chronic hepatitis B infection (mean=23%) (p=0.03, Student's t-test). Such a separation indicates an increased ability to discriminate between subjects that have HBV but without HCC, and those subjects that have HCC. Thus, embodiments can classify levels of the HCC condition (e.g., HCC or no HCC). Accordingly, embodiments could predict the risk of HCC based on the genomewide methylation level of plasma HBV DNA in the sample.

Other embodiments can implement other types of methylation levels, e.g., as described herein. For example, the classification could be based on the methylation levels within differentiated methylated regions with pre-defined criteria.

VII. Method Using Methylation of Cell-Free Viral DNA

As described above, embodiments can measure one or more methylation levels in a sample of cell-free DNA, including cell-free viral DNA and cell-free genomic human DNA. The methylation levels can classify a level of a condition by analyzing the methylation level(s) for DNA from a particular virus that is associated with the condition. Count-based and size-based techniques can also be used to supplement the methylation techniques.

As examples, the level of the condition may be whether the condition exists, a severity of a condition, a stage of the condition, an outlook for the condition, the condition's response to treatment, or another measure of severity or progression of the condition. As examples for cancer, the level of cancer may be whether cancer exists, a stage of cancer (e.g., early stage and late stage), a size of tumor, the cancer's response to treatment, or another measure of a severity or progression of cancer.

For EBV, example conditions can include infectious mononucleosis (IM), nasopharyngeal carcinoma (NPC), natural killer (NK)-T cell lymphoma, and subjects without these conditions, but who may show appreciable numbers of cell-free EBV DNA fragments in the sample. For HPV, example conditions can include head and neck squamous cell carcinoma (HNSCC) and subject that have an appreciable amount of cell-free HPV DNA fragments, but do not have HNSCC. For HBV, example conditions can include hepatocellular carcinoma (HCC) and subjects that have an appreciable amount of cell-free HBV DNA fragments, but do not have HCC.

A. Using Methylation Levels to Classify Condition

Figure 33:
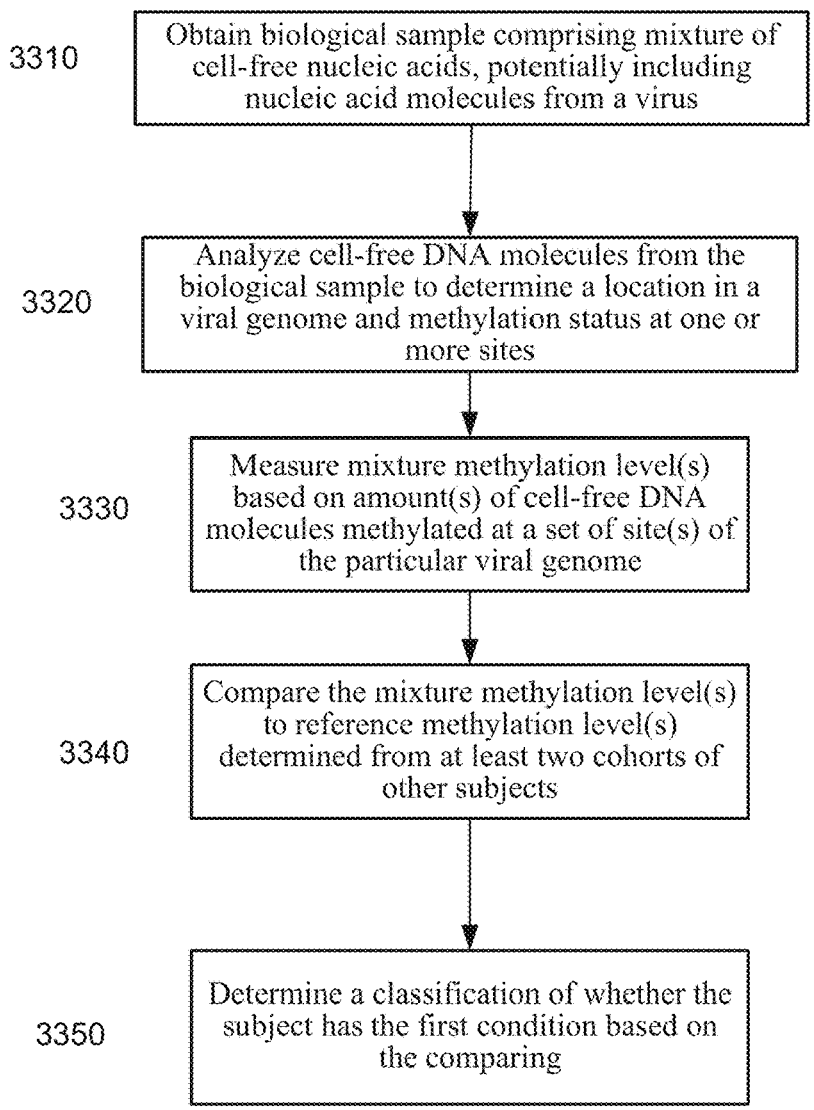
FIG. 33 is a flowchart illustrating a method of analyzing a biological sample of a subject that is an animal to determine a classification of a first condition according to embodiments of the present disclosure.

FIG. 33 is a flowchart illustrating a method 3300 of analyzing a biological sample of a subject that is an animal to determine a classification of a first condition according to embodiments of the present disclosure. The sample can include a mixture of DNA molecules from the subject and potentially DNA molecules from a virus. Method 3300 can include clinical, laboratory, and in silico (computer) steps. Method 3300 can be performed as part of a screening of subjects, e.g., to screen for cancer. Thus, the subject may be asymptomatic for the condition.

At block 3310, the biological sample is obtained from the subject. As examples, the biological sample can be blood, plasma, serum, urine, saliva, sweat, tears, and sputum, as well as other examples provided herein. The biological sample can include a mixture of cell-free DNA molecules from a genome of the subject and from one or more other genomes. For example, the one or more other genomes can include viral genomes, such as, EBV, HPV, and/or HBV genomes. In some embodiments (e.g., for blood), the biological sample can be purified for the mixture of cell-free DNA molecules, e.g., centrifuging blood to obtain plasma.

At block 3320, a plurality of cell-free DNA molecules are analyzed from the biological sample. The analysis of a cell-free DNA molecule can include identifying a location of the cell-free DNA molecule in a particular viral genome and determining whether the cell-free DNA molecule is methylated at one or more sites of the particular viral genome. Various numbers of cell-free DNA molecules can be analyzed (human and virus), e.g., at least 1,000, with various numbers being identified as from the particular viral genome (e.g., 10, 20, 30, 50, 100, 200, 500, or a 1,000 or more).

The methylation status of sites of the sequence read can be obtained as described herein. For example, the DNA molecules can be analyzed using sequence reads of the DNA molecules, where the sequencing is methylation-aware. Other methylation-aware assays can also be used. The sequence reads can each include a methylation status of cell-free DNA molecules from the biological sample. The methylation status can include whether a particular cytosine residue is 5-methylcytosine or 5-hydroxymethylcytosine. The sequence reads can be obtained in various ways, each as various sequencing techniques, PCR techniques (e.g., real-time or digital), arrays, and other suitable techniques for identifying sequences of fragments. Real-time PCR is an example of analyzing a group of DNA collectively, e.g., as an intensity signal proportional to the number of DNA methylated at a site. A sequence read can cover more than one site depending on the proximity of the two sites to each other and the length of the sequence read.

The analysis can be performed by receiving sequence reads from a methylation-aware sequencing, and thus the analysis can be performed just on data previously obtained from the DNA. In other embodiments, the analysis can include the actual sequencing or other active steps for performing the measurements of the properties of the DNA molecules. The sequencing may be performed in a variety of ways, e.g., using massively parallel sequencing or next-generation sequencing, using single molecule sequencing, and/or using double- or single-stranded DNA sequencing library preparation protocols, and other techniques described herein. As part of the sequencing, it is possible that some of the sequence reads may correspond to cellular nucleic acids.

The sequencing may be targeted sequencing, e.g., as described herein. For example, biological sample can be enriched for nucleic acid molecules from the virus. The enriching of the biological sample for nucleic acid molecules from the virus can include using capture probes that bind to a portion of, or an entire genome of, the virus. Other embodiments can use primers specific to a particular locus of the virus. The biological sample can be enriched for nucleic acid molecules from a portion of a human genome, e.g., regions of autosomes. FIG. 1 provides examples of such capture probes. In other embodiments, the sequencing can include random sequencing.

After sequencing by a sequencing device, the sequence reads may be received by a computer system, which may be communicably coupled to a sequencing device that performed the sequencing, e.g., via wired or wireless communications or via a detachable memory device. In some embodiments, one or more sequence reads that include both ends of the nucleic acid fragment can be received. The location of a DNA molecule can be determined by mapping (aligning) the one or more sequence reads of the DNA molecule to respective parts of the human genome, e.g., to specific regions, such as differentially methylation regions (DMRs). In one implementation, if a read does not map to a region of interest, then the read can be ignored. In other embodiments, a particular probe (e.g., following PCR or other amplification) can indicate a location, such as via a particular fluorescent color. The identification can be that the cell-free DNA molecule corresponds to one of the set of one or more sites, i.e., the particular site may not be known, as the amount of DNA methylated at one or more sites is all that is needed.

At block 3330, one or more mixture methylation levels are measured based on one or more amounts of the plurality of cell-free DNA molecules methylated at a set of one or more sites of the particular viral genome. A mixture methylation level may be a methylation density or percentage (e.g., as described herein) for the cell-free DNA molecules of the set of site(s) or a subset of the site(s). For example, the methylation level can correspond to a methylation density that is determined based on the number of DNA molecules corresponding to the set of sites and the number methylated. The number may be determined based on alignment of sequence reads to the viral genome, in combination with the methylation status for a given sequence read at one or more sites.

A respective number of DNA molecules that are methylated at the site can be determined for each of the set of sites. In one embodiment, the sites are CpG sites, and may be only certain CpG sites, as selected using one or more criteria mentioned herein. The number of DNA molecules that are methylated is equivalent to determining the number that are unmethylated once normalization is performed using a total number of DNA molecules analyzed at a particular site, e.g., a total number of sequence reads. For example, an increase in the CpG methylation density of a region is equivalent to a decrease in the density of unmethylated CpGs of the same region.

When the set of one or more sites includes at least two sites, one mixture methylation level can be determined across the at least two sites. For example, the methylation level can be computed as a total methylation density for all of the cell-free DNA molecules of the first set. In another example, separate methylation densities can be computed for each site or region(s) of one or more sites, thereby providing N (e.g., integer of 2 or more) mixture methylation levels as multidimensional point, e.g., as described in sections IV.B-IV.E. The separate methylation densities can be combined to obtain the mixture methylation level, e.g., an average of the separate methylation densities.

In other embodiments, the separate methylation levels may be kept for later analysis, e.g., using clustering and other techniques described herein. For example, the multi-dimensional point (N mixture methylation levels) can be compared to N reference methylation levels to obtain N differences, which can be used to determine whether the subject belongs to one of the at least two cohorts. FIGS. 18-20 provide such examples for hierarchical clustering analysis. The regions may be predetermined, e.g., as described above for predetermined regions having a size between 50 bases and 1,000 bases, with the sizes being the same or varying among regions.

If more than one mixture methylation level is determined, the different levels can correspond to different subset of the set of sites. For example, methylation levels can be determined for different regions, each of which may include one or more sites. The regions can span the entire viral genome or correspond to only parts, e.g., as may be done when particular regions are selected. Such regions may be selected for being differentially methylated according to one or more criteria, e.g., as described herein. Such criteria can correspond to methylation levels in a cohort of subjects having a same condition being within a specific range, and potentially having a difference within a threshold from other subjects of the cohort. Thus, the criteria for the regions or for each of the sites may include (1) a difference in methylation level among multiple subjects of a same cohort and/or (2) a difference in methylation level between a subject of one cohort and a subject of another cohort.

At block 3340, the one or more mixture methylation levels are compared to one or more reference methylation levels determined from at least two cohorts of other subjects. The at least two cohorts can have different classifications associated with the particular viral genome, where the different classifications include a first condition. Examples of such conditions are provided above, e.g., NPC, IM, lymphoma, and non-NPC states related to transient or persistently positive for the number of EBV DNA molecules. Examples of cohorts and reference methylation levels are provided in FIGS. 8, 11, 13, 15, and 18-20.

The comparison can take various forms. For example, a separation value can be determines, such as a ratio or a difference between a mixture methylation level and a reference methylation level. Various separation values can be defined, include definitions that includes ratios and differences, and functions of both. The comparison can further include a comparison of the separation value to a cutoff value to determine a statistically significant difference. For example, the reference methylation level can be an average for a cohort, and a difference between the mixture methylation level of a sample and the average for the cohort can be compared to a cutoff value, which may be determined based on a standard deviation of the measured methylation levels for the reference samples used in the cohort.

In some embodiments involving multiple methylation levels and multiple reference levels, the multiple methylation levels can correspond to a sample multidimensional point (e.g., N levels forming a vector) with the multiple reference levels corresponding to surface (e.g., a hyperplane) of N−1 dimensions, where the surface may be a closed surface, e.g., like a sphere in which the data points correspond to a same condition. As another example, the comparison of multiple methylation levels to reference levels can be implemented by determining a distance between the sample multidimensional point to a representative (reference) multidimensional point of a reference subject. The reference multidimensional point can correspond to a single reference subject, e.g., patient AL038. As another example, the representative (reference) multidimensional point can be a centroid of a cluster of reference multidimensional points from subjects with the same condition.

As another example, the comparing of mixture methylation level(s) to reference methylation level(s) can include inputting the one or more mixture methylation levels into a machine learning model that was trained using the one or more reference methylation levels determined from the at least two cohorts of other subjects. For example, the reference levels can be the methylation levels measured for the other subjects, and a clustering model can be trained using those reference levels. For instance, a centroid can be selected for the cluster of subjects corresponding to a particular cohort.

At block 3350, a first classification of whether the subject has the first condition is determined based on the comparing. The first classification can take various forms, e.g., a binary result or a probability value. In some embodiments, the first classification can provide a level of the first condition, e.g., a size of a tumor, a severity, or a stage of cancer.

The different classifications of the at least two cohorts can also include a second condition, where the comparison to the one or more reference levels can determine a second classification of whether the subject has the second condition. For example, a single reference level can discriminate between IM and lymphoma, or between NPC and persistently positive subjects.

The one or more mixture methylation levels can be compared to a plurality of reference methylation levels. As an example of using one methylation level but multiple reference methylation levels, different reference levels can discriminate between different conditions. For example, first reference methylation level can determine the first classification of whether the subject has the first condition (e.g., discriminate between IM and not having IM), and second reference methylation level can determine the second classification of whether the subject has the second condition (e.g., discriminate between NPC and not having NPC), e.g., as depicted in FIGS. 8, 11, and 15. Thus, embodiments can use a different reference level to determine a second classification of whether the subject has a second condition based on the comparing.

The method may further include treating the subject for the condition responsive to the classification being that the subject has the condition, thereby improving the condition (e.g., to remove the condition or reduce severity). If the condition is cancer, the treatment may include surgery, radiation therapy, chemotherapy, immunotherapy, targeted therapy, hormone therapy, stem cell transplant, or precision medicine. Based on the determined level of condition, a treatment plan can be developed to decrease the risk of harm to the subject. Methods may further include treating the subject according to the treatment plan.

Biological samples can be obtained at various time points and analyzed independently at those time points, or in conjunction with the measurements and classifications at the other time points. Examples of such time points include before and after treatment of cancer (e.g. targeted therapy, immunotherapy, chemotherapy, surgery), different time points following the diagnosis of cancer, before and after progression of cancer, before and after development of metastasis, before and after increased severity of disease, or before and after development of complications.

B. Using Methylation Levels in Combination with Size/Count

As described in section V, count-based and/or size-based techniques can be used in combination with methylation techniques. Such techniques can be implemented independently, e.g., each providing a separate classification. Each of such independent classifications can be required to provide a same result in order to provide a final classification of that result. In other embodiments, the reference values for the different techniques can depend on the metrics from another technique, e.g., the size reference value can depend on a methylation level measured for the given sample, as was described above for FIG. 27. In some implementations, each metric (e.g., a methylation level) can be a different element in a vector, thereby creating a multidimensional data point out of the metrics for a given sample. Each of the metrics can be determined from the same sample or separate samples, e.g., which may be obtained from the subject at around the same time.

In some embodiments, the size-based technique can be implemented as follows to analyze a biological sample of the subject. The sample can be the same or different sample as the one used for the methylation analysis. The biological sample can include a mixture of cell-free DNA molecules from a genome of the subject and from one or more other genomes (e.g., a viral genome). For each of a plurality of cell-free DNA molecules in the biological sample, a size and a location can be determined, e.g., as described herein. For instance, both ends of the DNA molecules can be sequenced (e.g., to provide one sequence read for the entire DNA molecule or a pair of sequence reads for the two ends) and the sequence read(s) aligned to a reference genome to determine size. Thus, embodiments can measure a size of the DNA molecule and identify a location of the DNA molecule in the particular viral genome. These cell-free DNA molecules can be the same as were used for the methylation analysis, e.g., where methylation-aware sequencing is used. The sizes of the plurality of DNA molecules can form a size distribution.

A statistical value (e.g., a size ratio) of the size distribution can be determined. The statistical value can be compared to a reference size value determined from at least two cohorts of other subjects, which may be the same two cohorts used for the methylation analysis. The at least two cohorts can have different classifications associated with the particular viral genome, including a first condition. A size-based classification of whether the subject has the first condition can be determined based on the comparing. The size-based classification and the methylation-based classification can be used together to provide a final classification. Example reference size values are provided in FIGS. 22, 23, 25, and 27.

In some embodiments, the count-based technique can be implemented as follows to analyze a biological sample of the subject. The sample can be the same or different as the one used for the methylation analysis. The biological sample can include a mixture of cell-free DNA molecules from a genome of the subject and from one or more other genomes (e.g., a viral genome).

An amount of cell-free DNA molecules derived from the particular viral genome in a sample can be determined. In some embodiments, for each of a plurality of cell-free DNA molecules in the biological sample, it is determined whether the molecule is derived from the particular viral genome, e.g., using sequencing or probes, potentially along with amplifications, such as PCR. For instance, a location can be determined, e.g., whether from a human genome or from a particular viral genome. The location can be determined using a plurality of sequence reads obtained from a sequencing of the mixture of cell-free DNA. An amount of the plurality of sequence reads aligning to the particular viral genome can be determined. For example, a proportion of sequence reads aligned to the viral genome relative to a total number of sequence reads can be determined. The total number of sequence reads can be a sum of the sequence reads that aligned to a reference genome corresponding to the virus and the sequence reads that aligned to a human genome. Other ratios described herein can also be used, e.g., amount of reads from the particular viral genome divided by the amount of human reads.

The amount of sequence reads aligning to the reference genome can be compared to a reference value determined from at least two cohorts of other subjects, which may be the same two cohorts used for the methylation and/or size analysis. The at least two cohorts can have different classifications associated with the particular viral genome, including a first condition. A count-based classification of whether the subject has the first condition can be determined based on the comparing. The count-based classification and the methylation-based classification can be used together to provide a final classification. Example reference count values are provided in FIGS. 24-27 and 32A.

VIII. Example Systems

Figure 34:
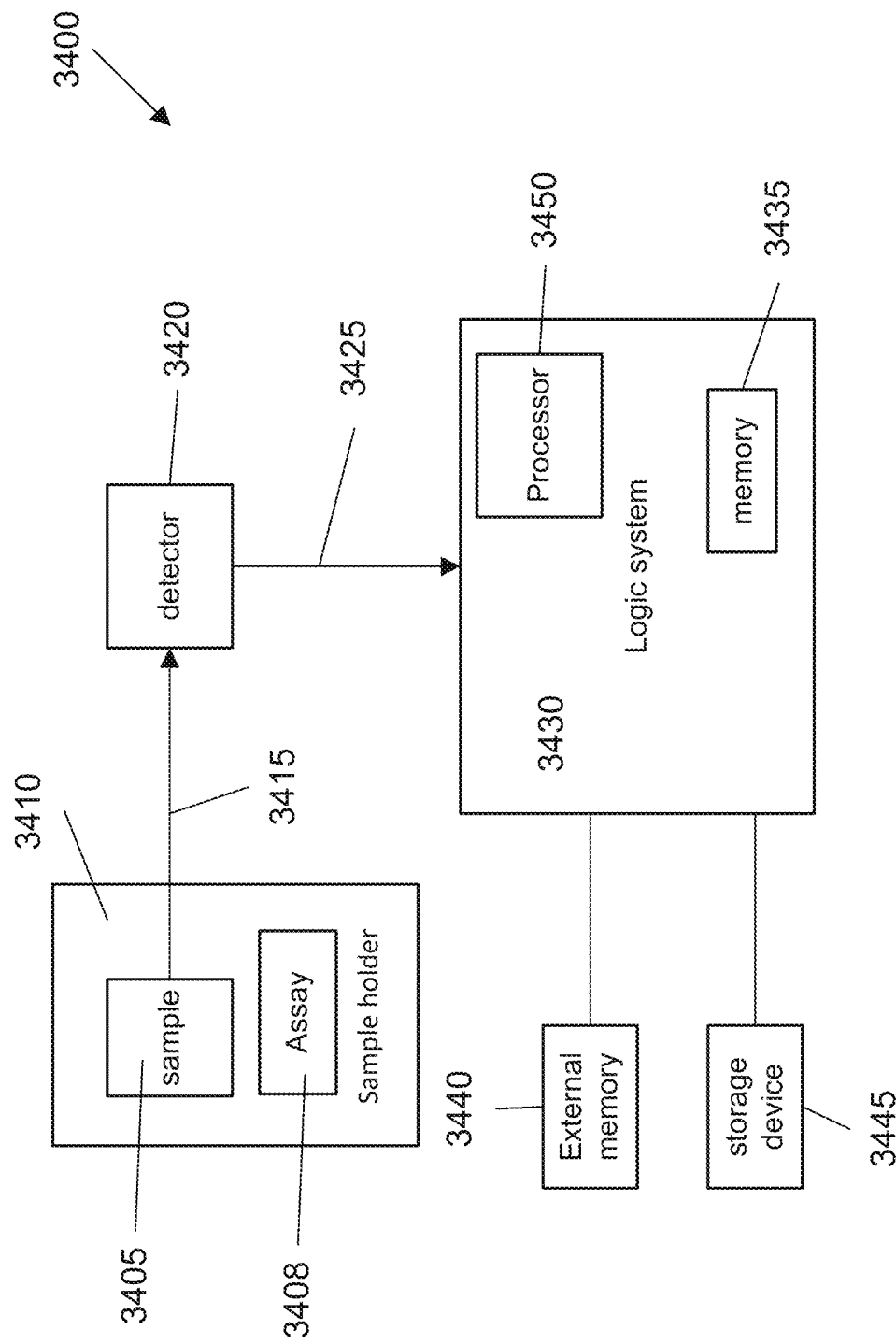
FIG. 34 illustrates a system according to an embodiment of the present invention.

FIG. 34 illustrates a system 3400 according to an embodiment of the present invention. The system as shown includes a sample 3405, such as cell-free DNA molecules within a sample holder 3410, where sample 3405 can be contacted with an assay 3408 to provide a signal of a physical characteristic 3415. An example of a sample holder can be a flow cell that includes probes and/or primers of an assay or a tube through which a droplet moves (with the droplet including the assay). Physical characteristic 3415, such as a fluorescence intensity value, from the sample is detected by detector 3420. Detector 3420 can take a measurement at intervals (e.g., periodic intervals) to obtain data points that make up a data signal. In one embodiment, an analog to digital converter converts an analog signal from the detector into digital form at a plurality of times. Sample holder 3410 and detector 3420 can form a assay device, e.g., a sequencing device that performs sequencing according to embodiments described herein. A data signal 3425 is sent from detector 3420 to logic system 3430. Data signal 3425 may be stored in a local memory 3435, an external memory 3440, or a storage device 3445.

Logic system 3430 may be, or may include, a computer system, ASIC, microprocessor, etc. It may also include or be coupled with a display (e.g., monitor, LED display, etc.) and a user input device (e.g., mouse, keyboard, buttons, etc.). Logic system 3430 and the other components may be part of a stand-alone or network connected computer system, or they may be directly attached to or incorporated in a thermal cycler device. Logic system 3430 may also include optimization software that executes in a processor 3450. Logic system 3430 may include a computer readable medium storing instructions for controlling system 3400 to perform any of the methods described herein.

Figure 35:
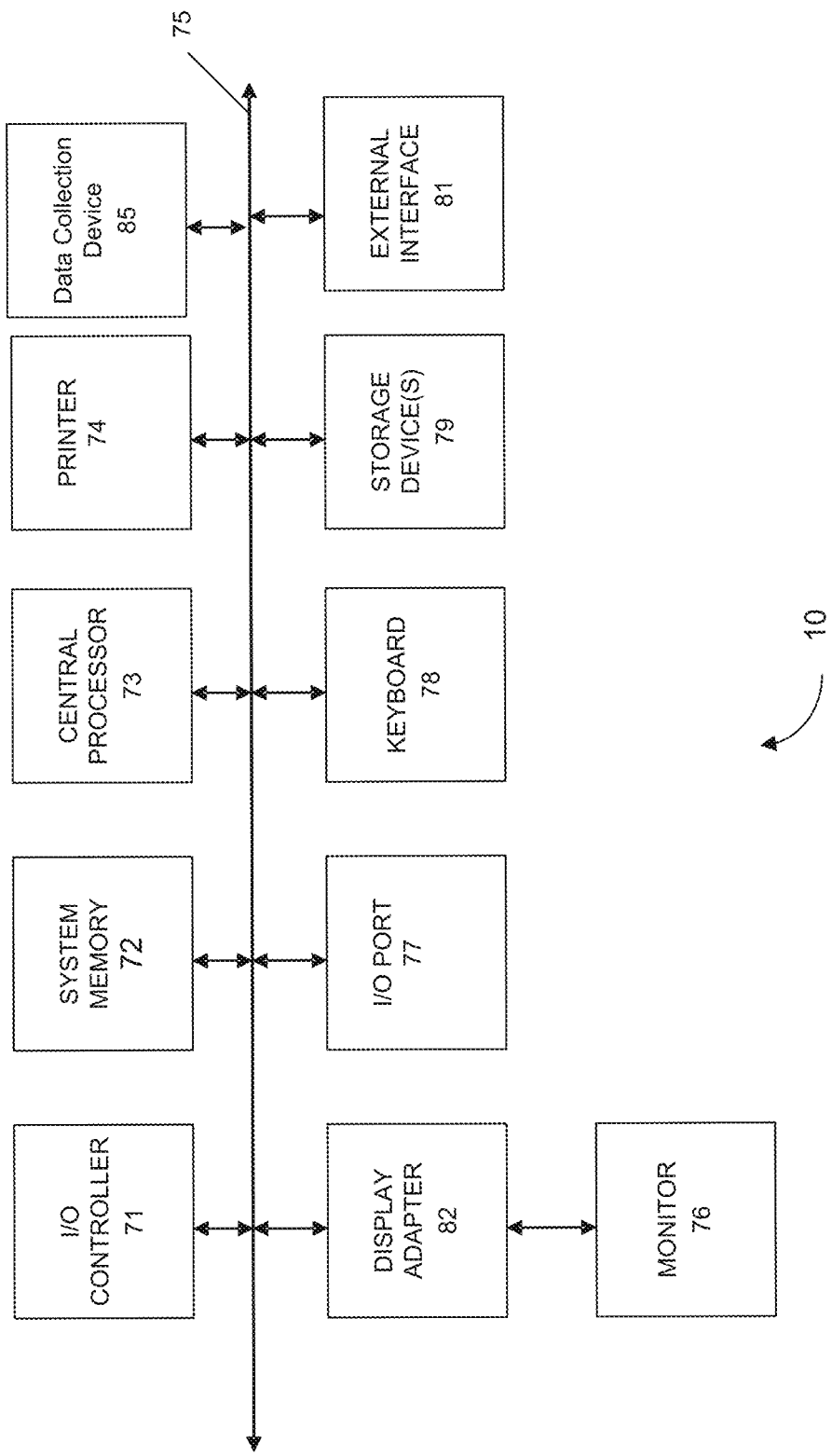
FIG. 35 shows a block diagram of an example computer system usable with system and methods according to embodiments of the present invention.

Any of the computer systems mentioned herein may utilize any suitable number of subsystems. Examples of such subsystems are shown in FIG. 35 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 35 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

All patents, patent applications, publications, and descriptions mentioned herein are incorporated by reference in their entirety for all purposes. None is admitted to be prior art.

What is claimed is:

1. A system for analyzing a biological sample of a subject that is a human, the biological sample including a mixture of cell-free DNA molecules from a genome of the subject and from one or more other genomes, the system comprising:

a detector configured to measure physical characteristics of a plurality of cell-free DNA molecules in the biological sample and provide data signals corresponding to the physical characteristics, the plurality of cell-free DNA molecules being 1,000 or more; and a logic system comprising one or more processors, memory storing a plurality of instructions, and an interface configured to receive the data signals, wherein the instructions, when executed, perform a method comprising:

analyzing the plurality of cell-free DNA molecules from the biological sample, wherein analyzing a group of the plurality of cell-free DNA molecules includes:

identifying locations of the cell-free DNA molecules in a particular viral genome of a cancer-causing virus; and determining whether the cell-free DNA molecules are methylated at one or more sites of the particular viral genome;

measuring a mixture methylation level based on amounts of the plurality of cell-free DNA molecules methylated at a set of sites of the particular viral genome based on the locations;

comparing the mixture methylation level to one or more reference methylation levels determined from at least two cohorts of other subjects, wherein the at least two cohorts have different classifications associated with the particular viral genome, the different classifications including a first condition that is a cancer; and determining a first classification of whether the subject has the first condition based on the comparing, wherein the first condition is nasopharyngeal carcinoma (NPC), hepatocellular carcinoma (HCC), cervical cancer (CC), or head and neck squamous cell carcinoma (HNSCC).

2. The system of claim 1, wherein the different classifications of the at least two cohorts further includes a second condition, wherein the method further comprises:

determining a second classification of whether the subject has the second condition based on the comparing.

3. The system of claim 2, wherein the one or more reference methylation levels are a plurality of reference methylation levels, wherein the mixture methylation level is compared to the plurality of reference methylation levels that include a first reference methylation level and a second reference methylation level, whether the first reference methylation level is used to determine the first classification of whether the subject has the first condition, and wherein the second reference methylation level is used to determine the second classification of whether the subject has the second condition.

4. The system of claim 3, wherein the particular viral genome is of Epstein-Barr virus, wherein the first condition is nasopharyngeal cancer, and wherein the second condition is infectious mononucleosis.

5. The system of claim 1, wherein the first classification is that the subject does not have the first condition.

6. The system of claim 1, wherein determining the first classification includes determining a level of the first condition.

7. The system of claim 1, wherein the particular viral genome is of Epstein-Barr virus, and wherein the first condition is nasopharyngeal cancer.

8. The system of claim 1, wherein measuring the mixture methylation level comprises measuring N mixture methylation levels, N being an integer greater than one, wherein the mixture methylation level is one of the N mixture methylation levels, and wherein the comparing the mixture methylation level to the one or more reference methylation levels comprises comparing the N mixture methylation levels to N reference methylation levels by:
measuring differences between the N mixture methylation levels and N reference methylation levels; and
determining whether the subject belongs to one of the at least two cohorts using the differences.

9. The system of claim 8, wherein determining whether the subject belongs to one of the at least two cohorts using the differences includes performing a hierarchical clustering analysis.

10. The system of claim 8, wherein each of the N mixture methylation levels is measured for one of a plurality of predetermined regions.

11. The system of claim 10, wherein the plurality of predetermined regions are of a same size and span the particular viral genome, and wherein the same size is between 50 bases and 1,000 bases.

12. The system of claim 10, wherein each of the plurality of predetermined regions satisfies one or more criteria including (1) a difference in a methylation level among multiple subjects of a same cohort and/or (2) a difference in the methylation level between a subject of one cohort and a subject of another cohort.

13. The system of claim 1, wherein the set of sites reside in a plurality of regions that each satisfies one or more criteria including (1) a difference in a methylation level among multiple subjects of a same cohort and/or (2) a difference in the methylation level between a subject of one cohort and a subject of another cohort.

14. The system of claim 1, wherein the set of sites satisfies one or more criteria including (1) a difference in a methylation level among multiple subjects of a same cohort and/or (2) a difference in the methylation level between a subject of one cohort and a subject of another cohort.

15. The system of claim 1, wherein comparing the mixture methylation level to the one or more reference methylation levels determined from the at least two cohorts of other subjects comprises:
inputting the mixture methylation level into a machine learning model that was trained using the one or more reference methylation levels determined from the at least two cohorts of other subjects.

16. The system of claim 1, wherein the method further comprises:
for each site of the set of sites:
determining a respective number of DNA molecules that are methylated at the site, thereby determining the amounts of the plurality of cell-free DNA molecules methylated at the set of sites of the particular viral genome.

17. The system of claim 16, wherein the system is configured to perform methylation-aware sequencing of the plurality of cell-free DNA molecules to obtain sequence reads corresponding to the data signals; and wherein the method further comprises:
aligning the sequence reads to the particular viral genome to determine the respective number of DNA molecules that are methylated at each site of the set of sites.

18. The system of claim 1, wherein the system is configured to perform a methylation-aware assay of the plurality of cell-free DNA molecules as part of determining the locations of the plurality of cell-free DNA molecules and whether the plurality of cell-free DNA molecules are methylated at the set of sites.

19. The system of claim 1, wherein identifying a location of a cell-free DNA molecule includes determining that the location corresponds to one of the set of sites.

20. The system of claim 1, wherein the plurality of cell-free DNA molecules are analyzed collectively to determine the amounts of the plurality of cell-free DNA molecules methylated at the set of sites of the particular viral genome.

21. The system of claim 1, wherein the plurality of cell-free DNA molecules includes at least 10 cell-free DNA molecules located in the particular viral genome.

22. The system of claim 1, wherein the particular viral genome corresponds to Epstein-Barr virus, human papillomavirus, or hepatitis B virus.

23. The system of claim 1, wherein the method further comprises:
for each of the plurality of cell-free DNA molecules in a sample:
measuring a size of the cell-free DNA molecule; and
identifying a location of the cell-free DNA molecule in the particular viral genome, the sizes of the plurality of cell-free DNA molecules forming a size distribution, the sample being the biological sample or a different sample including a mixture of cell-free DNA molecules from the genome of the subject and from the one or more other genomes;
determining a statistical value of the size distribution;
comparing the statistical value to a reference size value determined from the at least two cohorts of other subjects;
determining a second classification of whether the subject has the first condition based on the comparing of the statistical value to the reference size value; and
determining a final classification using the first classification and the second classification.

24. The system of claim 1, wherein the method further comprises:
determining an amount of cell-free DNA molecules derived from the particular viral genome in a sample, the sample being the biological sample or a different sample including a mixture of cell-free DNA molecules from the genome of the subject and from the one or more other genomes;
comparing the amount to a reference value determined from the at least two cohorts of other subjects;

determining a second classification of whether the subject has the first condition based on the comparing of the amount to the reference value; and determining a final classification using the first classification and the second classification.

25. The system of claim 1, wherein the system is configured for:

responsive to the first classification being that the subject has the first condition, providing a treatment to the subject to improve the first condition.

26. A computer product for analyzing a biological sample of a subject that is a human, the biological sample including a mixture of cell-free DNA molecules from a genome of the subject and from one or more other genomes, the computer product comprising a non-transitory computer readable medium storing a plurality of instructions that when executed control a computer system to perform:

analyzing a plurality of cell-free DNA molecules from the biological sample, the plurality of cell-free DNA molecules being 1,000 or more, wherein analyzing a group of the plurality of cell-free DNA molecules includes:

identifying locations of the cell-free DNA molecules in a particular viral genome of a cancer-causing virus; and determining whether the cell-free DNA molecules are methylated at one or more sites of the particular viral genome based on the locations;

measuring a mixture methylation level based on amounts of the plurality of cell-free DNA molecules methylated at a set of sites of the particular viral genome;

comparing the mixture methylation level to one or more reference methylation levels determined from at least two cohorts of other subjects, wherein the at least two cohorts have different classifications associated with the particular viral genome, the different classifications including a first condition, and wherein the first condition is a cancer; and determining a first classification of whether the subject has the first condition based on the comparing, wherein the first condition is nasopharyngeal carcinoma (NPC), hepatocellular carcinoma (HCC), cervical cancer (CC), or head and neck squamous cell carcinoma (HNSCC).

27. The computer product of claim 26, wherein the set of sites are across a plurality of regions.

28. The system of claim 1, wherein the mixture methylation level is measured based on the amounts of the plurality of cell-free DNA molecules methylated at the set of sites of the particular viral genome, wherein the set of sites are across a plurality of regions.

* * * * *